(12) United States Patent
Nasu et al.

(10) Patent No.: US 11,038,118 B2
(45) Date of Patent: *Jun. 15, 2021

(54) COMPOUND, LIGHT-EMITTING MATERIAL, AND ORGANIC LIGHT-EMITTING DEVICE

(71) Applicants: KYULUX, INC., Fukuoka (JP); KYUSHU UNIVERSITY, NATIONAL UNIVERSITY CORPORATION, Fukuoka (JP)

(72) Inventors: Keiro Nasu, Fukuoka (JP); Chihaya Adachi, Fukuoka (JP); Hajime Nakanotani, Fukuoka (JP); Hiroko Nomura, Fukuoka (JP)

(73) Assignees: KYULUX, INC., Fukuoka (JP); KYUSHU UNIVERSITY, NATIONAL UNIVERSITY CORPORATION, Fukuoka (JP)

(*) Notice: Subject to any disclaimer, the term of this patent is extended or adjusted under 35 U.S.C. 154(b) by 346 days.

This patent is subject to a terminal disclaimer.

(21) Appl. No.: 16/066,814

(22) PCT Filed: Dec. 28, 2016

(86) PCT No.: PCT/JP2016/089033
§ 371 (c)(1),
(2) Date: Jun. 28, 2018

(87) PCT Pub. No.: WO2017/115834
PCT Pub. Date: Jul. 6, 2017

(65) Prior Publication Data
US 2019/0013481 A1 Jan. 10, 2019

(30) Foreign Application Priority Data

Dec. 28, 2015 (JP) ............................. JP2015-256570
Apr. 12, 2016 (JP) ................................. 2016-079892

(51) Int. Cl.
*H01L 51/50* (2006.01)
*H01L 51/00* (2006.01)
(Continued)

(52) U.S. Cl.
CPC ........ *H01L 51/0072* (2013.01); *C07D 209/86* (2013.01); *C09K 11/06* (2013.01);
(Continued)

(58) Field of Classification Search
None
See application file for complete search history.

(56) References Cited

U.S. PATENT DOCUMENTS

2015/0129849 A1  5/2015  Kwong et al.
2018/0175294 A1* 6/2018  Duan ................... C07D 417/10

FOREIGN PATENT DOCUMENTS

CN    104204132 A    12/2014
CN    104725298 A    6/2015
(Continued)

OTHER PUBLICATIONS

Japanese and English version of International Preliminary Report on Patentability of Chapter I, i.e., International Search Opinion dated Jul. 3, 2018, in corresponding PCT International appl. No. PCT/JP2016/089033.

(Continued)

*Primary Examiner* — Gregory D Clark
(74) *Attorney, Agent, or Firm* — Browdy and Neimark, PLLC

(57) ABSTRACT

A compound having a structure represented by the following general formula emits delayed fluorescent light and is useful as a light-emitting material. Three or more of $R^1$, $R^2$, $R^4$, and $R^5$ each represent a 9-carbazolyl group, a 10-phenoxazyl group, or a 10-phenothiazyl group, and the balance thereof (Continued)

and $R^3$ each represent a hydrogen atom or a substituent, but exclude a cyano group. $R^3$ excludes an aryl group, a heteroaryl group, and an alkynyl group.

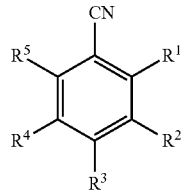

11 Claims, 8 Drawing Sheets

(51) Int. Cl.
  C09K 11/06 (2006.01)
  C07D 209/86 (2006.01)
  H01L 51/56 (2006.01)
  H01L 51/52 (2006.01)
(52) U.S. Cl.
  CPC .. H01L 51/0064 (2013.01); *C09K 2211/1018* (2013.01); *H01L 51/001* (2013.01); *H01L 51/5012* (2013.01); *H01L 51/5056* (2013.01); *H01L 51/5072* (2013.01); *H01L 51/5088* (2013.01); *H01L 51/5092* (2013.01); *H01L 51/5206* (2013.01); *H01L 51/5221* (2013.01); *H01L 51/56* (2013.01); *H01L 2251/308* (2013.01); *H01L 2251/558* (2013.01)

(56) References Cited

FOREIGN PATENT DOCUMENTS

| CN | 105602553 A | 5/2016 |
| CN | 106316924 A | 1/2017 |
| EP | 2039737 A2 | 3/2009 |
| JP | 2009-094486 A | 4/2009 |
| JP | 5366106 B1 | 12/2013 |
| JP | 2015-072889 A | 4/2015 |
| JP | 2015-129113 A | 7/2015 |
| WO | 2013-154064 A1 | 10/2013 |
| WO | 2014-183080 A1 | 11/2014 |
| WO | 2015-066354 A1 | 5/2015 |
| WO | 2016-138077 A | 9/2016 |
| WO | 2016-202251 A1 | 12/2016 |
| WO | 2017-101675 A1 | 6/2017 |
| WO | 2017-107749 A1 | 6/2017 |

OTHER PUBLICATIONS

International Search Report and Search Opinion, dated Mar. 21, 2017, in corresponding PCT International appl. No. PCT/JP2016/089033.
Kretzschmar et al., Development of thermally activated delayed fluorescence materials with shortened emissive lifetimes, The Journal of Organic Chemistry, 9126-9113 (2015).
Uoyama et al., Highly efficient organic light-emitting diodes from delayed fluorescence, Nature, 492:234-240 (2012).
Office Action dated Oct. 6, 2020 issued in the corresponding Japanese patent application No. 2016-079892 with its English Machine Translation.
Office Action dated Sep. 23, 2020 issued in corresponding Chinese patent application No. 201680076802.8 with its English Machine Translation.
OLED, 2015, pp. 33-36.
Taiwanese Office action dated May 5, 2020 from corresponding Taiwanese patent application No. 105143286.
Japanese and English version of Office Action dated Mar. 24, 2020 issued in the corresponding Japanese patent application No. 2016-079892.
Office Action dated Feb. 24, 2021 issued in corresponding Chinese Patent Application No. 201680076802.8 with its English Translation.

* cited by examiner

COMPOUND, LIGHT-EMITTING MATERIAL, AND ORGANIC LIGHT-EMITTING DEVICE

TECHNICAL FIELD

The present invention relates to a compound that is useful as a light-emitting material, and an organic light-emitting device using the same.

BACKGROUND ART

An organic light-emitting device, such as an organic electroluminescent device (organic EL device), has been actively studied for enhancing the light emission efficiency thereof. In particular, various studies for enhancing the light emission efficiency have been made by newly developing and combining an electron transporting material, a hole transporting material, a light-emitting material, and the like constituting an organic electroluminescent device. There are studies focusing on a compound emitting delayed fluorescent light.

Delayed fluorescent light is fluorescent light emitted through such a mechanism that a compound in an excited state through application of energy undergoes reverse intersystem crossing from the excited triplet state to the excited singlet state, and then the excited singlet state returns to the ground state to emit the fluorescent light, and the delayed fluorescent light is fluorescent light that is observed with a delay from the fluorescent light directly emitted from the excited singlet state (normal fluorescent light). With the use of the compound capable of emitting delayed fluorescent light as a light-emitting material of an organic electroluminescent device, the energy of the excited triplet state, which has a large formation probability, can be converted to fluorescent light and thus can be effectively utilized for light emission, from which a high light emission efficiency can be expected. Accordingly, compounds emitting delayed fluorescent light have been actively developed, and there have been some proposals of the utilization of the compound as a light-emitting material.

For example, PTL 1 describes that a compound having a benzene ring having substituted thereon two cyano groups and one or more carbazolyl group or the like is a compound capable of emitting delayed fluorescent light. The literature describes that the use of the compound as a light-emitting material of an organic electroluminescent device and the like can enhance the light emission efficiency.

CITATION LIST

Patent Literature

PTL 1: Japanese Patent No. 5,366,106

SUMMARY OF INVENTION

Technical Problem

However, it is still unclear as to what type of chemical structure can generally emit delayed fluorescent light. For example, compounds that are similar to the compound described in PTL 1 do not necessarily emit delayed fluorescent light, and it is difficult to estimate from the structure as to whether or not delayed fluorescent light is emitted therefrom. Accordingly, for employing compounds capable of emitting delayed fluorescent light from a wider range of compounds, it is considered that a compound capable of emitting delayed fluorescent light is necessarily discovered and utilized from outside the range of the compounds proposed by PTL 1.

Under the circumstances, the present inventors have made earnest investigations for discovering a compound emitting delayed fluorescent light even though having a structure that is not described in PTL 1. The inventors have made earnest investigations for eliciting the general formula of the compound and generalizing the structure of an organic light-emitting device having a high light emission efficiency.

Solution to Problem

As a result of the earnest investigations, the inventors have found that a compound capable of emitting delayed fluorescent light exists in compounds having a structure containing a benzene ring having only one cyano group substituted thereon. The inventors have reached knowledge that the use of the compound capable of emitting delayed fluorescent light as a light-emitting material can provide an organic light-emitting device having a high light emission efficiency. The invention is proposed based on the knowledge and specifically has the following constitution.

[1] A compound having a structure represented by the following general formula (1):

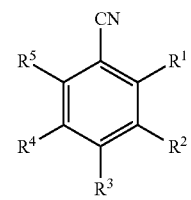

General Formula (1)

wherein in the general formula (1), three or more of $R^1$, $R^2$, $R^4$, and $R^5$ each independently represent a substituted or unsubstituted 9-carbazolyl group, a substituted or unsubstituted 10-phenoxazyl group, or a substituted or unsubstituted 10-phenothiazyl group, and the balance thereof represents a hydrogen atom or a substituent, provided that the substituent excludes a substituted or unsubstituted 9-carbazolyl group, a substituted or unsubstituted 10-phenoxazyl group, a substituted or unsubstituted 10-phenothiazyl group, and a cyano group, and one or more of carbon atom constituting ring skeletons of the substituted or unsubstituted 9-carbazolyl group, the substituted or unsubstituted 10-phenoxazyl group, and the substituted or unsubstituted 10-phenothiazyl group may be replaced by a nitrogen atom; and $R^3$ represents a hydrogen atom or a substituent, provided that the substituent excludes a substituted or unsubstituted 9-carbazolyl group, a substituted or unsubstituted 10-phenoxazyl group, a cyano group, a substituted or unsubstituted 10-phenothiazyl group, a substituted or unsubstituted aryl group, a substituted or unsubstituted heteroaryl group, and a substituted or unsubstituted alkynyl group.

[2] The compound according to the item [1], wherein three or more of $R^1$, $R^2$, $R^4$, and $R^5$ each represent a 9-carbazolyl group substituted with one or more substituent selected from a substituted or unsubstituted branched alkyl group, a substituted or unsubstituted alkoxy group, and a substituted or unsubstituted diarylamino group, or an unsubstituted 9-carbazolyl group.

[3] The compound according to the item [1] or [2], wherein three or more of $R^1$, $R^2$, $R^4$, and $R^5$ each represent a 9-carbazolyl group substituted with one or more substituted or unsubstituted branched alkyl group.

[4] The compound according to the item [1] or [2], wherein all $R^1$, $R^2$, $R^4$, and $R^5$ each represent a substituted or unsubstituted 9-carbazolyl group.

[5] The compound according to the item [1] or [2], wherein three of $R^1$, $R^2$, $R^4$, and $R^5$ each represent a substituted or unsubstituted 9-carbazolyl group.

[6] The compound according to the item [1] or [2], wherein three or more of $R^1$, $R^2$, $R^4$, and $R^5$ represent unsubstituted 9-carbazolyl groups.

[7] The compound according to any one of the items [1] to [3], wherein three or more of $R^1$, $R^2$, $R^4$, and $R^5$ each represent a 9-carbazolyl group substituted with substituents at the 3-position and the 6-position.

[8] The compound according to any one of the items [1] to [7], wherein $R^3$ represents a hydrogen atom.

[9] A light-emitting material containing the compound according to any one of the items [1] to [8].

[10] The light-emitting material according to the item [9], wherein the light-emitting material emits delayed fluorescent light.

[11] An organic light-emitting device containing a substrate having thereon a light-emitting layer containing the light-emitting material according to the item [9] or [10].

[12] The organic light-emitting device according to the item [11], wherein the organic light-emitting device is an organic electroluminescent device.

[13] The organic light-emitting device according to the item [11] or [12], wherein the light-emitting layer contains the compound according to any one of the items [1] to [8] and a host material.

[14] A delayed fluorescent material having a structure represented by the following general formula (1'):

General Formula (1')

wherein in the general formula (1'), three or more of $R^{1'}$, $R^{2'}$, $R^{4'}$, and $R^{5'}$ each independently represent a substituted or unsubstituted 9-carbazolyl group, a substituted or unsubstituted 10-phenoxazyl group, or a substituted or unsubstituted 10-phenothiazyl group, and the balance thereof represents a hydrogen atom or a substituent, provided that the substituent excludes a substituted or unsubstituted 9-carbazolyl group, a substituted or unsubstituted 10-phenoxazyl group, a substituted or unsubstituted 10-phenothiazyl group, and a cyano group, and one or more of carbon atom constituting ring skeletons of the substituted or unsubstituted 9-carbazolyl group, the substituted or unsubstituted 10-phenoxazyl group, and the substituted or unsubstituted 10-phenothiazyl group may be replaced by a nitrogen atom; and $R^{3'}$ represents a hydrogen atom or a substituent, provided that the substituent excludes a substituted or unsubstituted 9-carbazolyl group, a substituted or unsubstituted 10-phenoxazyl group, a substituted or unsubstituted 10-phenothiazyl group, or a cyano group.

Advantageous Effects of Invention

The compound of the invention is useful as a light-emitting material. The compound of the invention can emit delayed fluorescent light, and the triplet excitation energy thereof can be effectively utilized for light emission. Accordingly, the organic light-emitting device using the compound of the invention as a light-emitting material can achieve a high light emission efficiency.

DESCRIPTION OF EMBODIMENTS

Figure 1:
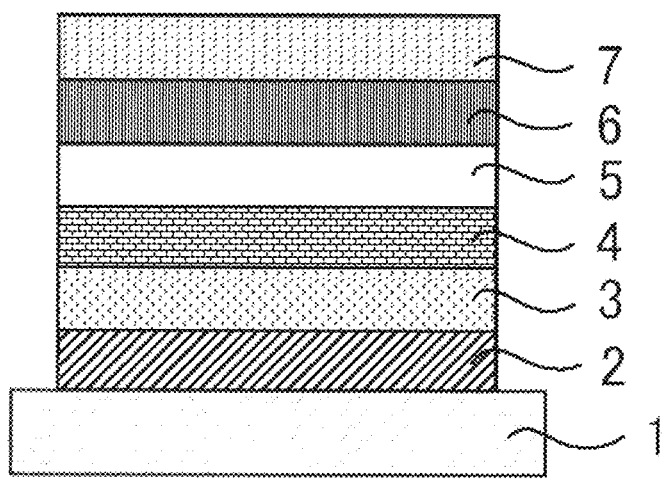
FIG. 1 is a schematic cross sectional view showing an example of a layer structure of an organic electroluminescent device.

The contents of the invention will be described in detail below. The constitutional elements may be described below with reference to representative embodiments and specific examples of the invention, but the invention is not limited to the embodiments and the examples. In the description herein, a numerical range expressed as "to" means a range that includes the upper limit and/or the lower limit. In the invention, the hydrogen atom that is present in the compound used in the invention is not particularly limited in isotope species, and for example, all the hydrogen atoms in the molecule may be $^1H$, and all or a part of them may be $^2H$ (deuterium (D)).

Compound Represented by General Formula (1)

The light-emitting material of the invention contains a compound represented by the following general formula (1).

General Formula (1)

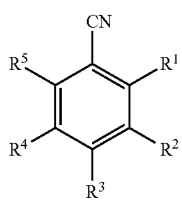

In the general formula (1), three or more of $R^1$, $R^2$, $R^4$, and $R^5$ each independently represent a substituted or unsubstituted 9-carbazolyl group, a substituted or unsubstituted 10-phenoxazyl group, or a substituted or unsubstituted 10-phenothiazyl group, and the balance thereof represents a hydrogen atom or a substituent, provided that the substituent excludes a substituted or unsubstituted 9-carbazolyl group, a substituted or unsubstituted 10-phenoxazyl group, a substituted or unsubstituted 10-phenothiazyl group, or a cyano group.

The number of moieties of $R^1$, $R^2$, $R^4$, and $R^5$ that each represent a substituted or unsubstituted 9-carbazolyl group, a substituted or unsubstituted 10-phenoxazyl group, or a substituted or unsubstituted 10-phenothiazyl group may be three or four, and is preferably four. In the case where three of $R^1$, $R^2$, $R^4$, and $R^5$ each represent a substituted or unsubstituted 9-carbazolyl group, a substituted or unsubstituted 10-phenoxazyl group, or a substituted or unsubstituted 10-phenothiazyl group, the moieties that each represent one of these groups may be $R^1$, $R^2$, and $R^4$, and may be $R^1$, $R^2$, and $R^5$. The moieties of $R^1$, $R^2$, $R^4$, and $R^5$ that each represent a substituted or unsubstituted 9-carbazolyl group, a substituted or unsubstituted 10-phenoxazyl group, or a substituted or unsubstituted 10-phenothiazyl group may have the same structure or different structures, and preferably have the same structure.

At least one of $R^1$, $R^2$, $R^4$, and $R^5$ preferably represents a substituted or unsubstituted 9-carbazolyl group, and three or more thereof each more preferably represent a substituted or unsubstituted 9-carbazolyl group, i.e., it is more preferred that all $R^1$, $R^2$, $R^4$, and $R^5$ each represent a substituted or unsubstituted 9-carbazolyl group, or three of $R^1$, $R^2$, $R^4$, and $R^5$ each represent a substituted or unsubstituted 9-carbazolyl group. Three or more of $R^1$, $R^2$, $R^4$, and $R^5$ each more preferably represent a 9-carbazolyl group substituted with one or more substituent selected from a substituted or unsubstituted branched alkyl group, a substituted or unsubstituted alkoxy group, and a substituted or unsubstituted diarylamino group, or an unsubstituted 9-carbazolyl group, further preferably represent a 9-carbazolyl group substituted with one or more substituent selected from an unsubstituted branched alkyl group having from 3 to 20 carbon atoms, an unsubstituted alkoxy group having from 1 to 20 carbon atoms, a diarylamino group substituted with an unsubstituted alkoxy group having from 1 to 20 carbon atoms, and an unsubstituted diarylamino group, or an unsubstituted 9-carbazolyl group, and particularly preferably represent a 9-carbazolyl group substituted with one or more unsubstituted branched alkyl group having from 3 to 20 carbon atoms, or an unsubstituted 9-carbazolyl group. The number of carbon atoms of the unsubstituted branched alkyl group is more preferably from 3 to 10, and further preferably from 3 to 5. In the case where the 9-carbazolyl group has a substituent, the substitution position thereof is not particularly limited. Preferred examples thereof include a case where at least one of the 3-position and the 6-position is substituted, and more preferred examples include a case where both the 3-position and the 6-position are substituted.

One or more of carbon atom constituting ring skeletons of the 9-carbazolyl group, the 10-phenoxazyl group, and the 10-phenothiazyl group in each of $R^1$, $R^2$, $R^4$, and $R^5$ may be replaced by a nitrogen atom. The number of carbon atoms that are replaced by a nitrogen atom is not particularly limited, and is preferably from 1 to 4, and more preferably 1 or 2.

$R^3$ represents a hydrogen atom or a substituent, provided that the substituent excludes a substituted or unsubstituted 9-carbazolyl group, a substituted or unsubstituted 10-phenoxazyl group, a substituted or unsubstituted 10-phenothiazyl group, a cyano group, a substituted or unsubstituted aryl group, a substituted or unsubstituted heteroaryl group, and a substituted or unsubstituted alkynyl group. $R^3$ preferably represent a hydrogen atom.

In the case where $R^1$, $R^2$, $R^4$, and $R^5$ each represent 10-phenoxazyl group substituted with a substituent or a 10-phenothiazyl group substituted with a substituent, examples of the substituent of the 10-phenoxazyl group and the 10-phenothiazyl group include a hydroxyl group, a halogen atom, a cyano group, an alkyl group having from 1 to 20 carbon atoms, an alkoxy group having from 1 to 20 carbon atoms, an alkylthio group having from 1 to 20 carbon atoms, an alkyl-substituted amino group having from 1 to 20 carbon atoms, an acyl group having from 2 to 20 carbon atoms, an aryl group having from 6 to 40 carbon atoms, a heteroaryl group having from 3 to 40 carbon atoms, an alkenyl group having from 2 to 10 carbon atoms, an alkynyl group having from 2 to 10 carbon atoms, an alkoxycarbonyl group having from 2 to 10 carbon atoms, an alkylsulfonyl group having from 1 to 10 carbon atoms, a haloalkyl group having from 1 to 10 carbon atoms, an amide group, an alkylamide group having from 2 to 10 carbon atoms, a trialkylsilyl group having from 3 to 20 carbon atoms, a trialkylsilylalkyl group having from 4 to 20 carbon atoms, a trialkylsilylalkenyl group having from 5 to 20 carbon atoms, a trialkylsilylalkynyl group having from 5 to 20 carbon atoms, and a nitro group. In these specific examples, the substituent that is capable of being further substituted with a substituent may be substituted. More preferred examples of the substituent include a halogen atom, a cyano group, a substituted or unsubstituted alkyl group having from 1 to 20 carbon atoms, a substituted or unsubstituted alkoxy group having from 1 to 20 carbon atoms, a substituted or unsubstituted aryl group having from 6 to 40 carbon atoms, a substituted or unsubstituted heteroaryl group having from 3 to 40 carbon atoms, and a dialkyl-substituted amino group having from 2 to 20 carbon atoms. Further preferred examples of the substituent include a fluorine atom, a chlorine atom, a cyano group, a substituted or unsubstituted alkyl group having from 1 to 10 carbon atoms, a substituted or unsubstituted alkoxy group having from 1 to 10 carbon atoms, a substituted or unsubstituted aryl group having from 6 to 15 carbon atoms, and a substituted or unsubstituted heteroaryl group having from 3 to 12 carbon atoms.

In the case where three of $R^1$, $R^2$, $R^4$, and $R^5$ each represent a substituted or unsubstituted 9-carbazolyl group, a substituted or unsubstituted 10-phenoxazyl group, or a substituted or unsubstituted 10-phenothiazyl group, examples of the substituent capable of being represented by $R^1$, $R^2$, $R^4$, or $R^5$ include the groups exemplified for the substituent of the 10-phenoxazyl group or the 10-phenothiazyl group, except for a cyano group, provided that the heteroaryl group excludes a substituted or unsubstituted 9-carbazolyl group, a substituted or unsubstituted 10-phenoxazyl group, and a substituted or unsubstituted 10-phenothiazyl group. More preferred examples of the substituent include a substituted or unsubstituted alkyl group having from 1 to 20 carbon atoms, a substituted or unsubstituted alkoxy group having from 1 to 20 carbon atoms, and a substituted or unsubstituted aryl group having from 6 to 40 carbon atoms.

Examples of the substituent capable of being represented by $R^3$ include the groups exemplified for the substituent of the 10-phenoxazyl group and the 10-phenothiazyl group, except for a substituted or unsubstituted aryl group having from 6 to 40 carbon atoms, a substituted or unsubstituted heteroaryl group having from 3 to 40 carbon atoms, an alkynyl group having from 2 to 10 carbon atoms, a trialkylsilylalkynyl group having from 5 to 20 carbon atoms, and a cyano group. More preferred examples of the substituent include a substituted or unsubstituted alkyl group having from 1 to 20 carbon atoms, a substituted or unsubstituted alkoxy group having from 1 to 20 carbon atoms, and a dialkyl-substituted amino group having from 2 to 20 carbon atoms. In the dialkylamino group, the alkyl groups may be bonded to each other via an oxygen atom or the like to form a ring structure.

Specific examples of $R^1$, $R^2$, $R^4$, or $R^5$ in the general formula (1) (D1 to D38) and specific examples of the compound represented by the general formula (1) (Compounds 1 to 835 in Table 1) are shown below. However, in the invention, $R^1$, $R^2$, $R^4$, or $R^5$ in the general formula (1) and the compound represented by the general formula (1) are not construed as being limited to the specific examples. In Table 1, "t-Bu" shows a tert-butyl group, and "Ph" shows a phenyl group.

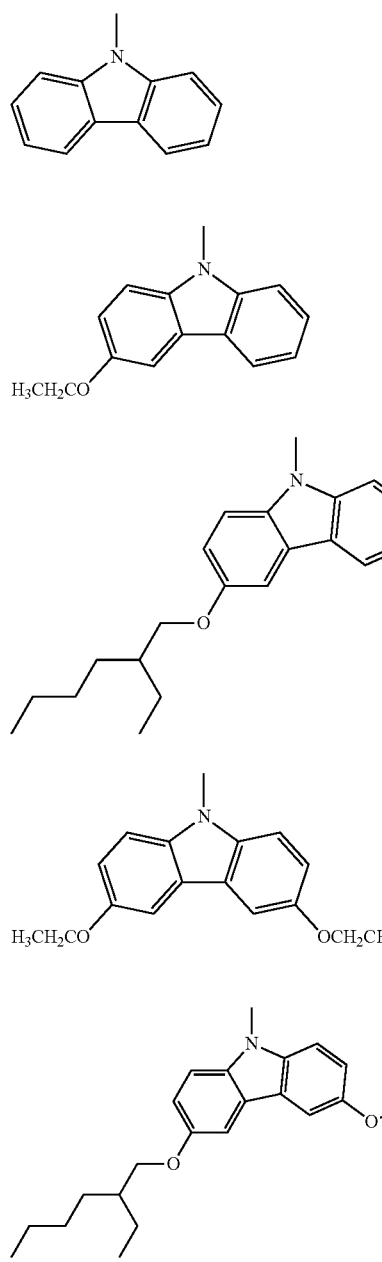

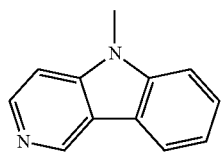
D11
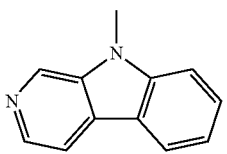
D12
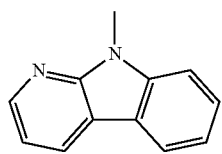
D13
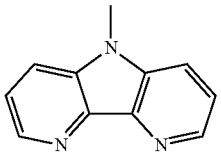
D14
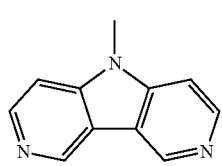
D15
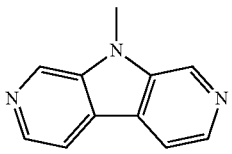
D16
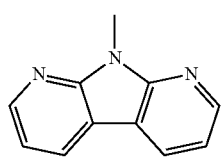
D17
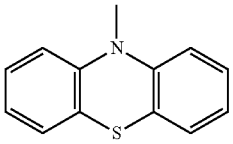
D18
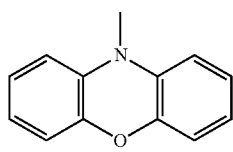
D19
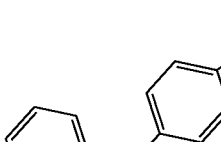
D20
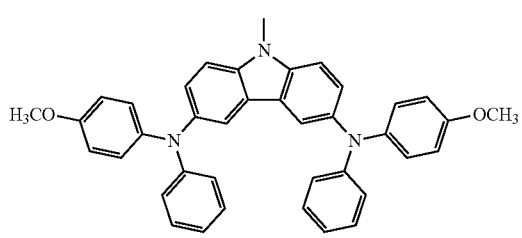
D21
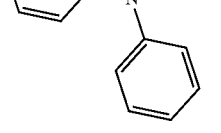
D22
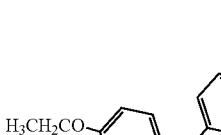
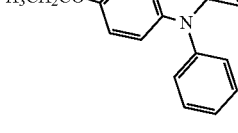
D23
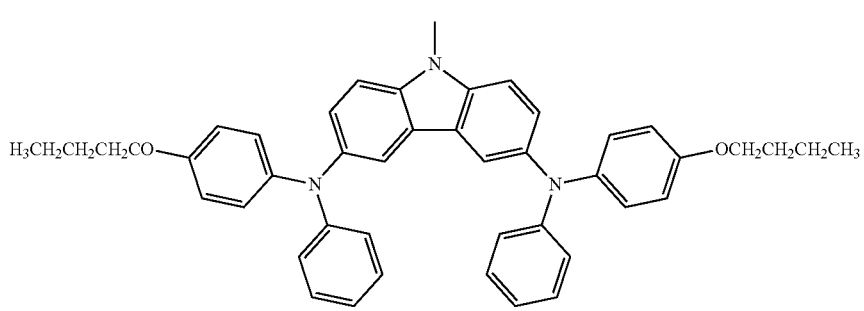

-continued
D24
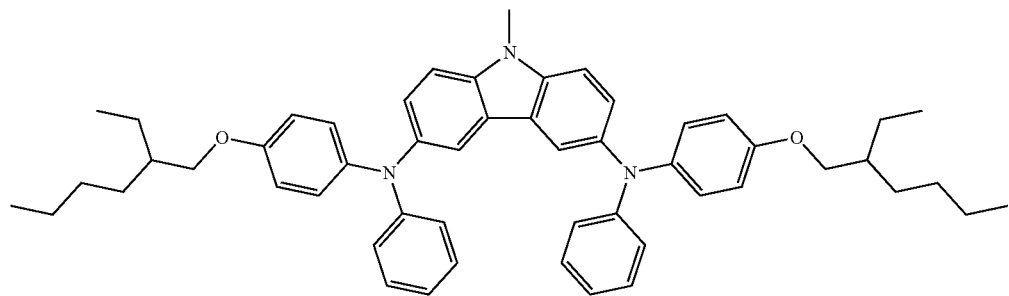
D25
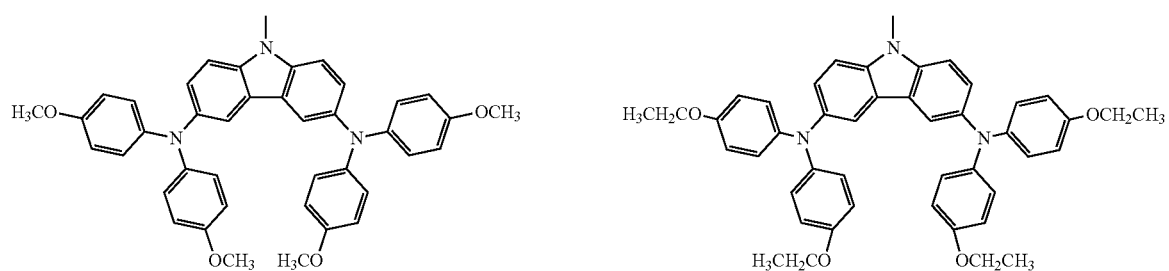
D26
D27
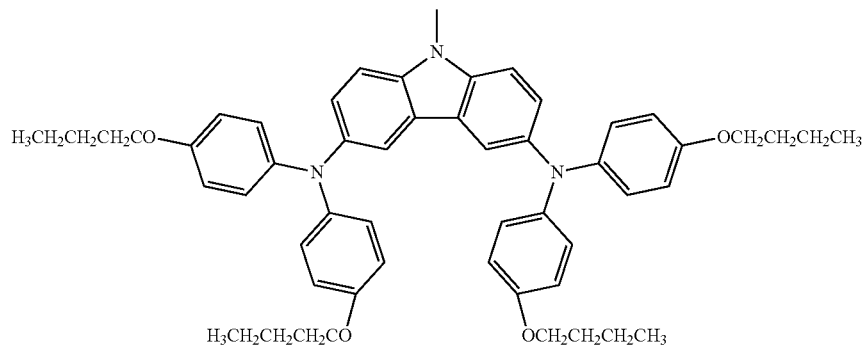
D28
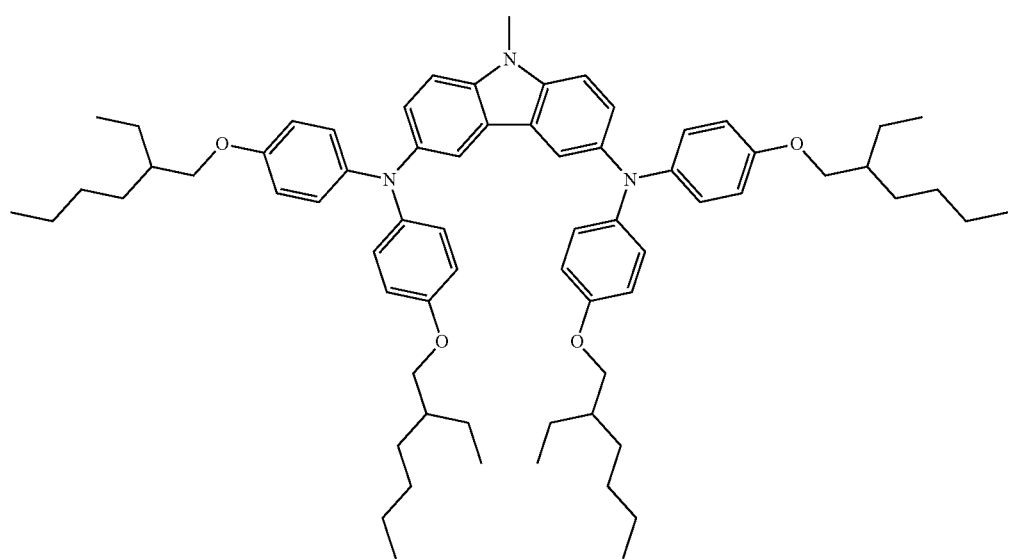

-continued
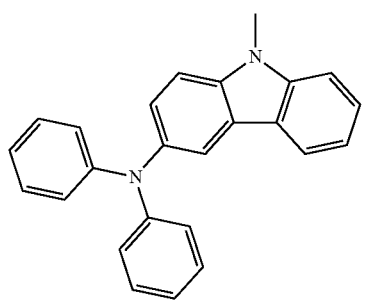
D29
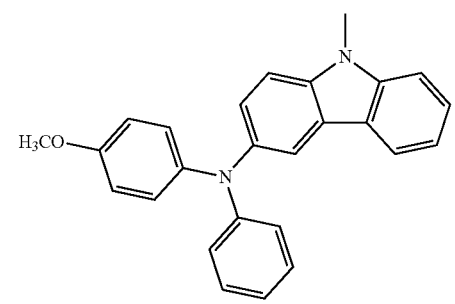
D30
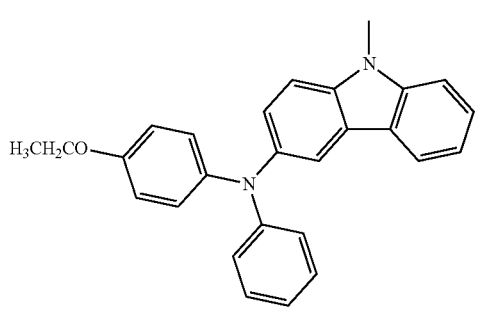
D31
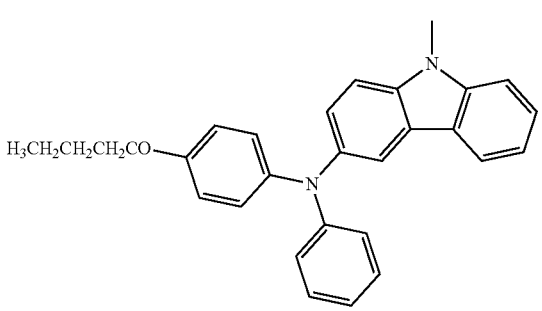
D32
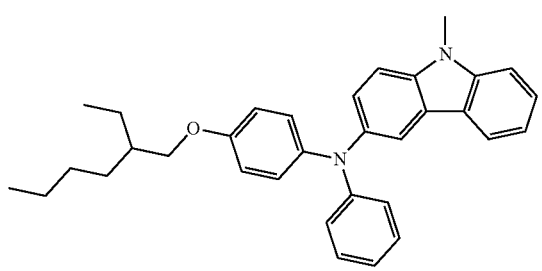
D33
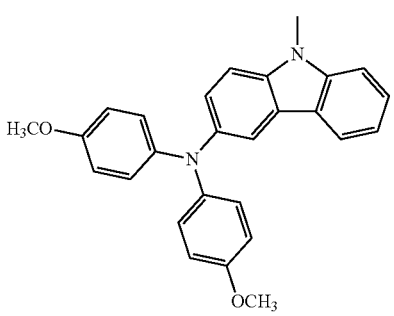
D34
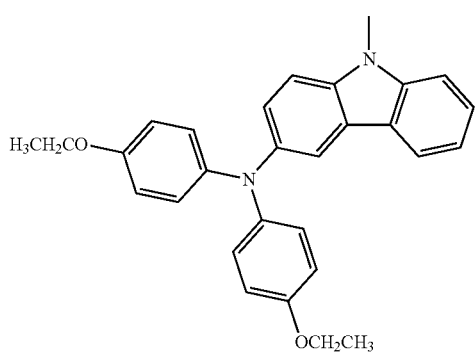
D35
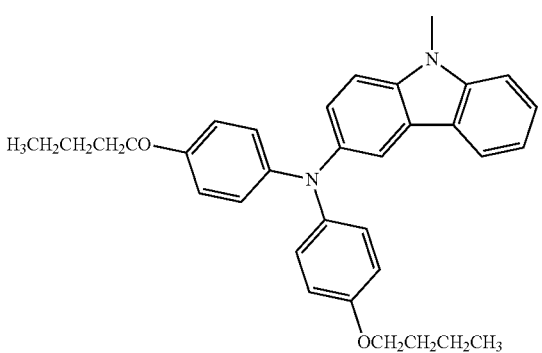
D36

-continued

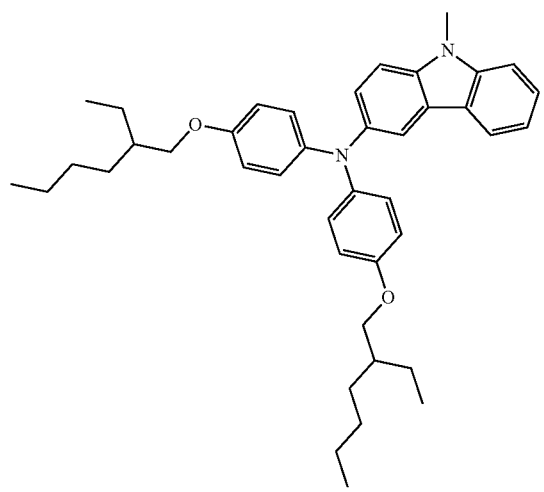
D37

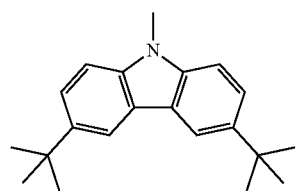
D38

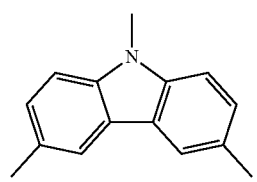
D39

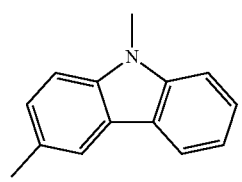
D40

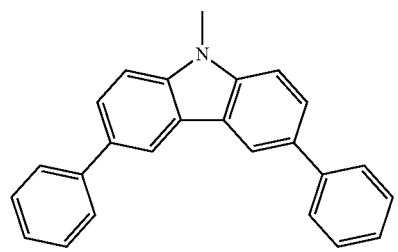
D41

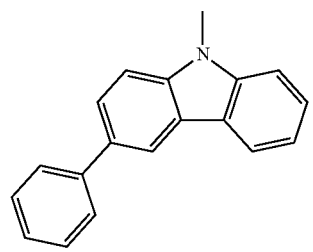
D42

TABLE 1

| Compound No. | $R^1$ | $R^2$ | $R^3$ | $R^4$ | $R^5$ |
|---|---|---|---|---|---|
| 1 | D1 | D1 | H | D1 | D1 |
| 2 | D1 | D1 | H | H | D1 |
| 3 | D1 | D1 | H | D1 | H |
| 4 | D2 | D2 | H | D2 | H |
| 5 | D2 | D2 | H | H | D2 |
| 6 | D2 | D2 | H | D2 | D2 |
| 7 | D3 | D3 | H | D3 | H |
| 8 | D3 | D3 | H | H | D3 |
| 9 | D3 | D3 | H | D3 | D3 |
| 10 | D4 | D4 | H | D4 | H |
| 11 | D4 | D4 | H | H | D4 |
| 12 | D4 | D4 | H | D4 | D4 |
| 13 | D5 | D5 | H | D5 | H |
| 14 | D5 | D5 | H | H | D5 |
| 15 | D5 | D5 | H | D5 | D5 |
| 16 | D6 | D6 | H | D6 | H |
| 17 | D6 | D6 | H | H | D6 |
| 18 | D6 | D6 | H | D6 | D6 |
| 19 | D7 | D7 | H | D7 | H |
| 20 | D7 | D7 | H | H | D7 |
| 21 | D7 | D7 | H | D7 | D7 |
| 22 | D8 | D8 | H | D8 | H |
| 23 | D8 | D8 | H | H | D8 |
| 24 | D8 | D8 | H | D8 | D8 |
| 25 | D9 | D9 | H | D9 | H |
| 26 | D9 | D9 | H | H | D9 |
| 27 | D9 | D9 | H | D9 | D9 |
| 28 | D10 | D10 | H | D10 | H |
| 29 | D10 | D10 | H | H | D10 |
| 30 | D10 | D10 | H | D10 | D10 |
| 31 | D11 | D11 | H | D11 | H |
| 32 | D11 | D11 | H | H | D11 |
| 33 | D11 | D11 | H | D11 | D11 |
| 34 | D12 | D12 | H | D12 | H |
| 35 | D12 | D12 | H | H | D12 |
| 36 | D12 | D12 | H | D12 | D12 |
| 37 | D13 | D13 | H | D13 | H |
| 38 | D13 | D13 | H | H | D13 |
| 39 | D13 | D13 | H | D13 | D13 |
| 40 | D14 | D14 | H | D14 | H |
| 41 | D14 | D14 | H | H | D14 |
| 42 | D14 | D14 | H | D14 | D14 |
| 43 | D15 | D15 | H | D15 | H |
| 44 | D15 | D15 | H | H | D15 |
| 45 | D15 | D15 | H | D15 | D15 |
| 46 | D16 | D16 | H | D16 | H |
| 47 | D16 | D16 | H | H | D16 |
| 48 | D16 | D16 | H | D16 | D16 |
| 49 | D17 | D17 | H | D17 | H |
| 50 | D17 | D17 | H | H | D17 |
| 51 | D17 | D17 | H | D17 | D17 |
| 52 | D18 | D18 | H | D18 | H |
| 53 | D18 | D18 | H | H | D18 |
| 54 | D18 | D18 | H | D18 | D18 |
| 55 | D19 | D19 | H | D19 | H |
| 56 | D19 | D19 | H | H | D19 |

TABLE 1-continued

| Compound No. | R¹ | R² | R³ | R⁴ | R⁵ |
|---|---|---|---|---|---|
| 57 | D19 | D19 | H | D19 | D19 |
| 58 | D20 | D20 | H | D20 | H |
| 59 | D20 | D20 | H | H | D20 |
| 60 | D20 | D20 | H | D20 | D20 |
| 61 | D21 | D21 | H | D21 | H |
| 62 | D21 | D21 | H | H | D21 |
| 63 | D21 | D21 | H | D21 | D21 |
| 64 | D22 | D22 | H | D22 | H |
| 65 | D22 | D22 | H | H | D22 |
| 66 | D22 | D22 | H | D22 | D22 |
| 67 | D23 | D23 | H | D23 | H |
| 68 | D23 | D23 | H | H | D23 |
| 69 | D23 | D23 | H | D23 | D23 |
| 70 | D24 | D24 | H | D24 | H |
| 71 | D24 | D24 | H | H | D24 |
| 72 | D24 | D24 | H | D24 | D24 |
| 73 | D25 | D25 | H | D25 | H |
| 74 | D25 | D25 | H | H | D25 |
| 75 | D25 | D25 | H | D25 | D25 |
| 76 | D26 | D26 | H | D26 | H |
| 77 | D26 | D26 | H | H | D26 |
| 78 | D26 | D26 | H | D26 | D26 |
| 79 | D27 | D27 | H | D27 | H |
| 80 | D27 | D27 | H | H | D27 |
| 81 | D27 | D27 | H | D27 | D27 |
| 82 | D28 | D28 | H | D28 | H |
| 83 | D28 | D28 | H | H | D28 |
| 84 | D28 | D28 | H | D28 | D28 |
| 85 | D29 | D29 | H | D29 | H |
| 86 | D29 | D29 | H | H | D29 |
| 87 | D29 | D29 | H | D29 | D29 |
| 88 | D30 | D30 | H | D30 | H |
| 89 | D30 | D30 | H | H | D30 |
| 90 | D30 | D30 | H | D30 | D30 |
| 91 | D31 | D31 | H | D31 | H |
| 92 | D31 | D31 | H | H | D31 |
| 93 | D31 | D31 | H | D31 | D31 |
| 94 | D32 | D32 | H | D32 | H |
| 95 | D32 | D32 | H | H | D32 |
| 96 | D32 | D32 | H | D32 | D32 |
| 97 | D33 | D33 | H | D33 | H |
| 98 | D33 | D33 | H | H | D33 |
| 99 | D33 | D33 | H | D33 | D33 |
| 100 | D34 | D34 | H | D34 | H |
| 101 | D34 | D34 | H | H | D34 |
| 102 | D34 | D34 | H | D34 | D34 |
| 103 | D35 | D35 | H | D35 | H |
| 104 | D35 | D35 | H | H | D35 |
| 105 | D35 | D35 | H | D35 | D35 |
| 106 | D36 | D36 | H | D36 | H |
| 107 | D36 | D36 | H | H | D36 |
| 108 | D36 | D36 | H | D36 | D36 |
| 109 | D37 | D37 | H | D37 | H |
| 110 | D37 | D37 | H | H | D37 |
| 111 | D1 | D1 | methyl | D1 | methyl |
| 112 | D1 | D1 | methyl | methyl | D1 |
| 113 | D1 | D1 | methyl | D1 | D1 |
| 114 | D2 | D2 | methyl | D2 | methyl |
| 115 | D2 | D2 | methyl | methyl | D2 |
| 116 | D2 | D2 | methyl | D2 | D2 |
| 117 | D3 | D3 | methyl | D3 | methyl |
| 118 | D3 | D3 | methyl | methyl | D3 |
| 119 | D3 | D3 | methyl | D3 | D3 |
| 120 | D4 | D4 | methyl | D4 | methyl |
| 121 | D4 | D4 | methyl | methyl | D4 |
| 122 | D4 | D4 | methyl | D4 | D4 |
| 123 | D5 | D5 | methyl | D5 | methyl |
| 124 | D5 | D5 | methyl | methyl | D5 |
| 125 | D5 | D5 | methyl | D5 | D5 |
| 126 | D6 | D6 | methyl | D6 | methyl |
| 127 | D6 | D6 | methyl | methyl | D6 |
| 128 | D6 | D6 | methyl | D6 | D6 |
| 129 | D7 | D7 | methyl | D7 | methyl |
| 130 | D7 | D7 | methyl | methyl | D7 |
| 131 | D7 | D7 | methyl | D7 | D7 |
| 132 | D8 | D8 | methyl | D8 | methyl |
| 133 | D8 | D8 | methyl | methyl | D8 |
| 134 | D8 | D8 | methyl | D8 | D8 |
| 135 | D9 | D9 | methyl | D9 | methyl |
| 136 | D9 | D9 | methyl | methyl | D9 |
| 137 | D9 | D9 | methyl | D9 | D9 |
| 138 | D10 | D10 | methyl | D10 | methyl |
| 139 | D10 | D10 | methyl | methyl | D10 |
| 140 | D10 | D10 | methyl | D10 | D10 |
| 141 | D11 | D11 | methyl | D11 | methyl |
| 142 | D11 | D11 | methyl | methyl | D11 |
| 143 | D11 | D11 | methyl | D11 | D11 |
| 144 | D12 | D12 | methyl | D12 | methyl |
| 145 | D12 | D12 | methyl | methyl | D12 |
| 146 | D12 | D12 | methyl | D12 | D12 |
| 147 | D13 | D13 | methyl | D13 | methyl |
| 148 | D13 | D13 | methyl | methyl | D13 |
| 149 | D13 | D13 | methyl | D13 | D13 |
| 150 | D14 | D14 | methyl | D14 | methyl |
| 151 | D14 | D14 | methyl | methyl | D14 |
| 152 | D14 | D14 | methyl | D14 | D14 |
| 153 | D15 | D15 | methyl | D15 | methyl |
| 154 | D15 | D15 | methyl | methyl | D15 |
| 155 | D15 | D15 | methyl | D15 | D15 |
| 156 | D16 | D16 | methyl | D16 | methyl |
| 157 | D16 | D16 | methyl | methyl | D16 |
| 158 | D16 | D16 | methyl | D16 | D16 |
| 159 | D17 | D17 | methyl | D17 | methyl |
| 160 | D17 | D17 | methyl | methyl | D17 |
| 161 | D17 | D17 | methyl | D17 | D17 |
| 162 | D18 | D18 | methyl | D18 | methyl |
| 163 | D18 | D18 | methyl | methyl | D18 |
| 164 | D18 | D18 | methyl | D18 | D18 |
| 165 | D19 | D19 | methyl | D19 | methyl |
| 166 | D19 | D19 | methyl | methyl | D19 |
| 167 | D19 | D19 | methyl | D19 | D19 |
| 168 | D20 | D20 | methyl | D20 | methyl |
| 169 | D20 | D20 | methyl | methyl | D20 |
| 170 | D20 | D20 | methyl | D20 | D20 |
| 171 | D21 | D21 | methyl | D21 | methyl |
| 172 | D21 | D21 | methyl | methyl | D21 |
| 173 | D21 | D21 | methyl | D21 | D21 |
| 174 | D22 | D22 | methyl | D22 | methyl |
| 175 | D22 | D22 | methyl | methyl | D22 |
| 176 | D22 | D22 | methyl | D22 | D22 |
| 177 | D23 | D23 | methyl | D23 | methyl |
| 178 | D23 | D23 | methyl | methyl | D23 |
| 179 | D23 | D23 | methyl | D23 | D23 |
| 180 | D24 | D24 | methyl | D24 | methyl |
| 181 | D24 | D24 | methyl | methyl | D24 |
| 182 | D24 | D24 | methyl | D24 | D24 |
| 183 | D25 | D25 | methyl | D25 | methyl |
| 184 | D25 | D25 | methyl | methyl | D25 |
| 185 | D25 | D25 | methyl | D25 | D25 |
| 186 | D26 | D26 | methyl | D26 | methyl |
| 187 | D26 | D26 | methyl | methyl | D26 |
| 188 | D26 | D26 | methyl | D26 | D26 |
| 189 | D27 | D27 | methyl | D27 | methyl |
| 190 | D27 | D27 | methyl | methyl | D27 |
| 191 | D27 | D27 | methyl | D27 | D27 |
| 192 | D28 | D28 | methyl | D28 | methyl |
| 193 | D28 | D28 | methyl | methyl | D28 |
| 194 | D28 | D28 | methyl | D28 | D28 |
| 195 | D29 | D29 | methyl | D29 | methyl |
| 196 | D29 | D29 | methyl | methyl | D29 |
| 197 | D29 | D29 | methyl | D29 | D29 |
| 198 | D30 | D30 | methyl | D30 | methyl |
| 199 | D30 | D30 | methyl | methyl | D30 |
| 200 | D30 | D30 | methyl | D30 | D30 |
| 201 | D31 | D31 | methyl | D31 | methyl |
| 202 | D31 | D31 | methyl | methyl | D31 |
| 203 | D31 | D31 | methyl | D31 | D31 |
| 204 | D32 | D32 | methyl | D32 | methyl |
| 205 | D32 | D32 | methyl | methyl | D32 |
| 206 | D32 | D32 | methyl | D32 | D32 |
| 207 | D33 | D33 | methyl | D33 | methyl |
| 208 | D33 | D33 | methyl | methyl | D33 |
| 209 | D33 | D33 | methyl | D33 | D33 |
| 210 | D34 | D34 | methyl | D34 | methyl |
| 211 | D34 | D34 | methyl | methyl | D34 |
| 212 | D34 | D34 | methyl | D34 | D34 |

TABLE 1-continued

| Compound No. | R¹ | R² | R³ | R⁴ | R⁵ |
|---|---|---|---|---|---|
| 213 | D35 | D35 | methyl | D35 | methyl |
| 214 | D35 | D35 | methyl | methyl | D35 |
| 215 | D35 | D35 | methyl | D35 | D35 |
| 216 | D36 | D36 | methyl | D36 | methyl |
| 217 | D36 | D36 | methyl | methyl | D36 |
| 218 | D36 | D36 | methyl | D36 | D36 |
| 219 | D37 | D37 | methyl | D37 | methyl |
| 220 | D37 | D37 | methyl | methyl | D37 |
| 221 | D37 | D37 | methyl | D37 | D37 |
| 222 | D1 | D1 | isopropyl | D1 | isopropyl |
| 223 | D1 | D1 | isopropyl | isopropyl | D1 |
| 224 | D1 | D1 | isopropyl | D1 | D1 |
| 225 | D2 | D2 | isopropyl | D2 | isopropyl |
| 226 | D2 | D2 | isopropyl | isopropyl | D2 |
| 227 | D2 | D2 | isopropyl | D2 | D2 |
| 228 | D3 | D3 | isopropyl | D3 | isopropyl |
| 229 | D3 | D3 | isopropyl | isopropyl | D3 |
| 230 | D3 | D3 | isopropyl | D3 | D3 |
| 231 | D4 | D4 | isopropyl | D4 | isopropyl |
| 232 | D4 | D4 | isopropyl | isopropyl | D4 |
| 233 | D4 | D4 | isopropyl | D4 | D4 |
| 234 | D5 | D5 | isopropyl | D5 | isopropyl |
| 235 | D5 | D5 | isopropyl | isopropyl | D5 |
| 236 | D5 | D5 | isopropyl | D5 | D5 |
| 237 | D6 | D6 | isopropyl | D6 | isopropyl |
| 238 | D6 | D6 | isopropyl | isopropyl | D6 |
| 239 | D6 | D6 | isopropyl | D6 | D6 |
| 240 | D7 | D7 | isopropyl | D7 | isopropyl |
| 241 | D7 | D7 | isopropyl | isopropyl | D7 |
| 242 | D7 | D7 | isopropyl | D7 | D7 |
| 243 | D8 | D8 | isopropyl | D8 | isopropyl |
| 244 | D8 | D8 | isopropyl | isopropyl | D8 |
| 245 | D8 | D8 | isopropyl | D8 | D8 |
| 246 | D9 | D9 | isopropyl | D9 | isopropyl |
| 247 | D9 | D9 | isopropyl | isopropyl | D9 |
| 248 | D9 | D9 | isopropyl | D9 | D9 |
| 249 | D10 | D10 | isopropyl | D10 | isopropyl |
| 250 | D10 | D10 | isopropyl | isopropyl | D10 |
| 251 | D10 | D10 | isopropyl | D10 | D10 |
| 252 | D11 | D11 | isopropyl | D11 | isopropyl |
| 253 | D11 | D11 | isopropyl | isopropyl | D11 |
| 254 | D11 | D11 | isopropyl | D11 | D11 |
| 255 | D12 | D12 | isopropyl | D12 | isopropyl |
| 256 | D12 | D12 | isopropyl | isopropyl | D12 |
| 257 | D12 | D12 | isopropyl | D12 | D12 |
| 258 | D13 | D13 | isopropyl | D13 | isopropyl |
| 259 | D13 | D13 | isopropyl | isopropyl | D13 |
| 260 | D13 | D13 | isopropyl | D13 | D13 |
| 261 | D14 | D14 | isopropyl | D14 | isopropyl |
| 262 | D14 | D14 | isopropyl | isopropyl | D14 |
| 263 | D14 | D14 | isopropyl | D14 | D14 |
| 264 | D15 | D15 | isopropyl | D15 | isopropyl |
| 265 | D15 | D15 | isopropyl | isopropyl | D15 |
| 266 | D15 | D15 | isopropyl | D15 | D15 |
| 267 | D16 | D16 | isopropyl | D16 | isopropyl |
| 268 | D16 | D16 | isopropyl | isopropyl | D16 |
| 269 | D16 | D16 | isopropyl | D16 | D16 |
| 270 | D17 | D17 | isopropyl | D17 | isopropyl |
| 271 | D17 | D17 | isopropyl | isopropyl | D17 |
| 272 | D17 | D17 | isopropyl | D17 | D17 |
| 273 | D18 | D18 | isopropyl | D18 | isopropyl |
| 274 | D18 | D18 | isopropyl | isopropyl | D18 |
| 275 | D18 | D18 | isopropyl | D18 | D18 |
| 276 | D19 | D19 | isopropyl | D19 | isopropyl |
| 277 | D19 | D19 | isopropyl | isopropyl | D19 |
| 278 | D19 | D19 | isopropyl | D19 | D19 |
| 279 | D20 | D20 | isopropyl | D20 | isopropyl |
| 280 | D20 | D20 | isopropyl | isopropyl | D20 |
| 281 | D20 | D20 | isopropyl | D20 | D20 |
| 282 | D21 | D21 | isopropyl | D21 | isopropyl |
| 283 | D21 | D21 | isopropyl | isopropyl | D21 |
| 284 | D21 | D21 | isopropyl | D21 | D21 |
| 285 | D22 | D22 | isopropyl | D22 | isopropyl |
| 286 | D22 | D22 | isopropyl | isopropyl | D22 |
| 287 | D22 | D22 | isopropyl | D22 | D22 |
| 288 | D23 | D23 | isopropyl | D23 | isopropyl |
| 289 | D23 | D23 | isopropyl | isopropyl | D23 |
| 290 | D23 | D23 | isopropyl | D23 | D23 |
| 291 | D24 | D24 | isopropyl | D24 | isopropyl |
| 292 | D24 | D24 | isopropyl | isopropyl | D24 |
| 293 | D24 | D24 | isopropyl | D24 | D24 |
| 294 | D25 | D25 | isopropyl | D25 | isopropyl |
| 295 | D25 | D25 | isopropyl | isopropyl | D25 |
| 296 | D25 | D25 | isopropyl | D25 | D25 |
| 297 | D26 | D26 | isopropyl | D26 | isopropyl |
| 298 | D26 | D26 | isopropyl | isopropyl | D26 |
| 299 | D26 | D26 | isopropyl | D26 | D26 |
| 300 | D27 | D27 | isopropyl | D27 | isopropyl |
| 301 | D27 | D27 | isopropyl | isopropyl | D27 |
| 302 | D27 | D27 | isopropyl | D27 | D27 |
| 303 | D28 | D28 | isopropyl | D28 | isopropyl |
| 304 | D28 | D28 | isopropyl | isopropyl | D28 |
| 305 | D28 | D28 | isopropyl | D28 | D28 |
| 306 | D29 | D29 | isopropyl | D29 | isopropyl |
| 307 | D29 | D29 | isopropyl | isopropyl | D29 |
| 308 | D29 | D29 | isopropyl | D29 | D29 |
| 309 | D30 | D30 | isopropyl | D30 | isopropyl |
| 310 | D30 | D30 | isopropyl | isopropyl | D30 |
| 311 | D30 | D30 | isopropyl | D30 | D30 |
| 312 | D31 | D31 | isopropyl | D31 | isopropyl |
| 313 | D31 | D31 | isopropyl | isopropyl | D31 |
| 314 | D31 | D31 | isopropyl | D31 | D31 |
| 315 | D32 | D32 | isopropyl | D32 | isopropyl |
| 316 | D32 | D32 | isopropyl | isopropyl | D32 |
| 317 | D32 | D32 | isopropyl | D32 | D32 |
| 318 | D33 | D33 | isopropyl | D33 | isopropyl |
| 319 | D33 | D33 | isopropyl | isopropyl | D33 |
| 320 | D33 | D33 | isopropyl | D33 | D33 |
| 321 | D34 | D34 | isopropyl | D34 | isopropyl |
| 322 | D34 | D34 | isopropyl | isopropyl | D34 |
| 323 | D34 | D34 | isopropyl | D34 | D34 |
| 324 | D35 | D35 | isopropyl | D35 | isopropyl |
| 325 | D35 | D35 | isopropyl | isopropyl | D35 |
| 326 | D35 | D35 | isopropyl | D35 | D35 |
| 327 | D36 | D36 | isopropyl | D36 | isopropyl |
| 328 | D36 | D36 | isopropyl | isopropyl | D36 |
| 329 | D36 | D36 | isopropyl | D36 | D36 |
| 330 | D37 | D37 | isopropyl | D37 | isopropyl |
| 331 | D37 | D37 | isopropyl | isopropyl | D37 |
| 332 | D37 | D37 | isopropyl | D37 | D37 |
| 333 | D1 | D1 | tBu | D1 | tBu |
| 334 | D1 | D1 | tBu | tBu | D1 |
| 335 | D1 | D1 | tBu | D1 | D1 |
| 336 | D2 | D2 | tBu | D2 | tBu |
| 337 | D2 | D2 | tBu | tBu | D2 |
| 338 | D2 | D2 | tBu | D2 | D2 |
| 339 | D3 | D3 | tBu | D3 | tBu |
| 340 | D3 | D3 | tBu | tBu | D3 |
| 341 | D3 | D3 | tBu | D3 | D3 |
| 342 | D4 | D4 | tBu | D4 | tBu |
| 343 | D4 | D4 | tBu | tBu | D4 |
| 344 | D4 | D4 | tBu | D4 | D4 |
| 345 | D5 | D5 | tBu | D5 | tBu |
| 346 | D5 | D5 | tBu | tBu | D5 |
| 347 | D5 | D5 | tBu | D5 | D5 |
| 348 | D6 | D6 | tBu | D6 | tBu |
| 349 | D6 | D6 | tBu | tBu | D6 |
| 350 | D6 | D6 | tBu | D6 | D6 |
| 351 | D7 | D7 | tBu | D7 | tBu |
| 352 | D7 | D7 | tBu | tBu | D7 |
| 353 | D7 | D7 | tBu | D7 | D7 |
| 354 | D8 | D8 | tBu | D8 | tBu |
| 355 | D8 | D8 | tBu | tBu | D8 |
| 356 | D8 | D8 | tBu | D8 | D8 |
| 357 | D9 | D9 | tBu | D9 | tBu |
| 358 | D9 | D9 | tBu | tBu | D9 |
| 359 | D9 | D9 | tBu | D9 | D9 |
| 360 | D10 | D10 | tBu | D10 | tBu |
| 361 | D10 | D10 | tBu | tBu | D10 |
| 362 | D10 | D10 | tBu | D10 | D10 |
| 363 | D11 | D11 | tBu | D11 | tBu |
| 364 | D11 | D11 | tBu | tBu | D11 |
| 365 | D11 | D11 | tBu | D11 | D11 |
| 366 | D12 | D12 | tBu | D12 | tBu |
| 367 | D12 | D12 | tBu | tBu | D12 |
| 368 | D12 | D12 | tBu | D12 | D12 |

TABLE 1-continued

| Compound No. | R¹ | R² | R³ | R⁴ | R⁵ |
|---|---|---|---|---|---|
| 369 | D13 | D13 | tBu | D13 | tBu |
| 370 | D13 | D13 | tBu | tBu | D13 |
| 371 | D13 | D13 | tBu | D13 | D13 |
| 372 | D14 | D14 | tBu | D14 | tBu |
| 373 | D14 | D14 | tBu | tBu | D14 |
| 374 | D14 | D14 | tBu | D14 | D14 |
| 375 | D15 | D15 | tBu | D15 | tBu |
| 376 | D15 | D15 | tBu | tBu | D15 |
| 377 | D15 | D15 | tBu | D15 | D15 |
| 378 | D16 | D16 | tBu | D16 | tBu |
| 379 | D16 | D16 | tBu | tBu | D16 |
| 380 | D16 | D16 | tBu | D16 | D16 |
| 381 | D17 | D17 | tBu | D17 | tBu |
| 382 | D17 | D17 | tBu | tBu | D17 |
| 383 | D17 | D17 | tBu | D17 | D17 |
| 384 | D18 | D18 | tBu | D18 | tBu |
| 385 | D18 | D18 | tBu | tBu | D18 |
| 386 | D18 | D18 | tBu | D18 | D18 |
| 387 | D19 | D19 | tBu | D19 | tBu |
| 388 | D19 | D19 | tBu | tBu | D19 |
| 389 | D19 | D19 | tBu | D19 | D19 |
| 390 | D20 | D20 | tBu | D20 | tBu |
| 391 | D20 | D20 | tBu | tBu | D20 |
| 392 | D20 | D20 | tBu | D20 | D20 |
| 393 | D21 | D21 | tBu | D21 | tBu |
| 394 | D21 | D21 | tBu | tBu | D21 |
| 395 | D21 | D21 | tBu | D21 | D21 |
| 396 | D22 | D22 | tBu | D22 | tBu |
| 397 | D22 | D22 | tBu | tBu | D22 |
| 398 | D22 | D22 | tBu | D22 | D22 |
| 399 | D23 | D23 | tBu | D23 | tBu |
| 400 | D23 | D23 | tBu | tBu | D23 |
| 401 | D23 | D23 | tBu | D23 | D23 |
| 402 | D24 | D24 | tBu | D24 | tBu |
| 403 | D24 | D24 | tBu | tBu | D24 |
| 404 | D24 | D24 | tBu | D24 | D24 |
| 405 | D25 | D25 | tBu | D25 | tBu |
| 406 | D25 | D25 | tBu | tBu | D25 |
| 407 | D25 | D25 | tBu | D25 | D25 |
| 408 | D26 | D26 | tBu | D26 | tBu |
| 409 | D26 | D26 | tBu | tBu | D26 |
| 410 | D26 | D26 | tBu | D26 | D26 |
| 411 | D27 | D27 | tBu | D27 | tBu |
| 412 | D27 | D27 | tBu | tBu | D27 |
| 413 | D27 | D27 | tBu | D27 | D27 |
| 414 | D28 | D28 | tBu | D28 | tBu |
| 415 | D28 | D28 | tBu | tBu | D28 |
| 416 | D28 | D28 | tBu | D28 | D28 |
| 417 | D29 | D29 | tBu | D29 | tBu |
| 418 | D29 | D29 | tBu | tBu | D29 |
| 419 | D29 | D29 | tBu | D29 | D29 |
| 420 | D30 | D30 | tBu | D30 | tBu |
| 421 | D30 | D30 | tBu | tBu | D30 |
| 422 | D30 | D30 | tBu | D30 | D30 |
| 423 | D31 | D31 | tBu | D31 | tBu |
| 424 | D31 | D31 | tBu | tBu | D31 |
| 425 | D31 | D31 | tBu | D31 | D31 |
| 426 | D32 | D32 | tBu | D32 | tBu |
| 427 | D32 | D32 | tBu | tBu | D32 |
| 428 | D32 | D32 | tBu | D32 | D32 |
| 429 | D33 | D33 | tBu | D33 | tBu |
| 430 | D33 | D33 | tBu | tBu | D33 |
| 431 | D33 | D33 | tBu | D33 | D33 |
| 432 | D34 | D34 | tBu | D34 | tBu |
| 433 | D34 | D34 | tBu | tBu | D34 |
| 434 | D34 | D34 | tBu | D34 | D34 |
| 435 | D35 | D35 | tBu | D35 | tBu |
| 436 | D35 | D35 | tBu | tBu | D35 |
| 437 | D35 | D35 | tBu | D35 | D35 |
| 438 | D36 | D36 | tBu | D36 | tBu |
| 439 | D36 | D36 | tBu | tBu | D36 |
| 440 | D36 | D36 | tBu | D36 | D36 |
| 441 | D37 | D37 | tBu | D37 | tBu |
| 442 | D37 | D37 | tBu | tBu | D37 |
| 443 | D37 | D37 | tBu | D37 | D37 |
| 444 | D1 | D1 | methoxy | D1 | methoxy |
| 445 | D1 | D1 | methoxy | methoxy | D1 |
| 446 | D1 | D1 | methoxy | D1 | D1 |
| 447 | D2 | D2 | methoxy | D2 | methoxy |
| 448 | D2 | D2 | methoxy | methoxy | D2 |
| 449 | D2 | D2 | methoxy | D2 | D2 |
| 450 | D3 | D3 | methoxy | D3 | methoxy |
| 451 | D3 | D3 | methoxy | methoxy | D3 |
| 452 | D3 | D3 | methoxy | D3 | D3 |
| 453 | D4 | D4 | methoxy | D4 | methoxy |
| 454 | D4 | D4 | methoxy | methoxy | D4 |
| 455 | D4 | D4 | methoxy | D4 | D4 |
| 456 | D5 | D5 | methoxy | D5 | methoxy |
| 457 | D5 | D5 | methoxy | methoxy | D5 |
| 458 | D5 | D5 | methoxy | D5 | D5 |
| 459 | D6 | D6 | methoxy | D6 | methoxy |
| 460 | D6 | D6 | methoxy | methoxy | D6 |
| 461 | D6 | D6 | methoxy | D6 | D6 |
| 462 | D7 | D7 | methoxy | D7 | methoxy |
| 463 | D7 | D7 | methoxy | methoxy | D7 |
| 464 | D7 | D7 | methoxy | D7 | D7 |
| 465 | D8 | D8 | methoxy | D8 | methoxy |
| 466 | D8 | D8 | methoxy | methoxy | D8 |
| 467 | D8 | D8 | methoxy | D8 | D8 |
| 468 | D9 | D9 | methoxy | D9 | methoxy |
| 469 | D9 | D9 | methoxy | methoxy | D9 |
| 470 | D9 | D9 | methoxy | D9 | D9 |
| 471 | D10 | D10 | methoxy | D10 | methoxy |
| 472 | D10 | D10 | methoxy | methoxy | D10 |
| 473 | D10 | D10 | methoxy | D10 | D10 |
| 474 | D11 | D11 | methoxy | D11 | methoxy |
| 475 | D11 | D11 | methoxy | methoxy | D11 |
| 476 | D11 | D11 | methoxy | D11 | D11 |
| 477 | D12 | D12 | methoxy | D12 | methoxy |
| 478 | D12 | D12 | methoxy | methoxy | D12 |
| 479 | D12 | D12 | methoxy | D12 | D12 |
| 480 | D13 | D13 | methoxy | D13 | methoxy |
| 481 | D13 | D13 | methoxy | methoxy | D13 |
| 482 | D13 | D13 | methoxy | D13 | D13 |
| 483 | D14 | D14 | methoxy | D14 | methoxy |
| 484 | D14 | D14 | methoxy | methoxy | D14 |
| 485 | D14 | D14 | methoxy | D14 | D14 |
| 486 | D15 | D15 | methoxy | D15 | methoxy |
| 487 | D15 | D15 | methoxy | methoxy | D15 |
| 488 | D15 | D15 | methoxy | D15 | D15 |
| 489 | D16 | D16 | methoxy | D16 | methoxy |
| 490 | D16 | D16 | methoxy | methoxy | D16 |
| 491 | D16 | D16 | methoxy | D16 | D16 |
| 492 | D17 | D17 | methoxy | D17 | methoxy |
| 493 | D17 | D17 | methoxy | methoxy | D17 |
| 494 | D17 | D17 | methoxy | D17 | D17 |
| 495 | D18 | D18 | methoxy | D18 | methoxy |
| 496 | D18 | D18 | methoxy | methoxy | D18 |
| 497 | D18 | D18 | methoxy | D18 | D18 |
| 498 | D19 | D19 | methoxy | D19 | methoxy |
| 499 | D19 | D19 | methoxy | methoxy | D19 |
| 500 | D19 | D19 | methoxy | D19 | D19 |
| 501 | D20 | D20 | methoxy | D20 | methoxy |
| 502 | D20 | D20 | methoxy | methoxy | D20 |
| 503 | D20 | D20 | methoxy | D20 | D20 |
| 504 | D21 | D21 | methoxy | D21 | methoxy |
| 505 | D21 | D21 | methoxy | methoxy | D21 |
| 506 | D21 | D21 | methoxy | D21 | D21 |
| 507 | D22 | D22 | methoxy | D22 | methoxy |
| 508 | D22 | D22 | methoxy | methoxy | D22 |
| 509 | D22 | D22 | methoxy | D22 | D22 |
| 510 | D23 | D23 | methoxy | D23 | methoxy |
| 511 | D23 | D23 | methoxy | methoxy | D23 |
| 512 | D23 | D23 | methoxy | D23 | D23 |
| 513 | D24 | D24 | methoxy | D24 | methoxy |
| 514 | D24 | D24 | methoxy | methoxy | D24 |
| 515 | D24 | D24 | methoxy | D24 | D24 |
| 516 | D25 | D25 | methoxy | D25 | methoxy |
| 517 | D25 | D25 | methoxy | methoxy | D25 |
| 518 | D25 | D25 | methoxy | D25 | D25 |
| 519 | D26 | D26 | methoxy | D26 | methoxy |
| 520 | D26 | D26 | methoxy | methoxy | D26 |
| 521 | D26 | D26 | methoxy | D26 | D26 |
| 522 | D27 | D27 | methoxy | D27 | methoxy |
| 523 | D27 | D27 | methoxy | methoxy | D27 |
| 524 | D27 | D27 | methoxy | D27 | D27 |

TABLE 1-continued

| Compound No. | R¹ | R² | R³ | R⁴ | R⁵ |
| --- | --- | --- | --- | --- | --- |
| 525 | D28 | D28 | methoxy | D28 | methoxy |
| 526 | D28 | D28 | methoxy | methoxy | D28 |
| 527 | D28 | D28 | methoxy | D28 | D28 |
| 528 | D29 | D29 | methoxy | D29 | methoxy |
| 529 | D29 | D29 | methoxy | methoxy | D29 |
| 530 | D29 | D29 | methoxy | D29 | D29 |
| 531 | D30 | D30 | methoxy | D30 | methoxy |
| 532 | D30 | D30 | methoxy | methoxy | D30 |
| 533 | D30 | D30 | methoxy | D30 | D30 |
| 534 | D31 | D31 | methoxy | D31 | methoxy |
| 535 | D31 | D31 | methoxy | methoxy | D31 |
| 536 | D31 | D31 | methoxy | D31 | D31 |
| 537 | D32 | D32 | methoxy | D32 | methoxy |
| 538 | D32 | D32 | methoxy | methoxy | D32 |
| 539 | D32 | D32 | methoxy | D32 | D32 |
| 540 | D33 | D33 | methoxy | D33 | methoxy |
| 541 | D33 | D33 | methoxy | methoxy | D33 |
| 542 | D33 | D33 | methoxy | D33 | D33 |
| 543 | D34 | D34 | methoxy | D34 | methoxy |
| 544 | D34 | D34 | methoxy | methoxy | D34 |
| 545 | D34 | D34 | methoxy | D34 | D34 |
| 546 | D35 | D35 | methoxy | D35 | methoxy |
| 547 | D35 | D35 | methoxy | methoxy | D35 |
| 548 | D35 | D35 | methoxy | D35 | D35 |
| 549 | D36 | D36 | methoxy | D36 | methoxy |
| 550 | D36 | D36 | methoxy | methoxy | D36 |
| 551 | D36 | D36 | methoxy | D36 | D36 |
| 552 | D37 | D37 | methoxy | D37 | methoxy |
| 553 | D37 | D37 | methoxy | methoxy | D37 |
| 554 | D37 | D37 | methoxy | D37 | D37 |
| 555 | D1 | D1 | methyl | H | D1 |
| 556 | D2 | D2 | methyl | H | D2 |
| 557 | D3 | D3 | methyl | H | D3 |
| 558 | D4 | D4 | methyl | H | D4 |
| 559 | D5 | D5 | methyl | H | D5 |
| 560 | D6 | D6 | methyl | H | D6 |
| 561 | D7 | D7 | methyl | H | D7 |
| 562 | D8 | D8 | methyl | H | D8 |
| 563 | D9 | D9 | methyl | H | D9 |
| 564 | D10 | D10 | methyl | H | D10 |
| 565 | D11 | D11 | methyl | H | D11 |
| 566 | D12 | D12 | methyl | H | D12 |
| 567 | D13 | D13 | methyl | H | D13 |
| 568 | D14 | D14 | methyl | H | D14 |
| 569 | D15 | D15 | methyl | H | D15 |
| 570 | D16 | D16 | methyl | H | D16 |
| 571 | D17 | D17 | methyl | H | D17 |
| 572 | D18 | D18 | methyl | H | D18 |
| 573 | D19 | D19 | methyl | H | D19 |
| 574 | D20 | D20 | methyl | H | D20 |
| 575 | D21 | D21 | methyl | H | D21 |
| 576 | D22 | D22 | methyl | H | D22 |
| 577 | D23 | D23 | methyl | H | D23 |
| 578 | D24 | D24 | methyl | H | D24 |
| 579 | D25 | D25 | methyl | H | D25 |
| 580 | D26 | D26 | methyl | H | D26 |
| 581 | D27 | D27 | methyl | H | D27 |
| 582 | D28 | D28 | methyl | H | D28 |
| 583 | D29 | D29 | methyl | H | D29 |
| 584 | D30 | D30 | methyl | H | D30 |
| 585 | D31 | D31 | methyl | H | D31 |
| 586 | D32 | D32 | methyl | H | D32 |
| 587 | D33 | D33 | methyl | H | D33 |
| 588 | D34 | D34 | methyl | H | D34 |
| 589 | D35 | D35 | methyl | H | D35 |
| 590 | D36 | D36 | methyl | H | D36 |
| 591 | D37 | D37 | methyl | H | D37 |
| 592 | D1 | D1 | H | methyl | D1 |
| 593 | D2 | D2 | H | methyl | D2 |
| 594 | D3 | D3 | H | methyl | D3 |
| 595 | D4 | D4 | H | methyl | D4 |
| 596 | D5 | D5 | H | methyl | D5 |
| 597 | D6 | D6 | H | methyl | D6 |
| 598 | D7 | D7 | H | methyl | D7 |
| 599 | D8 | D8 | H | methyl | D8 |
| 600 | D9 | D9 | H | methyl | D9 |
| 601 | D10 | D10 | H | methyl | D10 |
| 602 | D11 | D11 | H | methyl | D11 |
| 603 | D12 | D12 | H | methyl | D12 |
| 604 | D13 | D13 | H | methyl | D13 |
| 605 | D14 | D14 | H | methyl | D14 |
| 606 | D15 | D15 | H | methyl | D15 |
| 607 | D16 | D16 | H | methyl | D16 |
| 608 | D17 | D17 | H | methyl | D17 |
| 609 | D18 | D18 | H | methyl | D18 |
| 610 | D19 | D19 | H | methyl | D19 |
| 611 | D20 | D20 | H | methyl | D20 |
| 612 | D21 | D21 | H | methyl | D21 |
| 613 | D22 | D22 | H | methyl | D22 |
| 614 | D23 | D23 | H | methyl | D23 |
| 615 | D24 | D24 | H | methyl | D24 |
| 616 | D25 | D25 | H | methyl | D25 |
| 617 | D26 | D26 | H | methyl | D26 |
| 618 | D27 | D27 | H | methyl | D27 |
| 619 | D28 | D28 | H | methyl | D28 |
| 620 | D29 | D29 | H | methyl | D29 |
| 621 | D30 | D30 | H | methyl | D30 |
| 622 | D31 | D31 | H | methyl | D31 |
| 623 | D32 | D32 | H | methyl | D32 |
| 624 | D33 | D33 | H | methyl | D33 |
| 625 | D34 | D34 | H | methyl | D34 |
| 626 | D35 | D35 | H | methyl | D35 |
| 627 | D36 | D36 | H | methyl | D36 |
| 628 | D37 | D37 | H | methyl | D37 |
| 629 | D1 | D1 | H | D1 | methyl |
| 630 | D2 | D2 | H | D2 | methyl |
| 631 | D3 | D3 | H | D3 | methyl |
| 632 | D4 | D4 | H | D4 | methyl |
| 633 | D5 | D5 | H | D5 | methyl |
| 634 | D6 | D6 | H | D6 | methyl |
| 635 | D7 | D7 | H | D7 | methyl |
| 636 | D8 | D8 | H | D8 | methyl |
| 637 | D9 | D9 | H | D9 | methyl |
| 638 | D10 | D10 | H | D10 | methyl |
| 639 | D11 | D11 | H | D11 | methyl |
| 640 | D12 | D12 | H | D12 | methyl |
| 641 | D13 | D13 | H | D13 | methyl |
| 642 | D14 | D14 | H | D14 | methyl |
| 643 | D15 | D15 | H | D15 | methyl |
| 644 | D16 | D16 | H | D16 | methyl |
| 645 | D17 | D17 | H | D17 | methyl |
| 646 | D18 | D18 | H | D18 | methyl |
| 647 | D19 | D19 | H | D19 | methyl |
| 648 | D20 | D20 | H | D20 | methyl |
| 649 | D21 | D21 | H | D21 | methyl |
| 650 | D22 | D22 | H | D22 | methyl |
| 651 | D23 | D23 | H | D23 | methyl |
| 652 | D24 | D24 | H | D24 | methyl |
| 653 | D25 | D25 | H | D25 | methyl |
| 654 | D26 | D26 | H | D26 | methyl |
| 655 | D27 | D27 | H | D27 | methyl |
| 656 | D28 | D28 | H | D28 | methyl |
| 657 | D29 | D29 | H | D29 | methyl |
| 658 | D30 | D30 | H | D30 | methyl |
| 659 | D31 | D31 | H | D31 | methyl |
| 660 | D32 | D32 | H | D32 | methyl |
| 661 | D33 | D33 | H | D33 | methyl |
| 662 | D34 | D34 | H | D34 | methyl |
| 663 | D35 | D35 | H | D35 | methyl |
| 664 | D36 | D36 | H | D36 | methyl |
| 665 | D37 | D37 | H | D37 | methyl |
| 666 | D1 | D1 | methoxy | H | D1 |
| 667 | D2 | D2 | methoxy | H | D2 |
| 668 | D3 | D3 | methoxy | H | D3 |
| 669 | D4 | D4 | methoxy | H | D4 |
| 670 | D5 | D5 | methoxy | H | D5 |
| 671 | D6 | D6 | methoxy | H | D6 |
| 672 | D7 | D7 | methoxy | H | D7 |
| 673 | D8 | D8 | methoxy | H | D8 |
| 674 | D9 | D9 | methoxy | H | D9 |
| 675 | D10 | D10 | methoxy | H | D10 |
| 676 | D11 | D11 | methoxy | H | D11 |
| 677 | D12 | D12 | methoxy | H | D12 |
| 678 | D13 | D13 | methoxy | H | D13 |
| 679 | D14 | D14 | methoxy | H | D14 |
| 680 | D15 | D15 | methoxy | H | D15 |

TABLE 1-continued

| Compound No. | R¹ | R² | R³ | R⁴ | R⁵ |
|---|---|---|---|---|---|
| 681 | D16 | D16 | methoxy | H | D16 |
| 682 | D17 | D17 | methoxy | H | D17 |
| 683 | D18 | D18 | methoxy | H | D18 |
| 684 | D19 | D19 | methoxy | H | D19 |
| 685 | D20 | D20 | methoxy | H | D20 |
| 686 | D21 | D21 | methoxy | H | D21 |
| 687 | D22 | D22 | methoxy | H | D22 |
| 688 | D23 | D23 | methoxy | H | D23 |
| 689 | D24 | D24 | methoxy | H | D24 |
| 690 | D25 | D25 | methoxy | H | D25 |
| 691 | D26 | D26 | methoxy | H | D26 |
| 692 | D27 | D27 | methoxy | H | D27 |
| 693 | D28 | D28 | methoxy | H | D28 |
| 694 | D29 | D29 | methoxy | H | D29 |
| 695 | D30 | D30 | methoxy | H | D30 |
| 696 | D31 | D31 | methoxy | H | D31 |
| 697 | D32 | D32 | methoxy | H | D32 |
| 698 | D33 | D33 | methoxy | H | D33 |
| 699 | D34 | D34 | methoxy | H | D34 |
| 700 | D35 | D35 | methoxy | H | D35 |
| 701 | D36 | D36 | methoxy | H | D36 |
| 702 | D37 | D37 | methoxy | H | D37 |
| 703 | D1 | D1 | H | methoxy | D1 |
| 704 | D2 | D2 | H | methoxy | D2 |
| 705 | D3 | D3 | H | methoxy | D3 |
| 706 | D4 | D4 | H | methoxy | D4 |
| 707 | D5 | D5 | H | methoxy | D5 |
| 708 | D6 | D6 | H | methoxy | D6 |
| 709 | D7 | D7 | H | methoxy | D7 |
| 710 | D8 | D8 | H | methoxy | D8 |
| 711 | D9 | D9 | H | methoxy | D9 |
| 712 | D10 | D10 | H | methoxy | D10 |
| 713 | D11 | D11 | H | methoxy | D11 |
| 714 | D12 | D12 | H | methoxy | D12 |
| 715 | D13 | D13 | H | methoxy | D13 |
| 716 | D14 | D14 | H | methoxy | D14 |
| 717 | D15 | D15 | H | methoxy | D15 |
| 718 | D16 | D16 | H | methoxy | D16 |
| 719 | D17 | D17 | H | methoxy | D17 |
| 720 | D18 | D18 | H | methoxy | D18 |
| 721 | D19 | D19 | H | methoxy | D19 |
| 722 | D20 | D20 | H | methoxy | D20 |
| 723 | D21 | D21 | H | methoxy | D21 |
| 724 | D22 | D22 | H | methoxy | D22 |
| 725 | D23 | D23 | H | methoxy | D23 |
| 726 | D24 | D24 | H | methoxy | D24 |
| 727 | D25 | D25 | H | methoxy | D25 |
| 728 | D26 | D26 | H | methoxy | D26 |
| 729 | D27 | D27 | H | methoxy | D27 |
| 730 | D28 | D28 | H | methoxy | D28 |
| 731 | D29 | D29 | H | methoxy | D29 |
| 732 | D30 | D30 | H | methoxy | D30 |
| 733 | D31 | D31 | H | methoxy | D31 |
| 734 | D32 | D32 | H | methoxy | D32 |
| 735 | D33 | D33 | H | methoxy | D33 |
| 736 | D34 | D34 | H | methoxy | D34 |
| 737 | D35 | D35 | H | methoxy | D35 |
| 738 | D36 | D36 | H | methoxy | D36 |
| 739 | D37 | D37 | H | methoxy | D37 |
| 740 | D1 | D1 | H | D1 | methoxy |
| 741 | D2 | D2 | H | D2 | methoxy |
| 742 | D3 | D3 | H | D3 | methoxy |
| 743 | D4 | D4 | H | D4 | methoxy |
| 744 | D5 | D5 | H | D5 | methoxy |
| 745 | D6 | D6 | H | D6 | methoxy |
| 746 | D7 | D7 | H | D7 | methoxy |
| 747 | D8 | D8 | H | D8 | methoxy |
| 748 | D9 | D9 | H | D9 | methoxy |
| 749 | D10 | D10 | H | D10 | methoxy |
| 750 | D11 | D11 | H | D11 | methoxy |
| 751 | D12 | D12 | H | D12 | methoxy |
| 752 | D13 | D13 | H | D13 | methoxy |
| 753 | D14 | D14 | H | D14 | methoxy |
| 754 | D15 | D15 | H | D15 | methoxy |
| 755 | D16 | D16 | H | D16 | methoxy |
| 756 | D17 | D17 | H | D17 | methoxy |
| 757 | D18 | D18 | H | D18 | methoxy |
| 758 | D19 | D19 | H | D19 | methoxy |
| 759 | D20 | D20 | H | D20 | methoxy |
| 760 | D21 | D21 | H | D21 | methoxy |
| 761 | D22 | D22 | H | D22 | methoxy |
| 762 | D23 | D23 | H | D23 | methoxy |
| 763 | D24 | D24 | H | D24 | methoxy |
| 764 | D25 | D25 | H | D25 | methoxy |
| 765 | D26 | D26 | H | D26 | methoxy |
| 766 | D27 | D27 | H | D27 | methoxy |
| 767 | D28 | D28 | H | D28 | methoxy |
| 768 | D29 | D29 | H | D29 | methoxy |
| 769 | D30 | D30 | H | D30 | methoxy |
| 770 | D31 | D31 | H | D31 | methoxy |
| 771 | D32 | D32 | H | D32 | methoxy |
| 772 | D33 | D33 | H | D33 | methoxy |
| 773 | D34 | D34 | H | D34 | methoxy |
| 774 | D35 | D35 | H | D35 | methoxy |
| 775 | D36 | D36 | H | D36 | methoxy |
| 776 | D37 | D37 | H | D37 | methoxy |
| 777 | D1 | D1 | morpholine | D1 | D1 |
| 778 | D2 | D2 | morpholine | D2 | D2 |
| 779 | D3 | D3 | morpholine | D3 | D3 |
| 780 | D4 | D4 | morpholine | D4 | D4 |
| 781 | D5 | D5 | morpholine | D5 | D5 |
| 782 | D6 | D6 | morpholine | D6 | D6 |
| 783 | D7 | D7 | morpholine | D7 | D7 |
| 784 | D8 | D8 | morpholine | D8 | D8 |
| 785 | D9 | D9 | morpholine | D9 | D9 |
| 786 | D10 | D10 | morpholine | D10 | D10 |
| 787 | D11 | D11 | morpholine | D11 | D11 |
| 788 | D12 | D12 | morpholine | D12 | D12 |
| 789 | D13 | D13 | morpholine | D13 | D13 |
| 790 | D14 | D14 | morpholine | D14 | D14 |
| 791 | D15 | D15 | morpholine | D15 | D15 |
| 792 | D16 | D16 | morpholine | D16 | D16 |
| 793 | D17 | D17 | morpholine | D17 | D17 |
| 794 | D18 | D18 | morpholine | D18 | D18 |
| 795 | D19 | D19 | morpholine | D19 | D19 |
| 796 | D20 | D20 | morpholine | D20 | D20 |
| 797 | D21 | D21 | morpholine | D21 | D21 |
| 798 | D22 | D22 | morpholine | D22 | D22 |
| 799 | D23 | D23 | morpholine | D23 | D23 |
| 800 | D24 | D24 | morpholine | D24 | D24 |
| 801 | D25 | D25 | morpholine | D25 | D25 |
| 802 | D26 | D26 | morpholine | D26 | D26 |
| 803 | D27 | D27 | morpholine | D27 | D27 |
| 804 | D28 | D28 | morpholine | D28 | D28 |
| 805 | D29 | D29 | morpholine | D29 | D29 |
| 806 | D30 | D30 | morpholine | D30 | D30 |
| 807 | D31 | D31 | morpholine | D31 | D31 |
| 808 | D32 | D32 | morpholine | D32 | D32 |
| 809 | D33 | D33 | morpholine | D33 | D33 |
| 810 | D34 | D34 | morpholine | D34 | D34 |
| 811 | D35 | D35 | morpholine | D35 | D35 |
| 812 | D36 | D36 | morpholine | D36 | D36 |
| 813 | D37 | D37 | morpholine | D37 | D37 |
| 814 | D38 | D38 | H | D38 | H |
| 815 | D38 | D38 | H | H | D38 |
| 816 | D38 | D38 | H | D38 | D38 |
| 817 | D38 | D38 | methyl | D38 | methyl |
| 818 | D38 | D38 | methyl | methyl | D38 |
| 819 | D38 | D38 | methyl | D38 | D38 |

TABLE 1-continued

| Compound No. | R¹ | R² | R³ | R⁴ | R⁵ |
|---|---|---|---|---|---|
| 820 | D38 | D38 | isopropyl | D38 | isopropyl |
| 821 | D38 | D38 | isopropyl | isopropyl | D38 |
| 822 | D38 | D38 | isopropyl | D38 | D38 |
| 823 | D38 | D38 | tBu | D38 | tBu |
| 824 | D38 | D38 | tBu | tBu | D38 |
| 825 | D38 | D38 | tBu | D38 | D38 |
| 826 | D38 | D38 | methoxy | D38 | methoxy |
| 827 | D38 | D38 | methoxy | methoxy | D38 |
| 828 | D38 | D38 | methoxy | D38 | D38 |
| 829 | D38 | D38 | methyl | H | D38 |
| 830 | D38 | D38 | H | methyl | D38 |
| 831 | D38 | D38 | H | D38 | methyl |
| 832 | D38 | D38 | methoxy | H | D38 |
| 833 | D38 | D38 | H | methoxy | D38 |
| 834 | D38 | D38 | H | D38 | methoxy |
| 835 | D38 | D38 | morpholine | D38 | D38 |
| 836 | D39 | D39 | H | D39 | H |
| 837 | D39 | D39 | H | H | D39 |
| 838 | D39 | D39 | H | D39 | D39 |
| 839 | D39 | D39 | methyl | D39 | methyl |
| 840 | D39 | D39 | methyl | methyl | D39 |
| 841 | D39 | D39 | methyl | D39 | D39 |
| 842 | D39 | D39 | isopropyl | D39 | isopropyl |
| 843 | D39 | D39 | isopropyl | isopropyl | D39 |
| 844 | D39 | D39 | isopropyl | D39 | D39 |
| 845 | D39 | D39 | tBu | D39 | tBu |
| 846 | D39 | D39 | tBu | tBu | D39 |
| 847 | D39 | D39 | tBu | D39 | D39 |
| 848 | D39 | D39 | methoxy | D39 | methoxy |
| 849 | D39 | D39 | methoxy | methoxy | D39 |
| 850 | D39 | D39 | methoxy | D39 | D39 |
| 851 | D39 | D39 | methyl | H | D39 |
| 852 | D39 | D39 | H | methyl | D39 |
| 853 | D39 | D39 | H | D39 | methyl |
| 854 | D39 | D39 | methoxy | H | D39 |
| 855 | D39 | D39 | H | methoxy | D39 |
| 856 | D39 | D39 | H | D39 | methoxy |
| 857 | D39 | D39 | morpholine | D39 | D39 |
| 858 | D40 | D40 | H | D40 | H |
| 859 | D40 | D40 | H | H | D40 |
| 860 | D40 | D40 | H | D40 | D40 |
| 861 | D40 | D40 | methyl | D40 | methyl |
| 862 | D40 | D40 | methyl | methyl | D40 |
| 863 | D40 | D40 | methyl | D40 | D40 |
| 864 | D40 | D40 | isopropyl | D40 | isopropyl |
| 865 | D40 | D40 | isopropyl | isopropyl | D40 |
| 866 | D40 | D40 | isopropyl | D40 | D40 |
| 867 | D40 | D40 | tBu | D40 | tBu |
| 868 | D40 | D40 | tBu | tBu | D40 |
| 869 | D40 | D40 | tBu | D40 | D40 |
| 870 | D40 | D40 | methoxy | D40 | methoxy |
| 871 | D40 | D40 | methoxy | methoxy | D40 |
| 872 | D40 | D40 | methoxy | D40 | D40 |
| 873 | D40 | D40 | methyl | H | D40 |
| 874 | D40 | D40 | H | methyl | D40 |
| 875 | D40 | D40 | H | D40 | methyl |
| 876 | D40 | D40 | methoxy | H | D40 |
| 877 | D40 | D40 | H | methoxy | D40 |
| 878 | D40 | D40 | H | D40 | methoxy |
| 879 | D40 | D40 | morpholine | D40 | D40 |
| 880 | D41 | D41 | H | D41 | H |
| 881 | D41 | D41 | H | H | D41 |
| 882 | D41 | D41 | H | D41 | D41 |
| 883 | D41 | D41 | methyl | D41 | methyl |
| 884 | D41 | D41 | methyl | methyl | D41 |
| 885 | D41 | D41 | methyl | D41 | D41 |
| 886 | D41 | D41 | isopropyl | D41 | isopropyl |
| 887 | D41 | D41 | isopropyl | isopropyl | D41 |
| 888 | D41 | D41 | isopropyl | D41 | D41 |
| 889 | D41 | D41 | tBu | D41 | tBu |
| 890 | D41 | D41 | tBu | tBu | D41 |
| 891 | D41 | D41 | tBu | D41 | D41 |
| 892 | D41 | D41 | methoxy | D41 | methoxy |
| 893 | D41 | D41 | methoxy | methoxy | D41 |
| 894 | D41 | D41 | methoxy | D41 | D41 |
| 895 | D41 | D41 | methyl | H | D41 |
| 896 | D41 | D41 | H | methyl | D41 |
| 897 | D41 | D41 | H | D41 | methyl |
| 898 | D41 | D41 | methoxy | H | D41 |
| 899 | D41 | D41 | H | methoxy | D41 |
| 900 | D41 | D41 | H | D41 | methoxy |
| 901 | D41 | D41 | morpholine | D41 | D41 |

The molecular weight of the compound represented by the general formula (1) is preferably 1,500 or less, more preferably 1,200 or less, further preferably 1,000 or less, and still further preferably 800 or less, for example, in the case where an organic layer containing the compound represented by the general formula (1) is intended to be formed as a film by a vapor deposition method. The lower limit of the molecular weight is the molecular weight of the smallest compound represented by the general formula (1).

The compound represented by the general formula (1) may be formed into a film by a coating method irrespective of the molecular weight thereof. The compound that has a relatively large molecular weight may be formed into a film by a coating method.

Synthesis Method of Compound Represented by General Formula (1)

The compound represented by the general formula (1) is a novel compound.

The compound represented by the general formula (1) may be synthesized by combining the known reactions. For example, the compound represented by the general formula (1), wherein $R^1$, $R^2$, $R^4$, and $R^5$ each represent a substituted or unsubstituted 9-carbazolyl group, a substituted or unsubstituted 10-phenoxazyl group, or a substituted or unsubstituted 10-phenothiazyl group may be synthesized by reacting the cyanobenzene derivative with the heteroaromatic compound shown below.

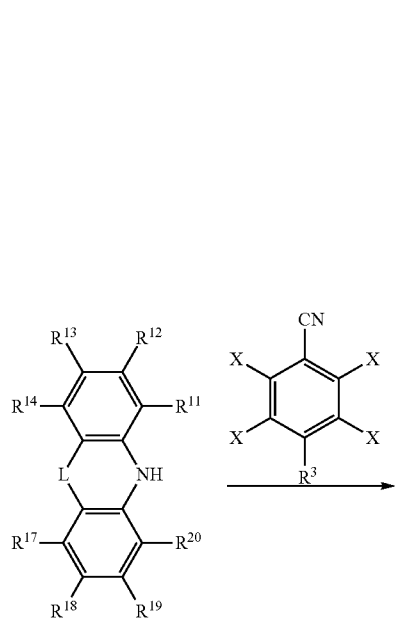
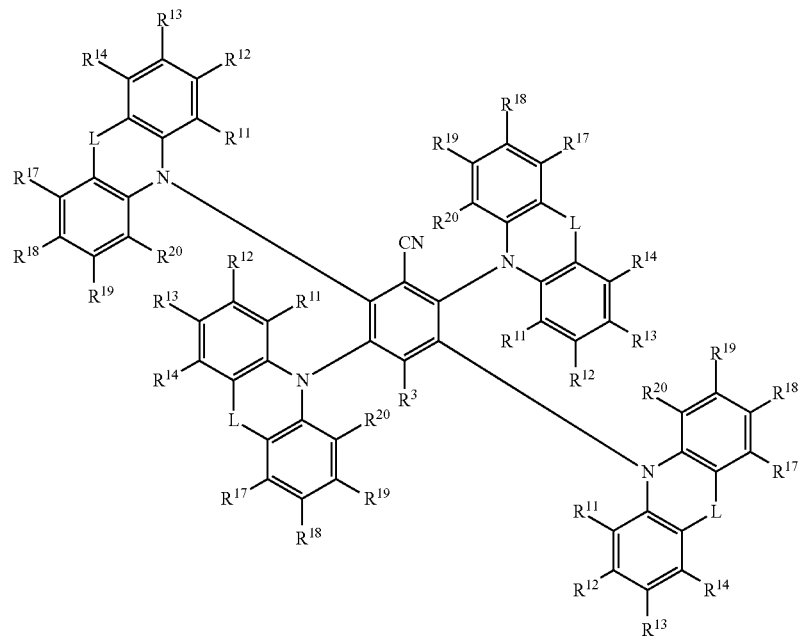

For the description of $R^3$ in the aforementioned reaction scheme, reference may be made to the corresponding description in the general formula (1). $R^{11}$ to $R^{14}$ and $R^{17}$ to $R^{20}$ each independently represent a hydrogen atom or a substituent. L represents a single bond, an oxygen atom, or a sulfur atom. X represents a halogen atom, examples of which include a fluorine atom, a chlorine atom, a bromine atom, and an iodine atom, and a fluorine atom, a bromine atom, and an iodine atom are preferred.

The aforementioned reaction is an application of the known coupling reaction, and the known reaction conditions may be appropriately selected and used. For the details of the reaction, reference may be made to Synthesis Examples described later. The compound represented by the general formula (1) may be synthesized by combining the other known synthesis reactions.

Delayed Fluorescent Material

The delayed fluorescent material of the invention has a structure represented by the following general formula (1'):

General Formula (1')

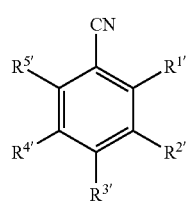

In the general formula (1'), three or more of $R^{1'}$, $R^{2'}$, $R^{4'}$, and $R^{5'}$ each independently represent a substituted or unsubstituted 9-carbazolyl group, a substituted or unsubstituted 10-phenoxazyl group, or a substituted or unsubstituted 10-phenothiazyl group. The balance thereof represents a hydrogen atom or a substituent, provided that the substituent excludes a substituted or unsubstituted 9-carbazolyl group, a substituted or unsubstituted 10-phenoxazyl group, a substituted or unsubstituted 10-phenothiazyl group, or a cyano group. One or more of carbon atom constituting ring skeletons of the substituted or unsubstituted 9-carbazolyl group, the substituted or unsubstituted 10-phenoxazyl group, and the substituted or unsubstituted 10-phenothiazyl group may be replaced by a nitrogen atom. $R^{3'}$ represents a hydrogen atom or a substituent, provided that the substituent excludes a substituted or unsubstituted 9-carbazolyl group, a substituted or unsubstituted 10-phenoxazyl group, a substituted or unsubstituted 10-phenothiazyl group, or a cyano group.

For the description, the preferred ranges, and the specific examples of $R^{1'}$ to $R^{5'}$, reference may be made to the description, the preferred ranges, and the specific examples of $R^1$ to $R^5$ in the compound represented by the general formula (1), provided that examples of the substituent capable of being represented by $R^{3'}$ include, in addition to the substituent capable of being represented by $R^3$, a substituted or unsubstituted aryl group having from 6 to 40 carbon atoms, a substituted or unsubstituted heteroaryl group having from 3 to 40 carbon atoms (that excludes a substituted or unsubstituted 9-carbazolyl group, a substituted or unsubstituted 10-phenoxazyl group, and a substituted or unsubstituted 10-phenothiazyl group), an alkynyl group having from 2 to 10 carbon atoms, and a trialkylsilylalkynyl group having from 5 to 20 carbon atoms.

As an application of the invention, it may be considered that a compound that contains plural structures each represented by the general formula (1) in the molecule is used as a light-emitting material. It may also be considered that a compound that contains plural structures each represented by the general formula (1') in the molecule is used as a delayed fluorescent material.

For example, it may be considered that a polymerizable group is introduced in advance to the structure represented by the general formula (1) or the general formula (1'), and a polymer obtained by polymerizing the polymerizable group is used as a light-emitting material or a delayed fluorescent material. Specifically, it may be considered that a monomer that has a polymerizable functional group at any of $R^1$ to $R^5$ in the general formula (1) or $R^{1'}$ to $R^{5'}$ in the general formula (1') is prepared, and is homopolymerized or copolymerized with another monomer to prepare a polymer containing repeating units, and the polymer is used as a light-emitting material or a delayed fluorescent material. In alternative, it may be considered that the compounds represented by the general formula (1) or the general formula (1') are coupled with each other to form a dimer or a trimer, and the dimer or the trimer is used as a light-emitting material or a delayed fluorescent material.

Examples of the polymer having the repeating unit containing the structure represented by the general formula (1) or the general formula (1') include a polymer containing a structure represented by the following general formula (11) or (12).

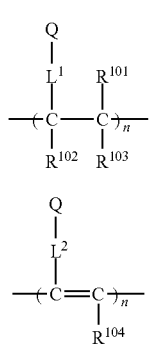

General Formula (11)

General Formula (12)

In the general formulae (11) and (12), Q represents a group containing the structure represented by the general formula (1) or the general formula (1'), and $L^1$ and $L^2$ each represent a linking group. The linking group preferably has a number of carbon atoms of from 0 to 20, more preferably from 1 to 15, and further preferably from 2 to 10. The linking group preferably has a structure represented by $—X^{11}-L^{11}-$, wherein $X^{11}$ represents an oxygen atom or a sulfur atom, and preferably an oxygen atom, and $L^{11}$ represents a linking group, preferably a substituted or unsubstituted alkylene group or a substituted or unsubstituted arylene group, and more preferably a substituted or unsubstituted alkylene group having from 1 to 10 carbon atoms or a substituted or unsubstituted phenylene group.

In the general formulae (11) and (12), $R^{101}$, $R^{102}$, $R^{103}$ and $R^{104}$ each independently represent a substituent, preferably a substituted or unsubstituted alkyl group having from 1 to 6 carbon atoms, a substituted or unsubstituted alkoxy group having from 1 to 6 carbon atoms, or a halogen atom, more preferably an unsubstituted alkyl group having from 1 to 3 carbon atoms, an unsubstituted alkoxy group having from 1 to 3 carbon atoms, a fluorine atom, or a chlorine atom, and further preferably an unsubstituted alkyl group having from 1 to 3 carbon atoms or an unsubstituted alkoxy group having from 1 to 3 carbon atoms.

The linking group represented by $L^1$ and $L^2$ may be bonded to any of $R^1$ to $R^5$ of the structure of the general formula (1) or any of $R^{1'}$ to $R^{5'}$ of the structure of the general formula (1') constituting Q. Two or more of the linking groups may be boded to one group represented by Q to form a crosslinked structure or a network structure.

Specific examples of the structure of the repeating unit include structures represented by the following formulae (13) to (16).

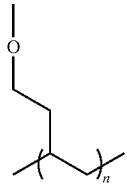

Formula (13)

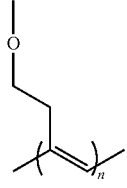

Formula (14)

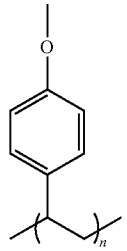

Formula (15)

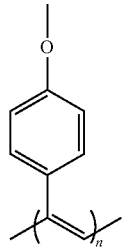

Formula (16)

The polymer having the repeating unit containing the structure represented by any of the formulae (13) to (16) may be synthesized in such a manner that a hydroxyl group is introduced to any of $R^1$ to $R^5$ in the structure represented by the general formula (1) or any of $R^{1'}$ to $R^{5'}$ in the structure represented by the general formula (1'), and the hydroxyl group as a linker is reacted with the following compound to introduce a polymerizable group thereto, followed by polymerizing the polymerizable group.

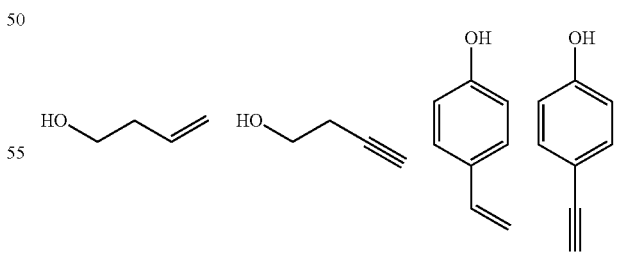

The polymer containing the structure represented by the general formula (1) or the general formula (1') in the molecule may be a polymer containing only a repeating unit having the structure represented by the general formula (1) or the general formula (1'), or a polymer further containing a repeating unit having another structure. The repeating unit having the structure represented by the general formula (1)

or the general formula (1') contained in the polymer may be only one kind or two or more kinds. Examples of the repeating unit that does not have the structure represented by the general formula (1) or the general formula (1') include a repeating unit derived from a monomer that is used for ordinary copolymerization. Examples of the repeating unit include a repeating unit derived from a monomer having an ethylenic unsaturated bond, such as ethylene and styrene.

Organic Light-Emitting Device

The compound represented by the general formula (1) of the invention is useful as a light-emitting material of an organic light-emitting device. Accordingly, the compound represented by the general formula (1) of the invention may be effectively used as a light-emitting material in a light-emitting layer of an organic light-emitting device. The compound represented by the general formula (1) may also be used as a host or assist dopant.

The compound represented by the general formula (1) includes a delayed fluorescent material emitting delayed fluorescent light. Therefore, the invention provides an invention relating to a delayed fluorescent material having a structure represented by the general formula (1), an invention relating to use of the compound represented by the general formula (1) as a delayed fluorescent material, and an invention relating to a method for emitting delayed fluorescent light with the compound represented by the general formula (1). An organic light-emitting device that uses the compound as a light-emitting material has features that the device emits delayed fluorescent light and has a high light emission efficiency. The principle of the features may be described as follows for an organic electroluminescent device as an example.

In an organic electroluminescent device, carriers are injected from both an anode and a cathode to a light-emitting material to form an excited state for the light-emitting material, with which light is emitted. In the case of a carrier injection type organic electroluminescent device, in general, excitons that are excited to the excited singlet state are 25% of the total excitons generated, and the remaining 75% thereof are excited to the excited triplet state. Accordingly, the use of phosphorescence, which is light emission from the excited triplet state, provides a high energy use efficiency. However, the excited triplet state has a long lifetime and thus causes saturation of the excited state and deactivation of energy through mutual action with the excitons in the excited triplet state, and therefore the quantum yield of phosphorescence may generally be often not high. On the other hand, a delayed fluorescent material emits fluorescent light through the mechanism that the energy of excitons transits to the excited triplet state through intersystem crossing or the like, and then transits to the excited singlet state through reverse intersystem crossing due to triplet-triplet annihilation or absorption of thermal energy, thereby emitting fluorescent light. It is considered that a thermal activation type delayed fluorescent material emitting light through absorption of thermal energy is particularly useful for an organic electroluminescent device. In the case where a delayed fluorescent material is used in an organic electroluminescent device, the excitons in the excited singlet state normally emit fluorescent light. On the other hand, the excitons in the excited triplet state emit fluorescent light through intersystem crossing to the excited singlet state by absorbing the heat generated by the device. At this time, the light emitted through reverse intersystem crossing from the excited triplet state to the excited singlet state has the same wavelength as fluorescent light since it is light emission from the excited singlet state, but has a longer lifetime (light emission lifetime) than the normal fluorescent light and phosphorescent light, and thus the light is observed as fluorescent light that is delayed from the normal fluorescent light and phosphorescent light. The light may be defined as delayed fluorescent light. The use of the thermal activation type exciton transition mechanism may raise the proportion of the compound in the excited singlet state, which is generally formed in a proportion only of 25%, to 25% or more through the absorption of the thermal energy after the carrier injection. A compound that emits strong fluorescent light and delayed fluorescent light at a low temperature of lower than 100° C. undergoes the intersystem crossing from the excited triplet state to the excited singlet state sufficiently with the heat of the device, thereby emitting delayed fluorescent light, and thus the use of the compound may drastically enhance the light emission efficiency.

The use of the compound represented by the general formula (1) of the invention as a light-emitting material of a light-emitting layer may provide an excellent organic light-emitting device, such as an organic photoluminescent device (organic PL device) and an organic electroluminescent device (organic EL device). The organic photoluminescent device has a structure containing a substrate having formed thereon at least a light-emitting layer. The organic electroluminescent device has a structure containing at least an anode, a cathode, and an organic layer formed between the anode and the cathode. The organic layer contains at least a light-emitting layer, and may be formed only of a light-emitting layer, or may have one or more organic layer in addition to the light-emitting layer. Examples of the organic layer include a hole transporting layer, a hole injection layer, an electron barrier layer, a hole barrier layer, an electron injection layer, an electron transporting layer, and an exciton barrier layer. The hole transporting layer may be a hole injection and transporting layer having a hole injection function, and the electron transporting layer may be an electron injection and transporting layer having an electron injection function. A specific structural example of an organic electroluminescent device is shown in FIG. 1. In FIG. 1, the numeral 1 denotes a substrate, 2 denotes an anode, 3 denotes a hole injection layer, 4 denotes a hole transporting layer, 5 denotes a light-emitting layer, 6 denotes an electron transporting layer, and 7 denotes a cathode.

The members and the layers of the organic electroluminescent device will be described below. The descriptions for the substrate and the light-emitting layer may also be applied to the substrate and the light-emitting layer of the organic photoluminescent device.

Substrate

The organic electroluminescent device of the invention is preferably supported by a substrate. The substrate is not particularly limited and may be one that has been commonly used in an organic electroluminescent device, and examples thereof used include those formed of glass, transparent plastics, quartz and silicon.

Anode

The anode of the organic electroluminescent device used is preferably formed of, as an electrode material, a metal, an alloy, or an electroconductive compound each having a large work function (4 eV or more), or a mixture thereof. Specific examples of the electrode material include a metal, such as Au, and an electroconductive transparent material, such as CuI, indium tin oxide (ITO), $SnO_2$ and ZnO. A material that is amorphous and is capable of forming a transparent electroconductive film, such as IDIXO ($In_2O_3$—ZnO), may also be used. The anode may be formed in such a manner that the electrode material is formed into a thin film by such a method as vapor deposition or sputtering, and the film is patterned into a desired pattern by a photolithography method, or in the case where the pattern may not require high accuracy (for example, approximately 100 µm or more), the pattern may be formed with a mask having a desired shape on vapor deposition or sputtering of the electrode material. In alternative, in the case where a material capable of being coated, such as an organic electroconductive compound, is used, a wet film forming method, such as a printing method and a coating method, may be used. In the case where emitted light is to be taken out through the anode, the anode preferably has a transmittance of more than 10%, and the anode preferably has a sheet resistance of several hundred ohm per square or less. The thickness of the anode may be generally selected from a range of from 10 to 1,000 nm, and preferably from 10 to 200 nm, while depending on the material used.

Cathode

The cathode is preferably formed of as an electrode material a metal (which is referred to as an electron injection metal), an alloy, or an electroconductive compound, having a small work function (4 eV or less), or a mixture thereof. Specific examples of the electrode material include sodium, a sodium-potassium alloy, magnesium, lithium, a magnesium-cupper mixture, a magnesium-silver mixture, a magnesium-aluminum mixture, a magnesium-indium mixture, an aluminum-aluminum oxide ($Al_2O_3$) mixture, indium, a lithium-aluminum mixture, and a rare earth metal. Among these, a mixture of an electron injection metal and a second metal that is a stable metal having a larger work function than the electron injection metal, for example, a magnesium-silver mixture, a magnesium-aluminum mixture, a magnesium-indium mixture, an aluminum-aluminum oxide ($Al_2O_3$) mixture, a lithium-aluminum mixture, and aluminum, is preferred from the standpoint of the electron injection property and the durability against oxidation and the like. The cathode may be produced by forming the electrode material into a thin film by such a method as vapor deposition or sputtering. The cathode preferably has a sheet resistance of several hundred ohm per square or less, and the thickness thereof may be generally selected from a range of from 10 nm to 5 µm, and preferably from 50 to 200 nm. For transmitting the emitted light, any one of the anode and the cathode of the organic electroluminescent device is preferably transparent or translucent, thereby enhancing the light emission luminance.

The cathode may be formed with the electroconductive transparent materials described for the anode, thereby forming a transparent or translucent cathode, and by applying the cathode, a device having an anode and a cathode, both of which have transmittance, may be produced.

Light-Emitting Layer

The light-emitting layer is a layer, in which holes and electrons injected from the anode and the cathode respectively are recombined to form excitons, and then the layer emits light. A light-emitting material may be solely used as the light-emitting layer, but the light-emitting layer preferably contains a light-emitting material and a host material. The light-emitting material used may be one kind or two or more kinds selected from the group of compounds represented by the general formula (1) of the invention. In order that the organic electroluminescent device and the organic photoluminescent device of the invention exhibit a high light emission efficiency, it is important that the singlet excitons and the triplet excitons generated in the light-emitting material are confined in the light-emitting material. Accordingly, a host material is preferably used in addition to the light-emitting material in the light-emitting layer. The host material used may be an organic compound that has excited singlet energy and excited triplet energy, at least one of which is higher than those of the light-emitting material of the invention. As a result, the singlet excitons and the triplet excitons generated in the light-emitting material of the invention are capable of being confined in the molecules of the light-emitting material of the invention, thereby eliciting the light emission efficiency thereof sufficiently. Even though the singlet excitons and the triplet excitons are not confined sufficiently, a high light emission efficiency may be obtained in some cases, and thus a host material that is capable of achieving a high light emission efficiency may be used in the invention without any particular limitation. In the organic light-emitting device and the organic electroluminescent device of the invention, the light emission occurs in the light-emitting material of the invention contained in the light-emitting layer. The emitted light contains both fluorescent light and delayed fluorescent light. However, a part of the emitted light may contain emitted light from the host material, or the emitted light may partially contain emitted light from the host material.

In the case where the host material is used, the amount of the compound of the invention as the light-emitting material contained in the light-emitting layer is preferably 0.1% by weight or more, and more preferably 1% by weight or more, and is preferably 50% by weight or less, more preferably 20% by weight or less, and further preferably 10% by weight or less.

The host material in the light-emitting layer is preferably an organic compound that has a hole transporting capability and an electron transporting capability, prevents the emitted light from being increased in wavelength, and has a high glass transition temperature.

Injection Layer

The injection layer is a layer that is provided between the electrode and the organic layer, for decreasing the driving voltage and enhancing the light emission luminance, and includes a hole injection layer and an electron injection layer, which may be provided between the anode and the light-emitting layer or the hole transporting layer and between the cathode and the light-emitting layer or the electron transporting layer. The injection layer may be provided depending on necessity.

Barrier Layer

The barrier layer is a layer that is capable of inhibiting charges (electrons or holes) and/or excitons present in the light-emitting layer from being diffused outside the light-emitting layer. The electron barrier layer may be disposed between the light-emitting layer and the hole transporting layer, and inhibits electrons from passing through the light-emitting layer toward the hole transporting layer. Similarly, the hole barrier layer may be disposed between the light-emitting layer and the electron transporting layer, and inhibits holes from passing through the light-emitting layer toward the electron transporting layer. The barrier layer may also be used for inhibiting excitons from being diffused outside the light-emitting layer. Accordingly, the electron barrier layer and the hole barrier layer each may also have a function as an exciton barrier layer. The electron barrier layer or the exciton barrier layer referred in the description herein is intended to include a layer that has both the functions of an electron barrier layer and an exciton barrier layer by one layer.

Hole Barrier Layer

The hole barrier layer has the function of an electron transporting layer in a broad sense. The hole barrier layer has a function of inhibiting holes from reaching the electron transporting layer while transporting electrons, and thereby enhances the recombination probability of electrons and holes in the light-emitting layer. As the material for the hole barrier layer, the materials for the electron transporting layer described later may be used depending on necessity.

Electron Barrier Layer

The electron barrier layer has the function of transporting holes in a broad sense. The electron barrier layer has a function of inhibiting electrons from reaching the hole transporting layer while transporting holes, and thereby enhances the recombination probability of electrons and holes in the light-emitting layer.

Exciton Barrier Layer

The exciton barrier layer is a layer for inhibiting excitons generated through the recombination of holes and electrons in the light-emitting layer from being diffused to the charge transporting layer, and the use of the layer inserted enables effective confinement of excitons in the light-emitting layer, and thereby enhances the light emission efficiency of the device. The exciton barrier layer may be inserted adjacent to the light-emitting layer on any of the side of the anode and the side of the cathode, and on both the sides. Specifically, in the case where the exciton barrier layer is present on the side of the anode, the layer may be inserted between the hole transporting layer and the light-emitting layer and adjacent to the light-emitting layer, and in the case where the layer is inserted on the side of the cathode, the layer may be inserted between the light-emitting layer and the cathode and adjacent to the light-emitting layer. Between the anode and the exciton barrier layer that is adjacent to the light-emitting layer on the side of the anode, a hole injection layer, an electron barrier layer, and the like may be provided, and between the cathode and the exciton barrier layer that is adjacent to the light-emitting layer on the side of the cathode, an electron injection layer, an electron transporting layer, a hole barrier layer, and the like may be provided. In the case where the barrier layer is provided, the material used for the barrier layer preferably has excited singlet energy and excited triplet energy, at least one of which is higher than the excited singlet energy and the excited triplet energy of the light-emitting layer, respectively.

Hole Transporting Layer

The hole transporting layer is formed of a hole transporting material having a function of transporting holes, and the hole transporting layer may be provided as a single layer or plural layers.

The hole transporting material has one of injection or transporting property of holes and barrier property of electrons, and may be any of an organic material and an inorganic material. Examples of known hole transporting materials that can be used herein include a triazole derivative, an oxadiazole derivative, an imidazole derivative, a carbazole derivative, an indolocarbazole derivative, a polyarylalkane derivative, a pyrazoline derivative, a pyrazolone derivative, a phenylenediamine derivative, an arylamine derivative, an amino-substituted chalcone derivative, an oxazole derivative, a styrylanthracene derivative, a fluorenone derivative, a hydrazone derivative, a stilbene derivative, a silazane derivative, an aniline copolymer, and an electroconductive polymer oligomer, particularly a thiophene oligomer. Among these, a porphyrin compound, an aromatic tertiary amine compound, and a styrylamine compound are preferably used, and an aromatic tertiary amine compound is more preferably used.

Electron Transporting Layer

The electron transporting layer is formed of a material having a function of transporting electrons, and the electron transporting layer may be provided as a single layer or plural layers.

The electron transporting material (which may also function as a hole barrier material in some cases) suffices to have a function of transporting electrons, which are injected from the cathode, to the light-emitting layer. Examples of the electron transporting layer that may be used herein include a nitro-substituted fluorene derivative, a diphenylquinone derivative, a thiopyran dioxide derivative, carbodiimide, a fluorenylidene methane derivative, anthraquinodimethane and an anthrone derivative, and an oxadiazole derivative. Further, regarding the aforementioned oxadiazole derivative, the electron transporting material used may be a thiadiazole derivative obtained by replacing the oxygen atom of the oxadiazole ring of the oxadiazole derivative by a sulfur atom, or a quinoxaline derivative having a quinoxaline ring, which is known as an electron attracting group. Furthermore, polymer materials having these materials introduced to the polymer chain or having these materials used as the main chain of the polymer may also be used.

In the production of the organic electroluminescent device, the compound represented by the general formula (1) may be used not only in one layer of an organic layer (for example, an electron transporting layer), but also in plural organic layers. In this case, the compounds represented by the general formula (1) used in the organic layers may be the same as or different from each other. For example, the compound represented by the general formula (1) may be used in the injection layer, the barrier layer, the hole barrier layer, the electron barrier layer, the exciton barrier layer, the hole transporting layer, and the like, in addition to the electron transporting layer and the light-emitting layer. The film forming methods of the layers are not particularly limited, and the layers may be produced by any of a dry process and a wet process.

Specific examples of the preferred materials that may be used in the organic electroluminescent device are shown below, but the materials that may be used in the invention are not construed as being limited to the example compounds below. The compound that is shown as a material having a particular function may also be used as a material having another function. In the following structural formulae of the example compounds, R, R', and $R_1$ to $R_{10}$ each independently represent a hydrogen atom or a substituent, X represents a carbon atom or a hetero atom forming a ring skeleton, n represents an integer of from 3 to 5, Y represents a substituent, and m represents an integer of 0 or more.

Preferred examples of a compound that may also be used as the host material of the light-emitting layer are shown below.

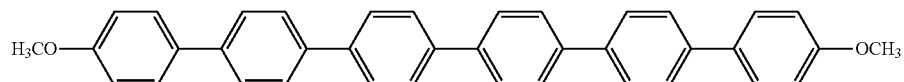
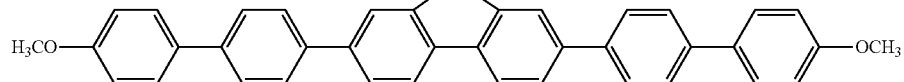
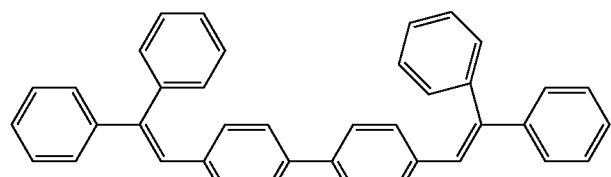
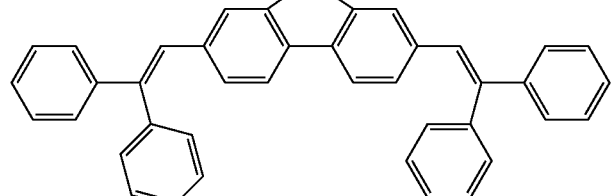
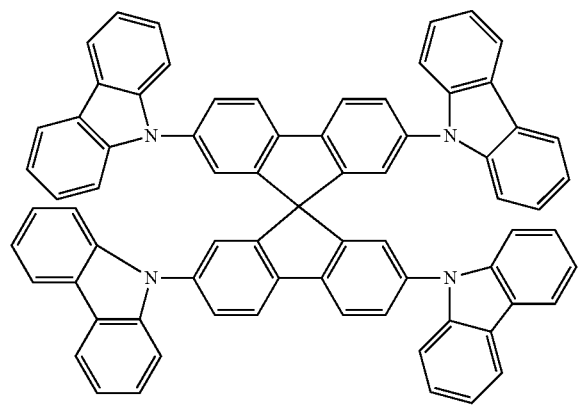
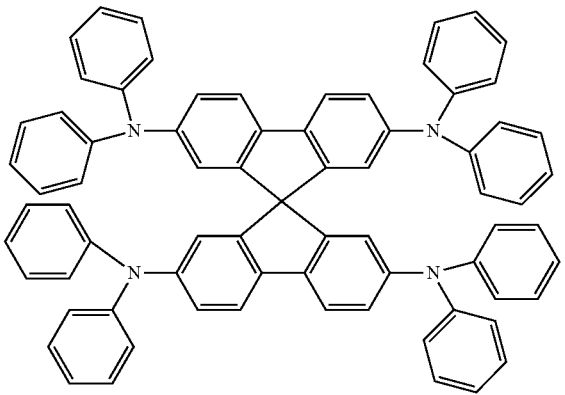
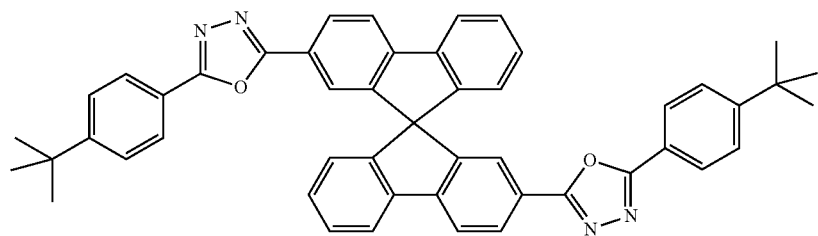

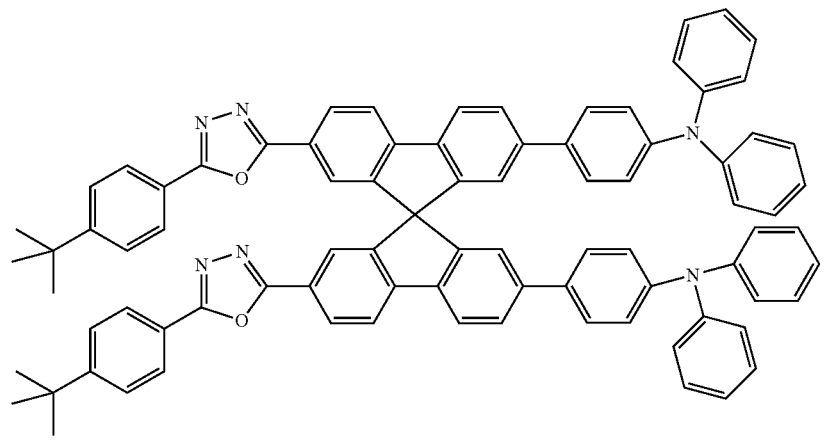
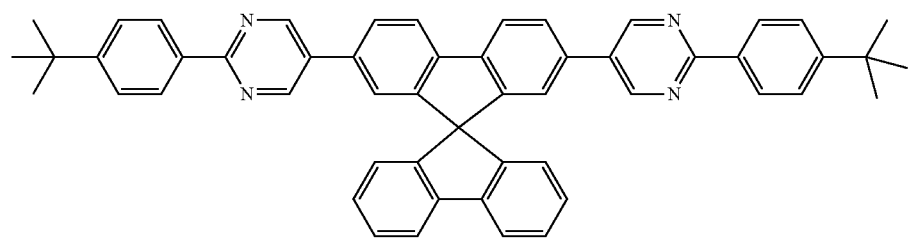
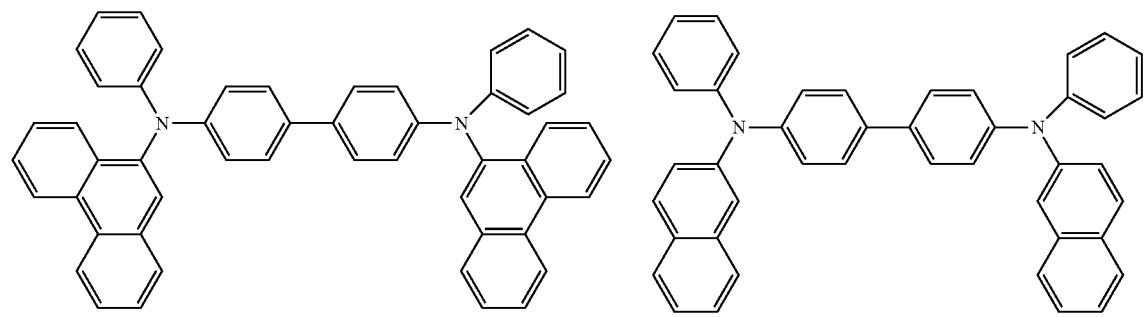
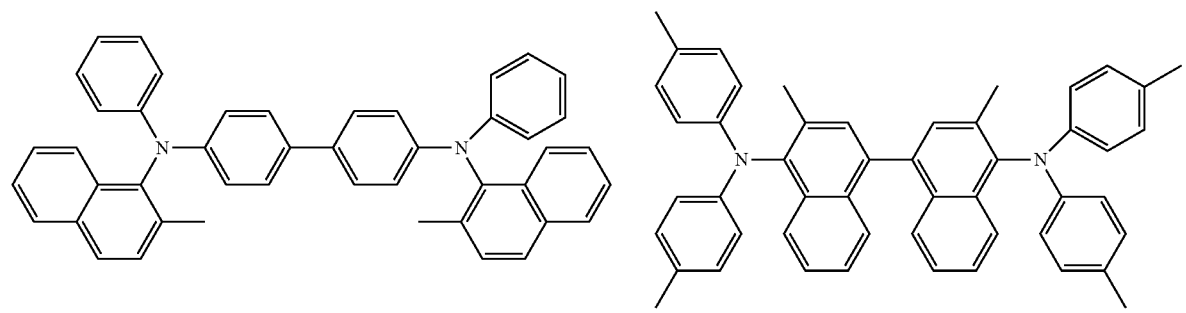

-continued
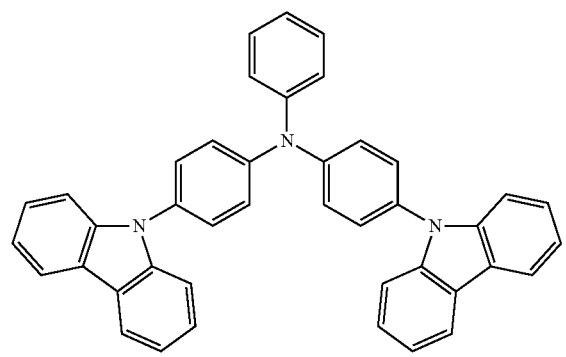
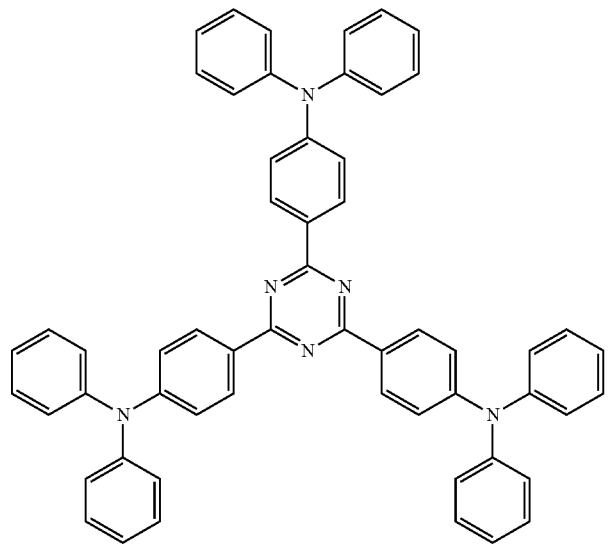
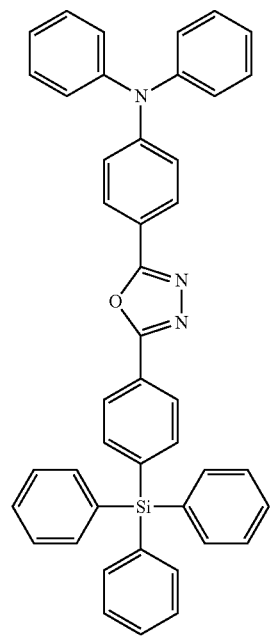
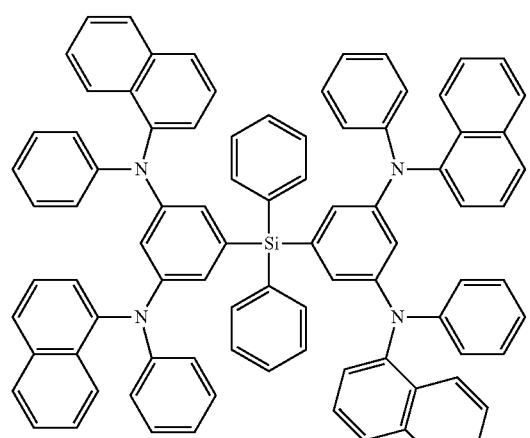
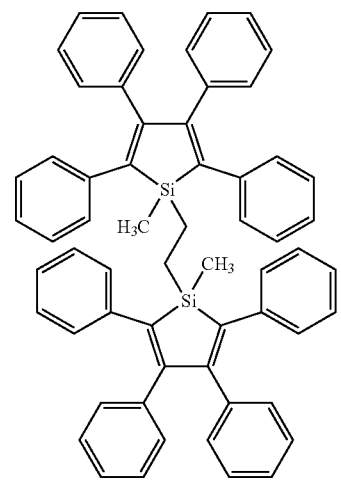
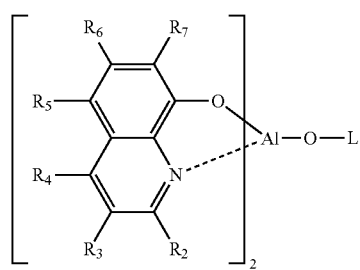
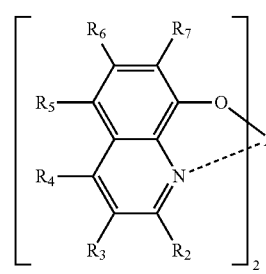
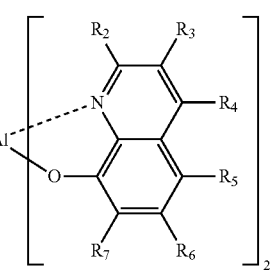
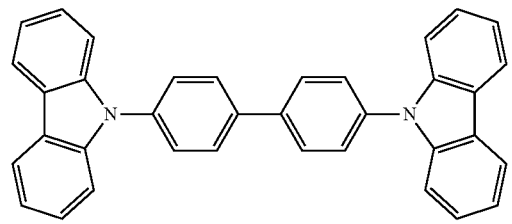
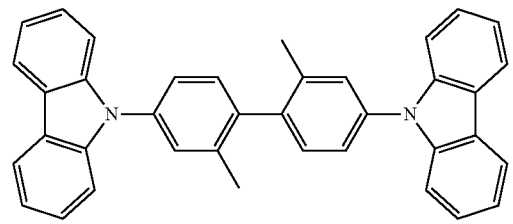

-continued
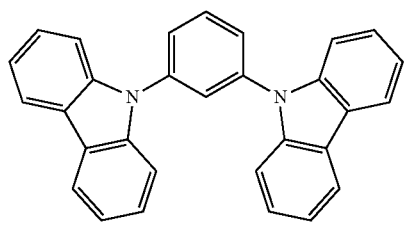
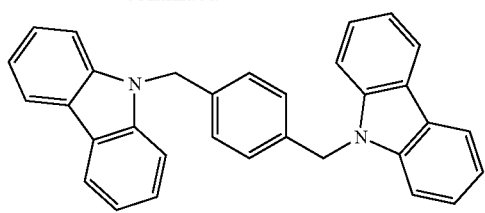
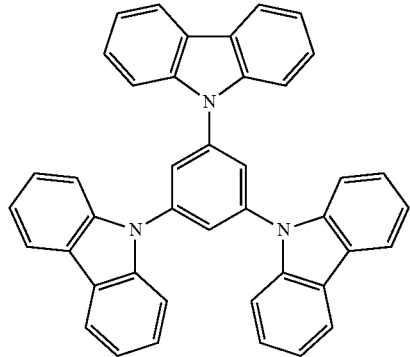
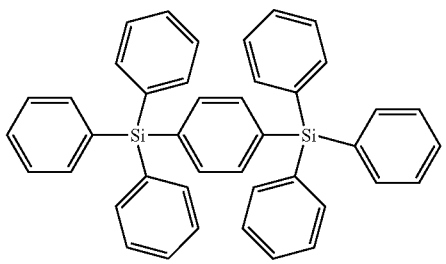
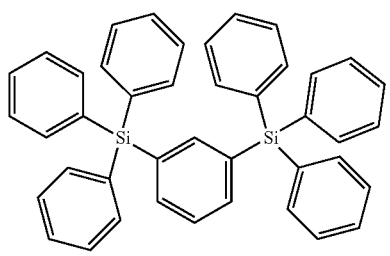
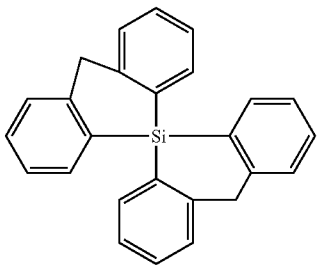
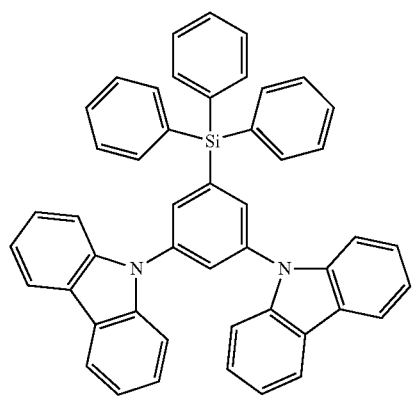
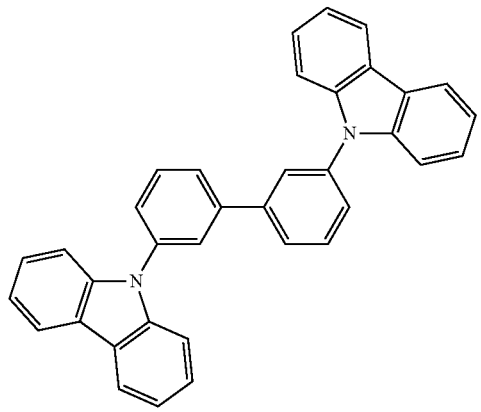
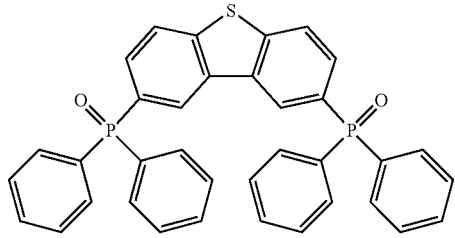
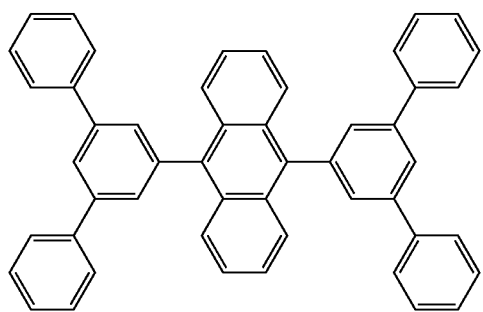
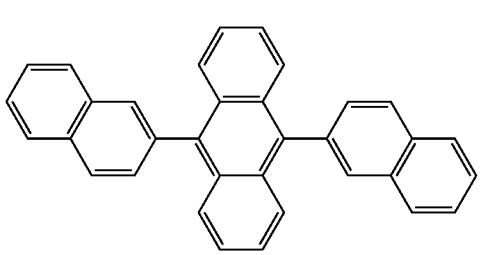

-continued
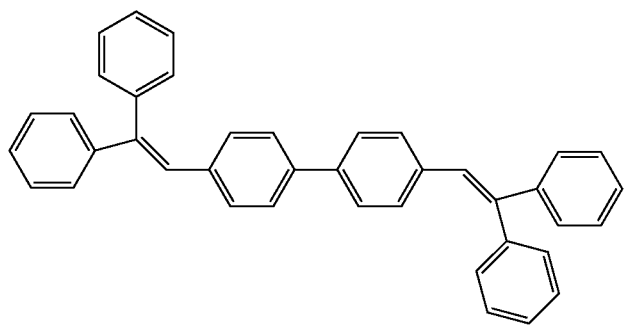
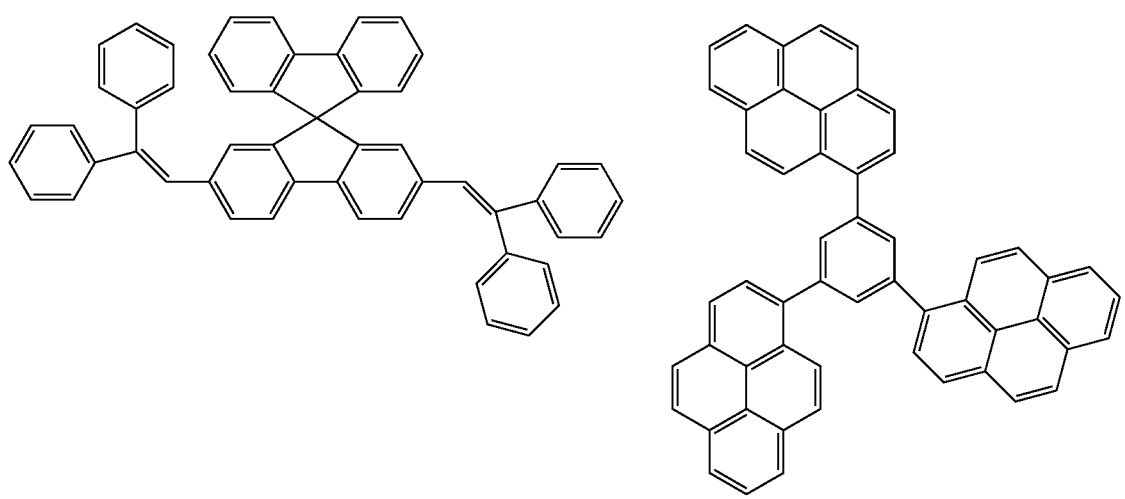
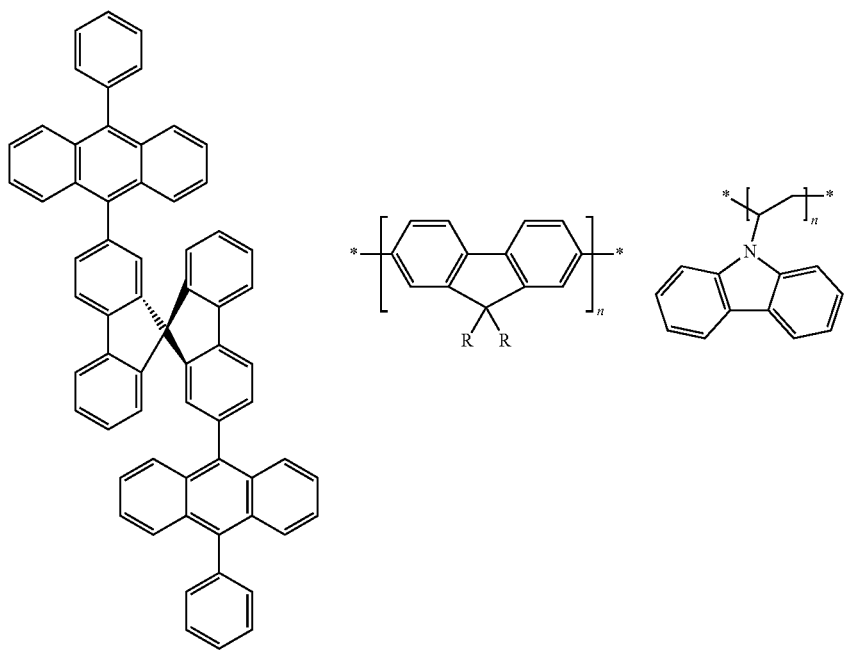

-continued
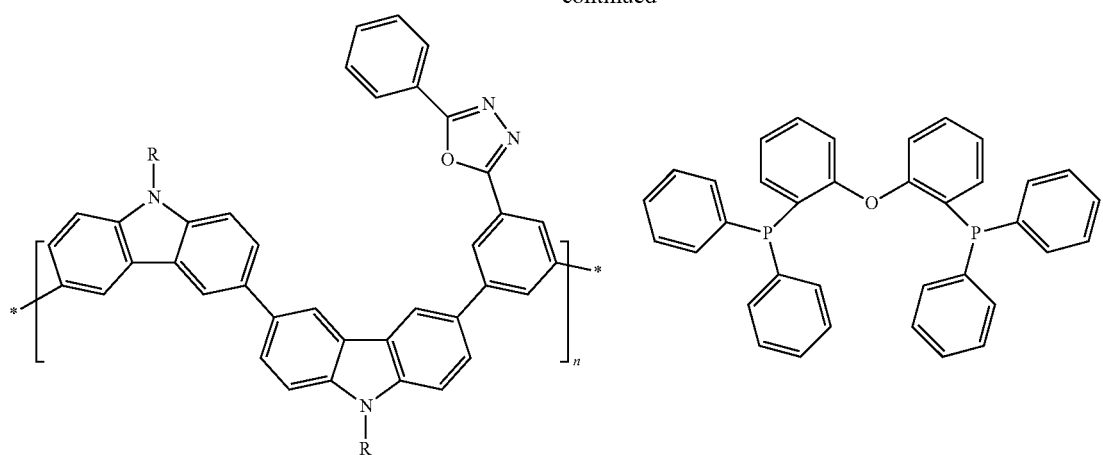
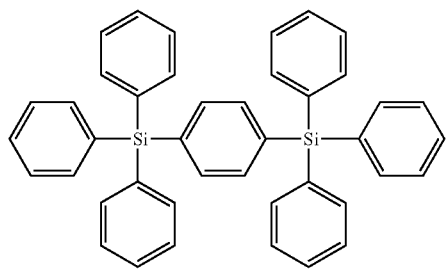
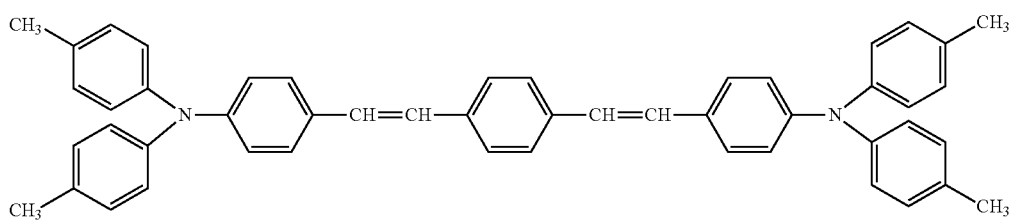
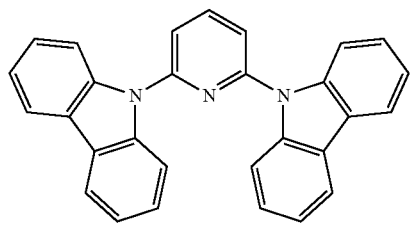

Preferred examples of a compound that may be used as the hole injection material are shown below.
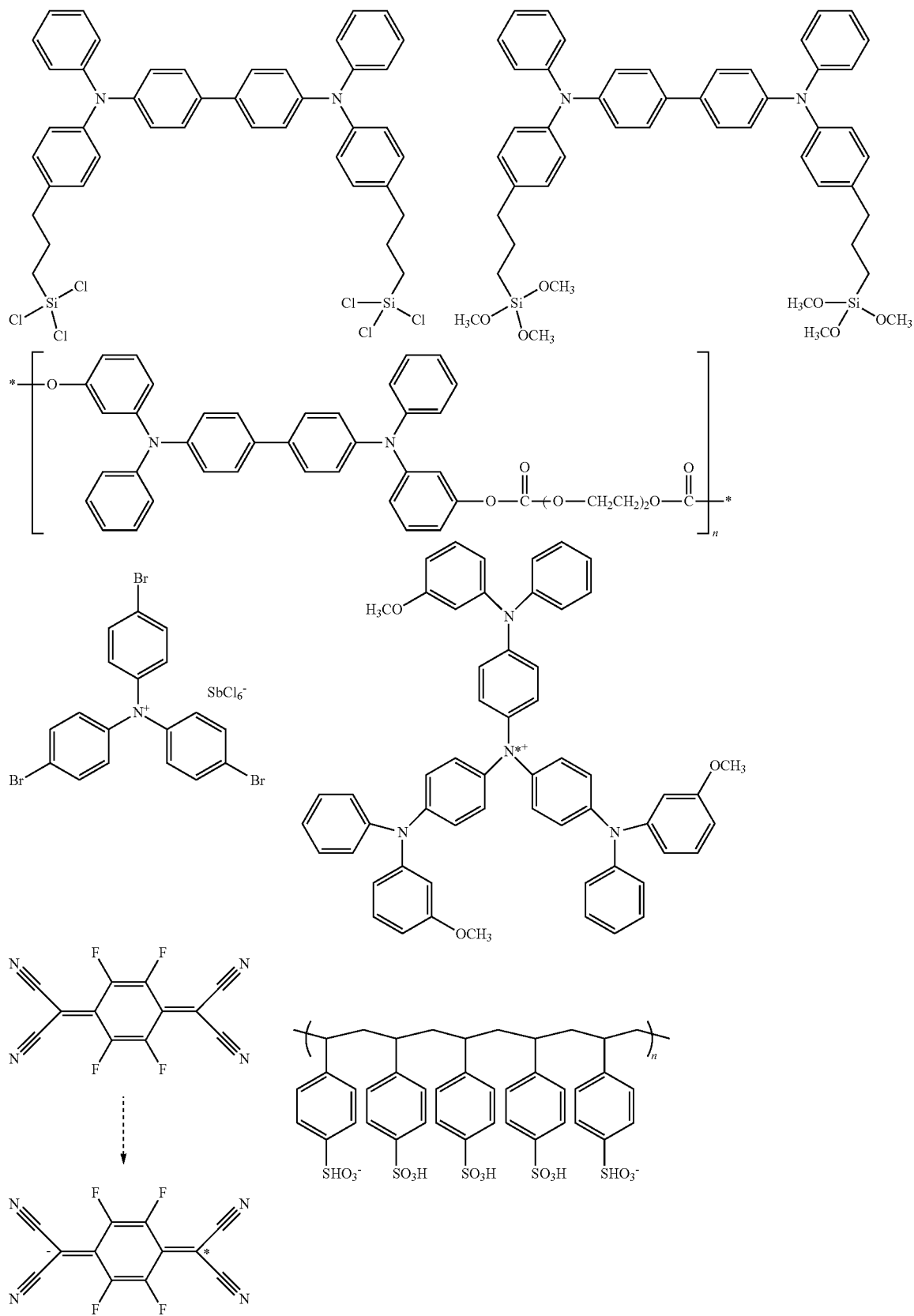

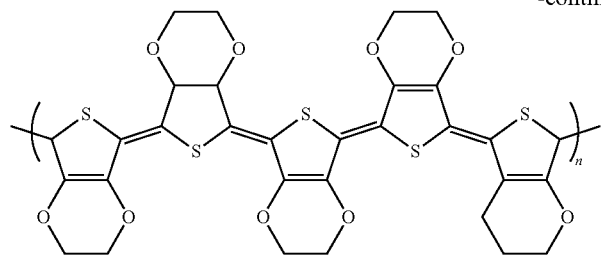
Preferred examples of a compound that may be used as the hole transporting material are shown below.
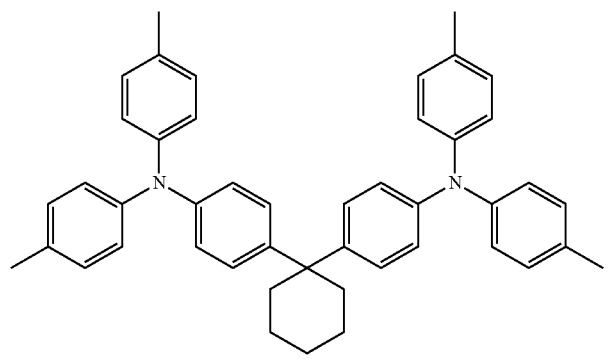
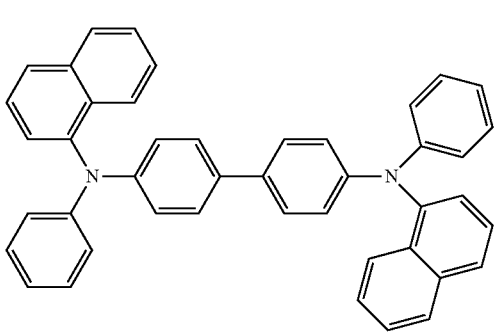
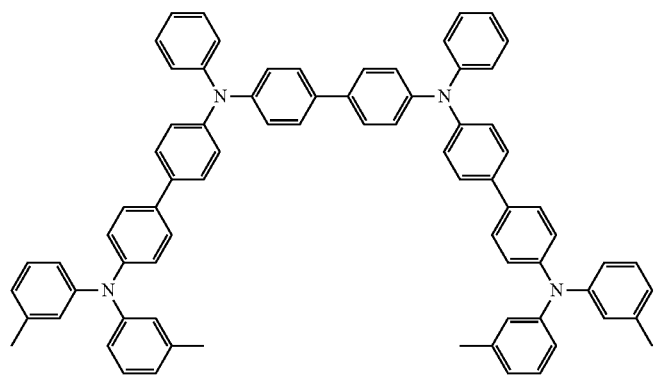
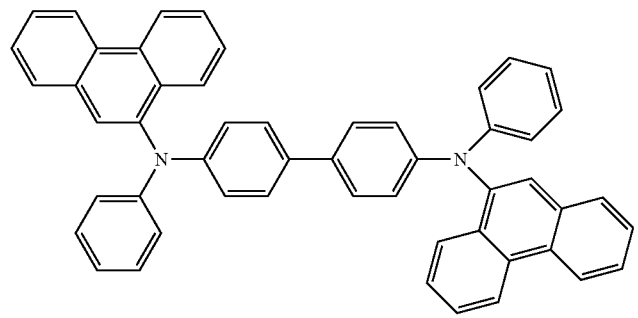
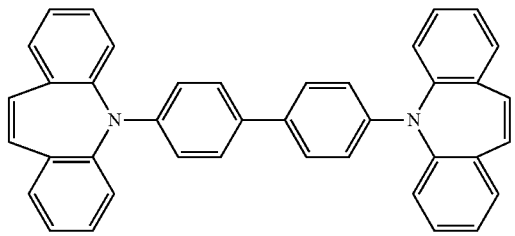

-continued
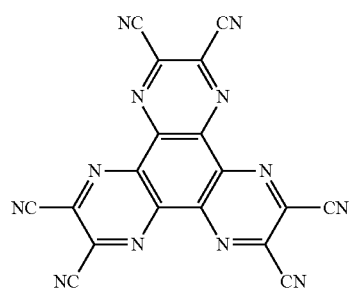
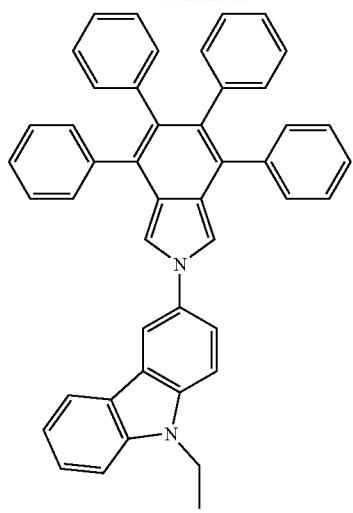
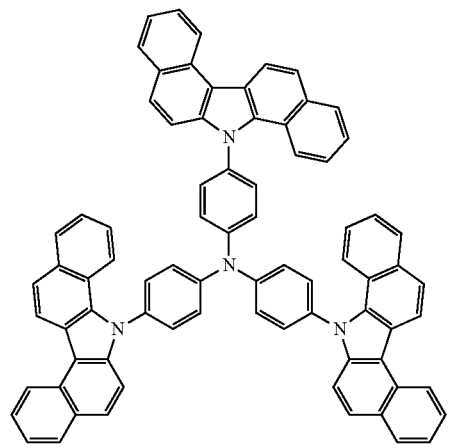
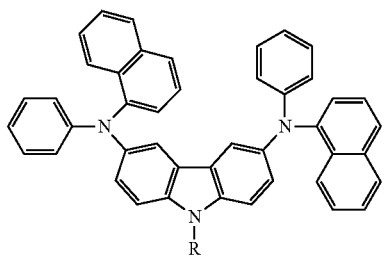
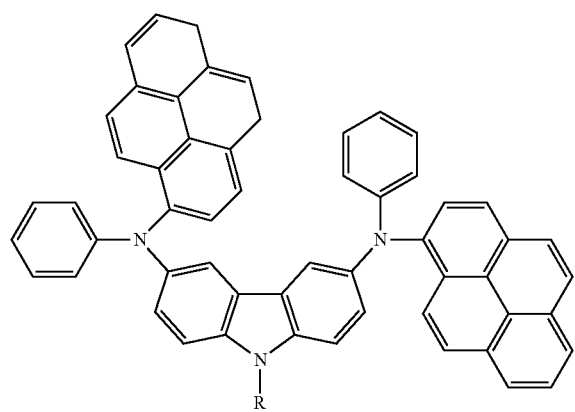

-continued
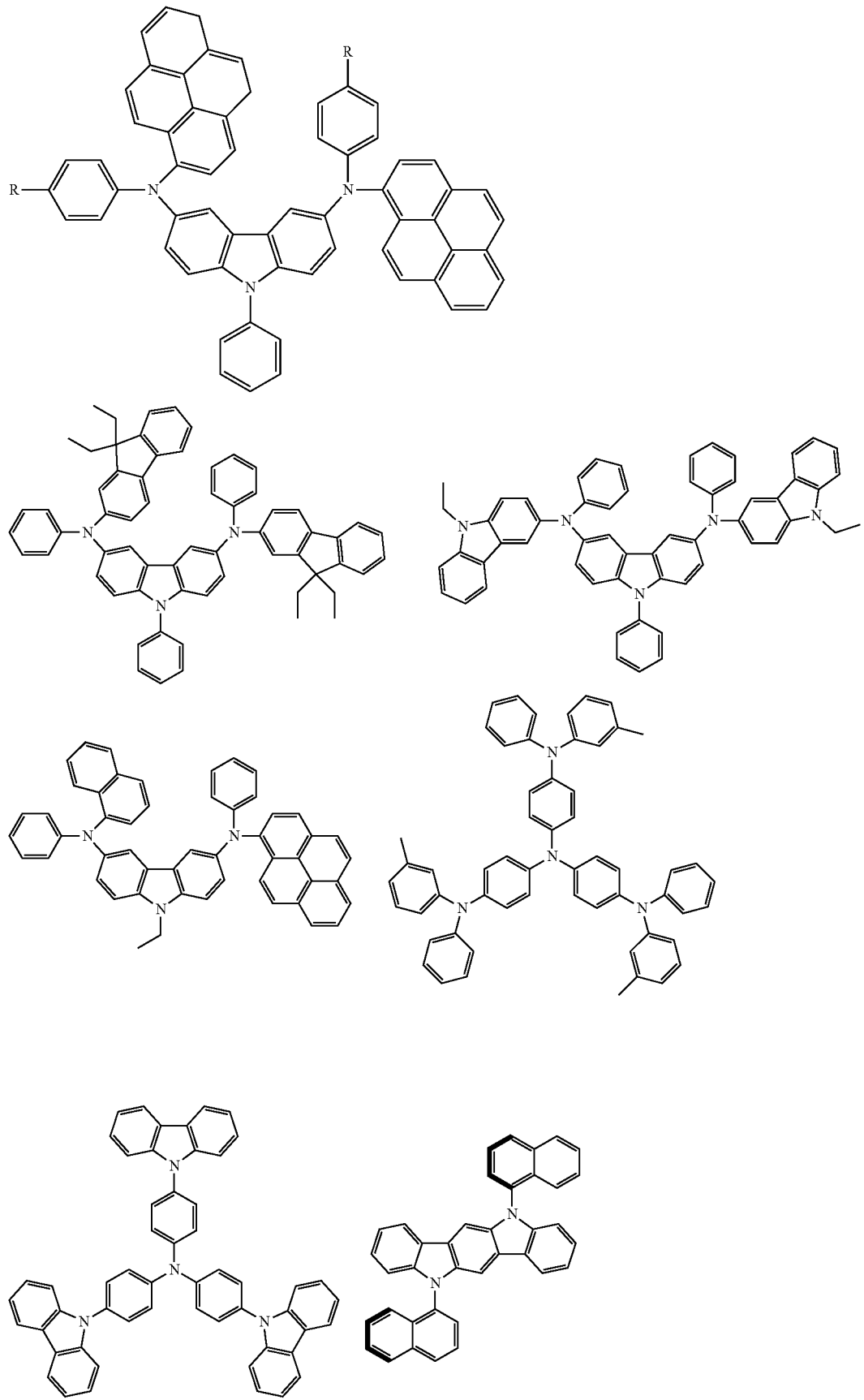

-continued
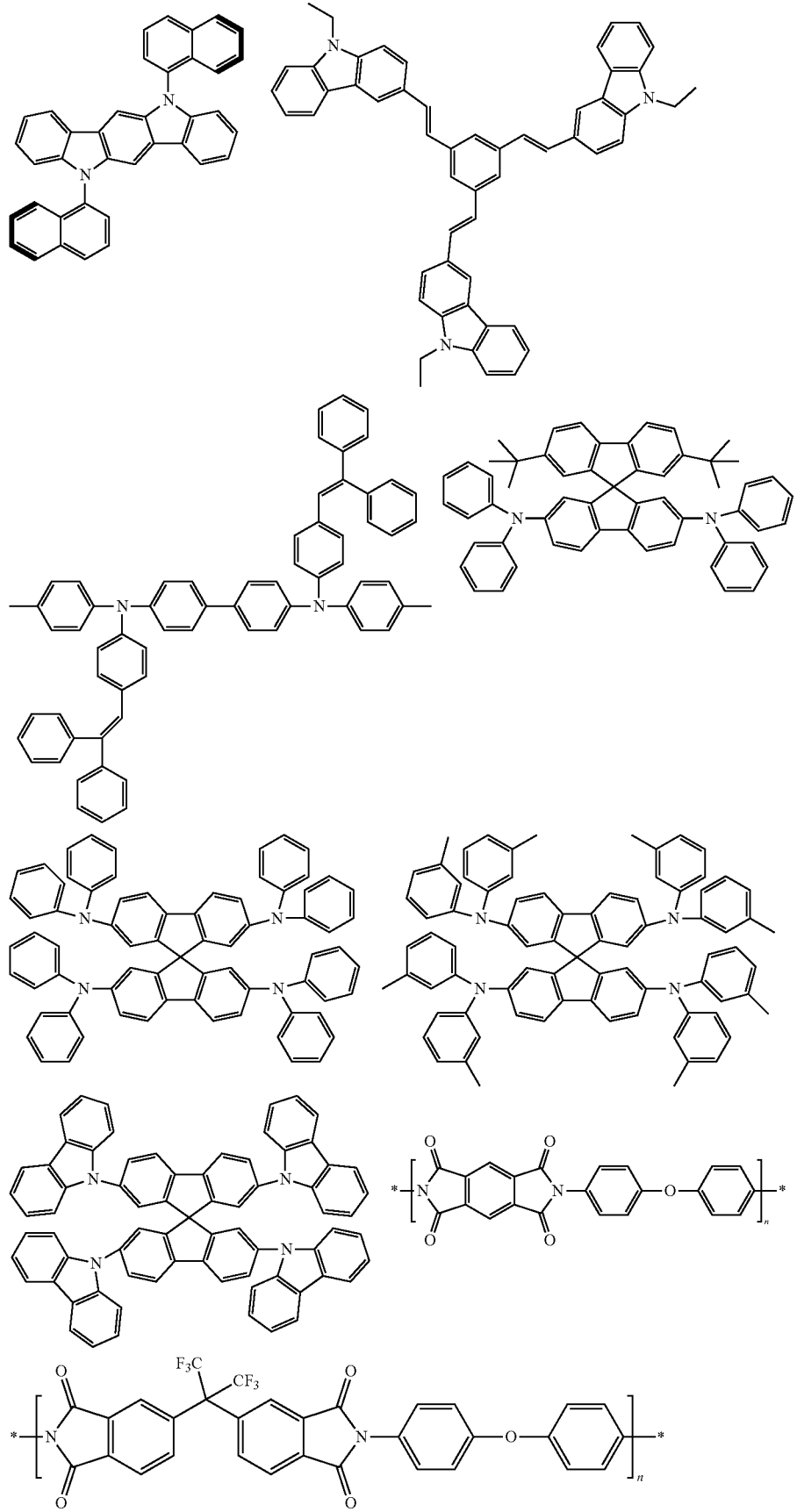

-continued
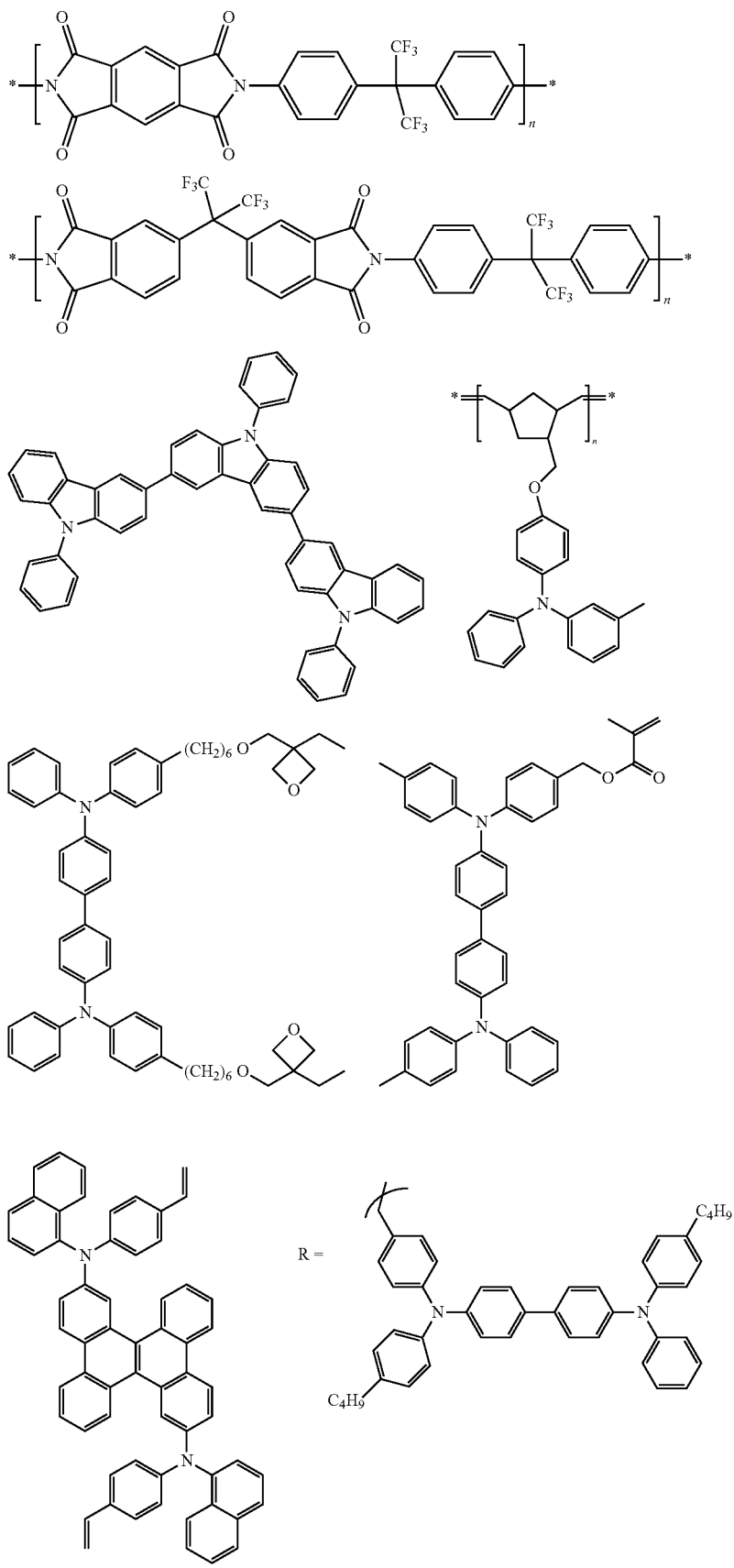

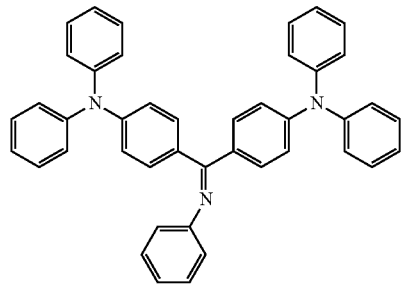
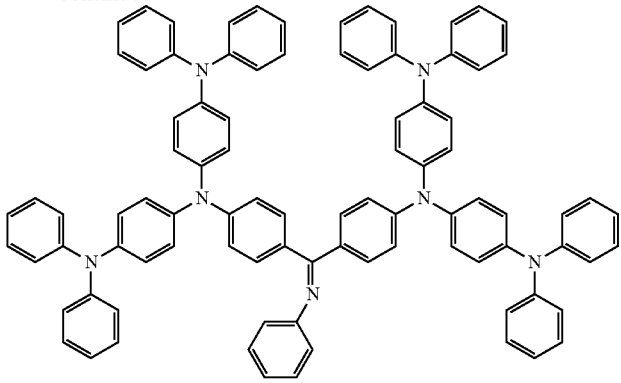
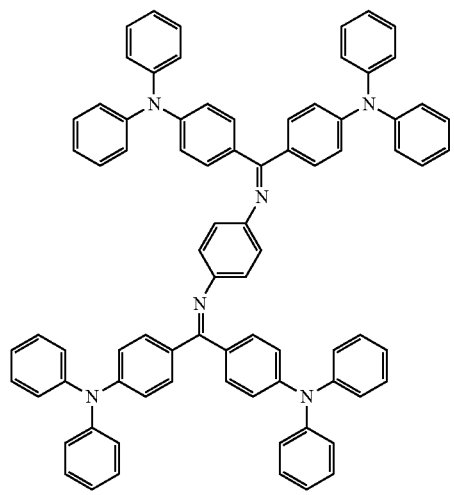
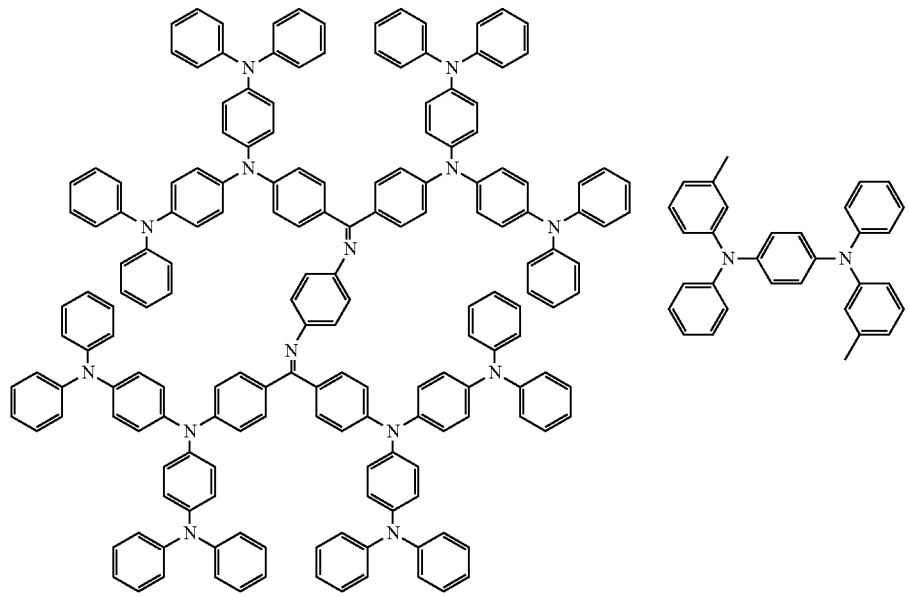

Preferred examples of a compound that may be used as the electron barrier material are shown below.
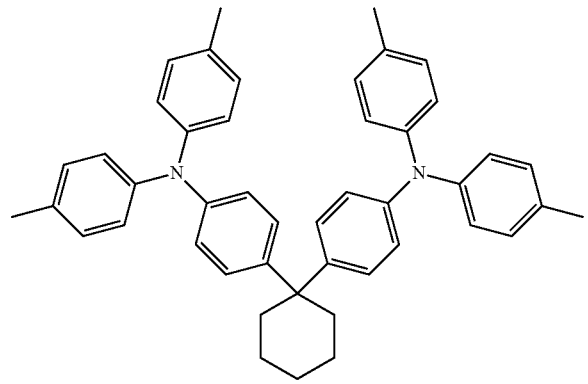
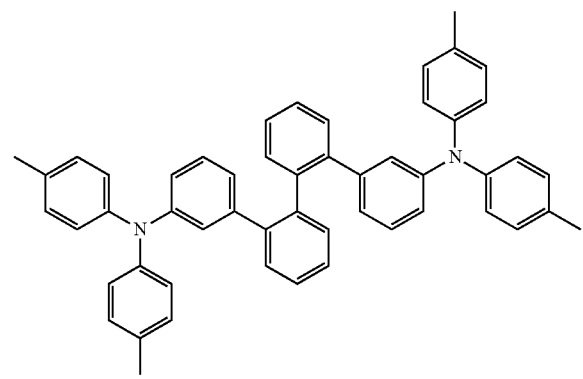
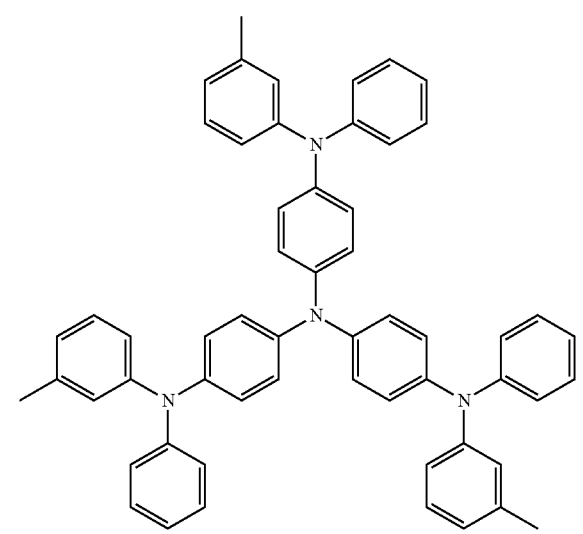
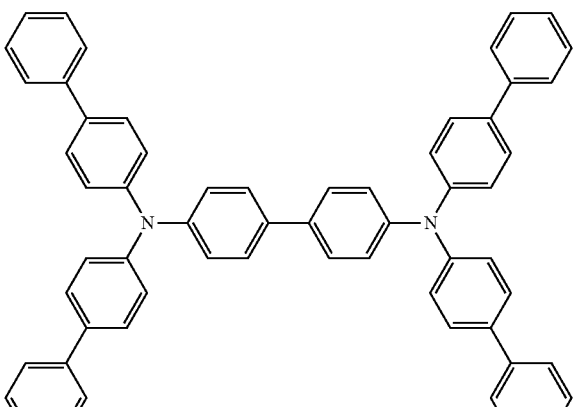
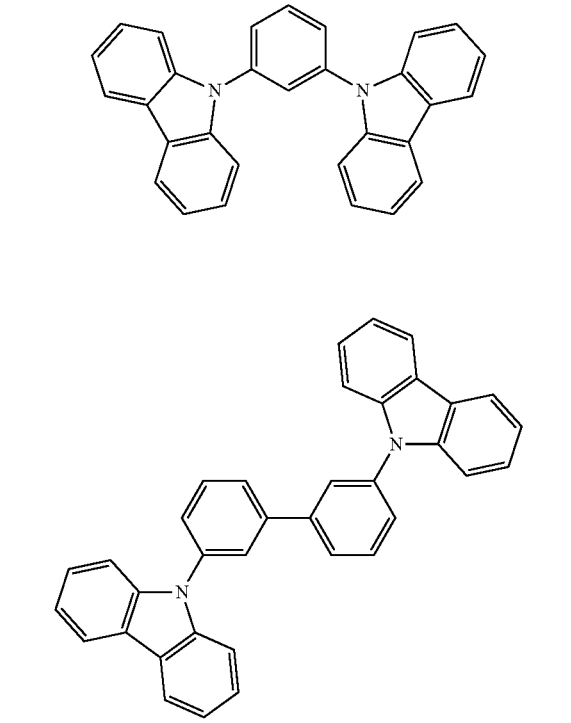
Preferred examples of a compound that may be used as the hole barrier material are shown below.
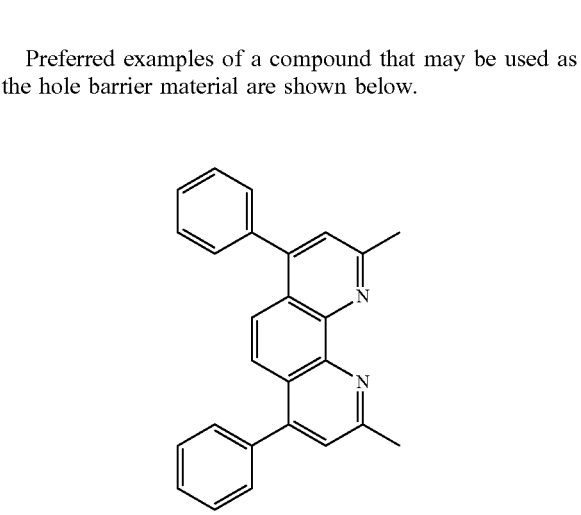

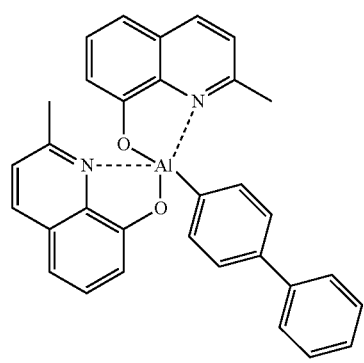
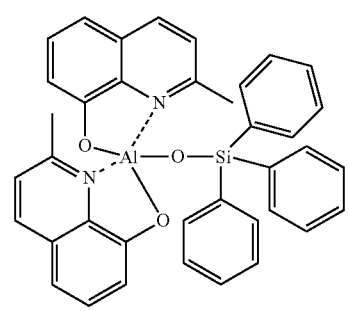
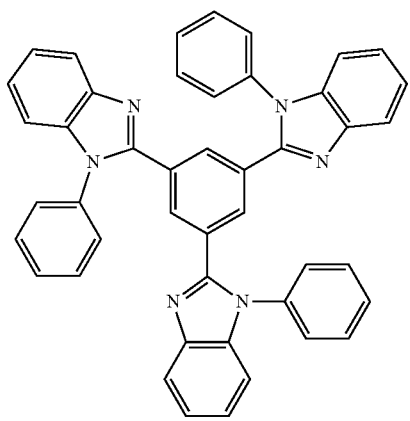
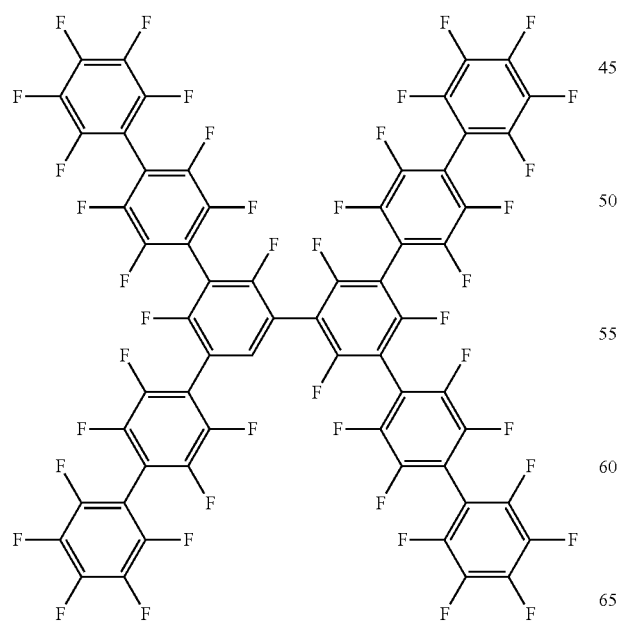
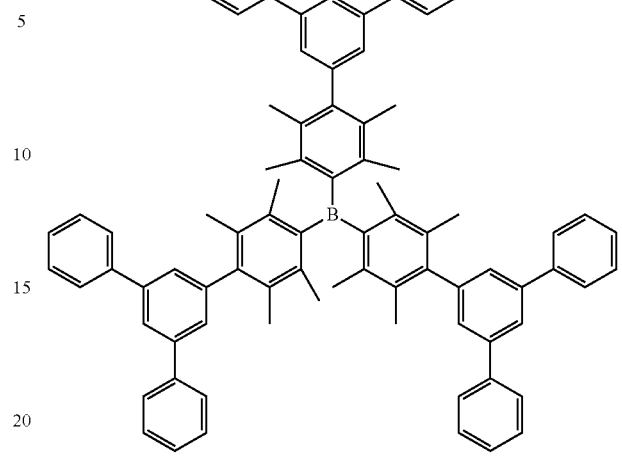
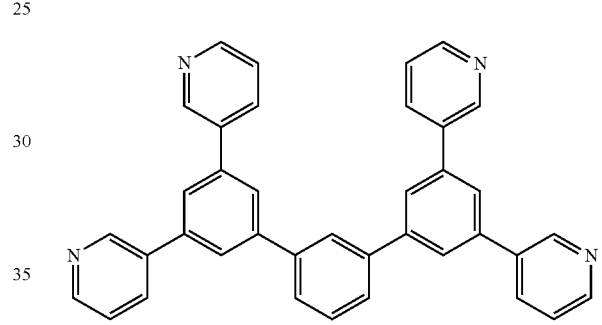
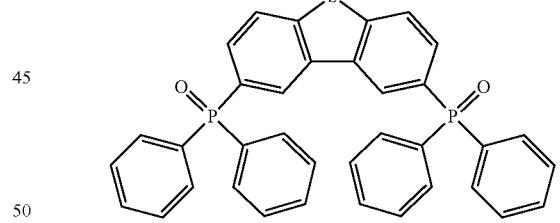
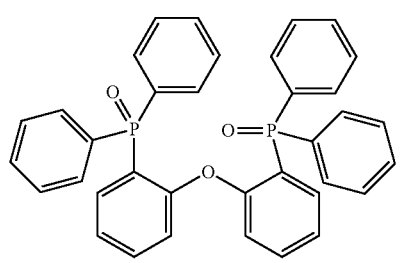

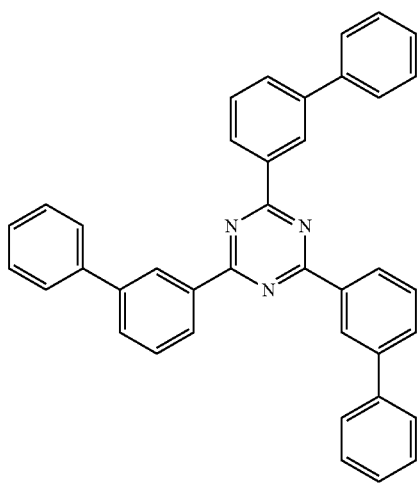
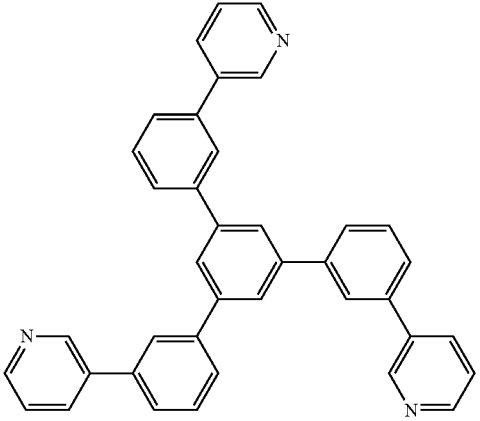
Preferred examples of a compound that may be used as the electron transporting material are shown below.
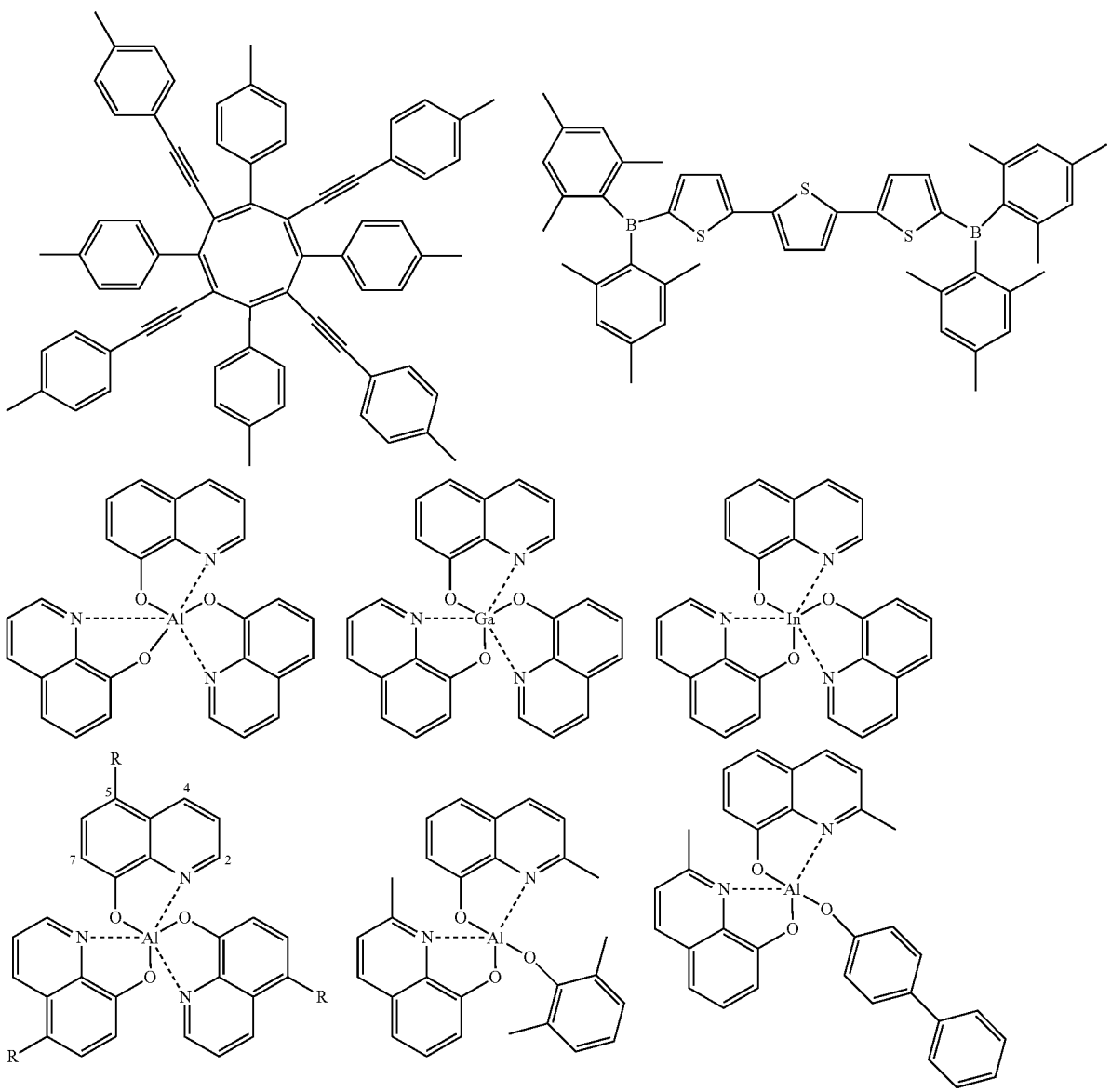

-continued
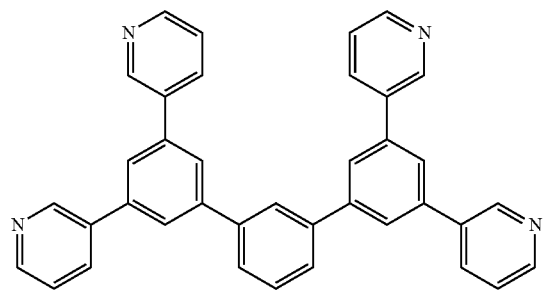
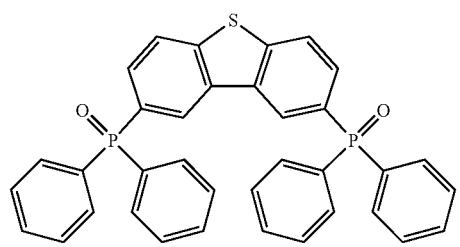
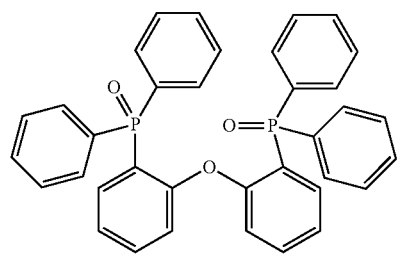
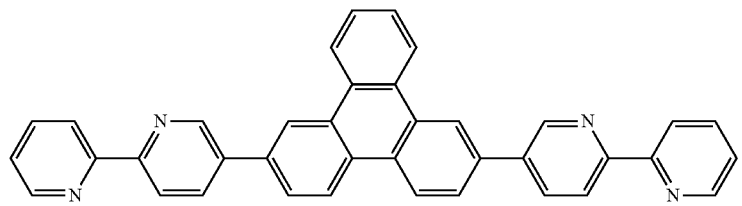
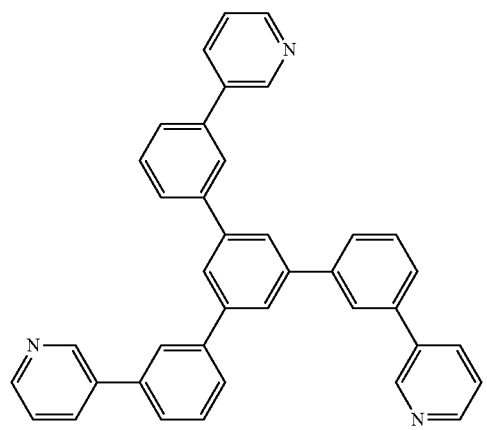
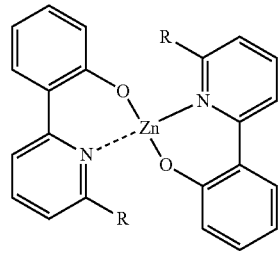
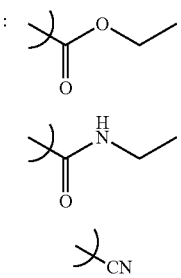
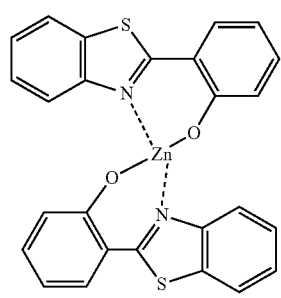
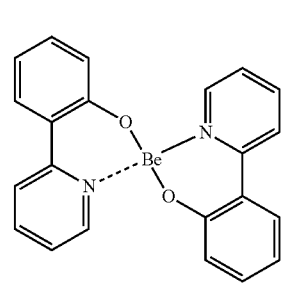
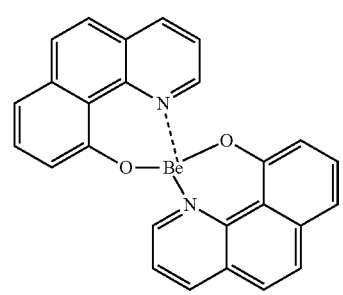
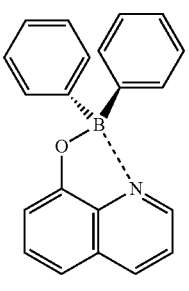

73
74
-continued
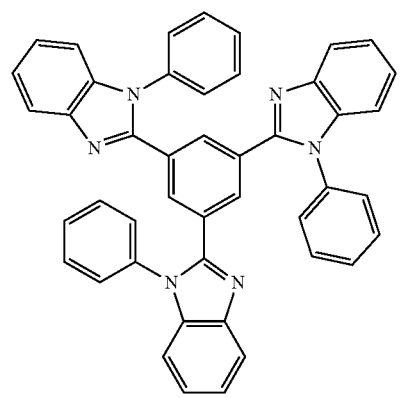
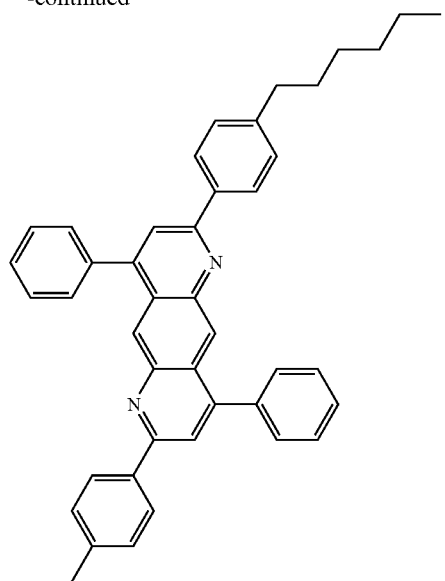
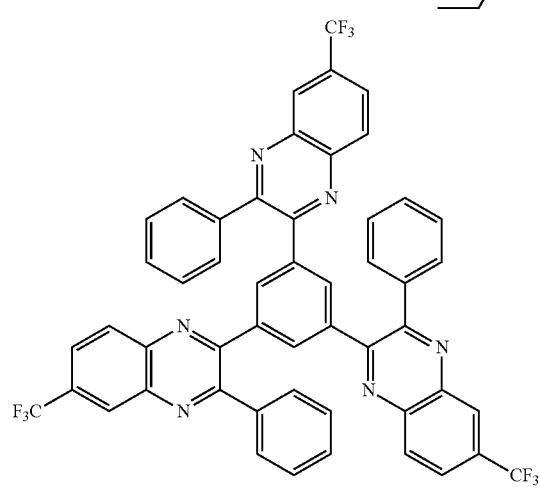
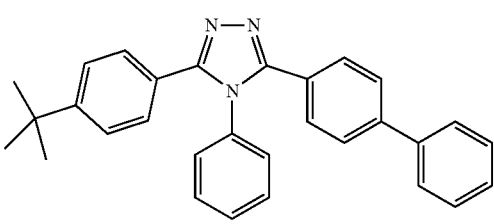
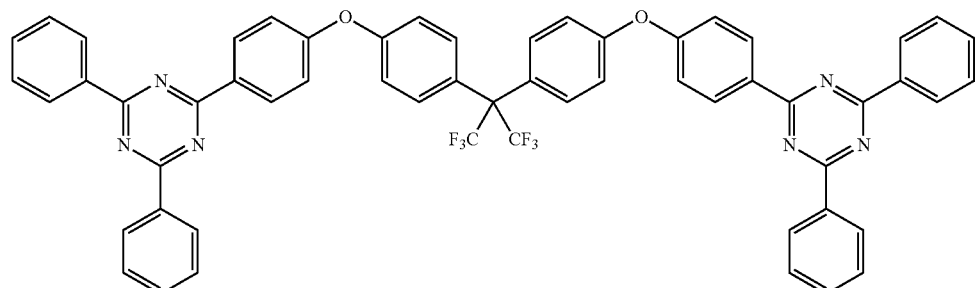
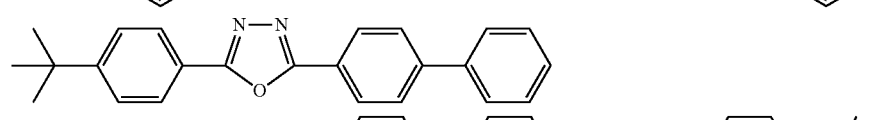
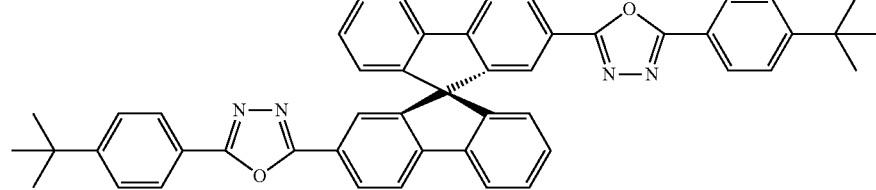

-continued
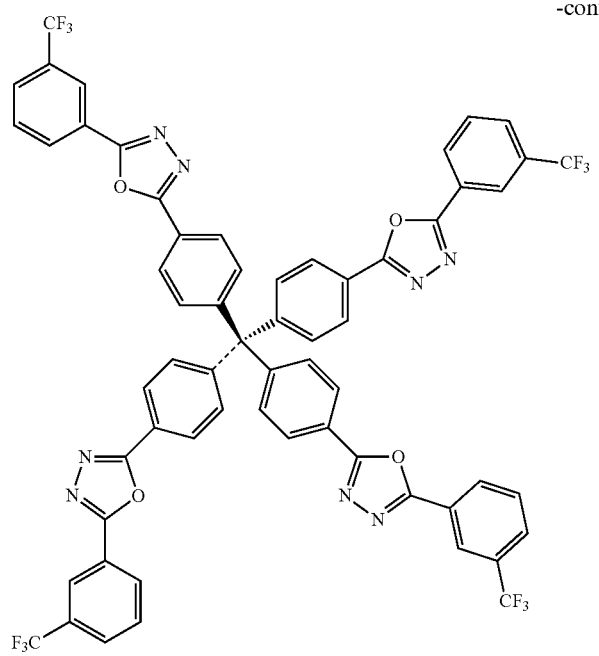
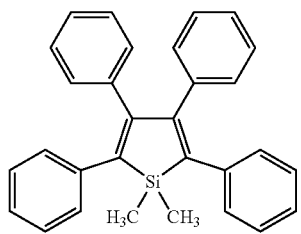
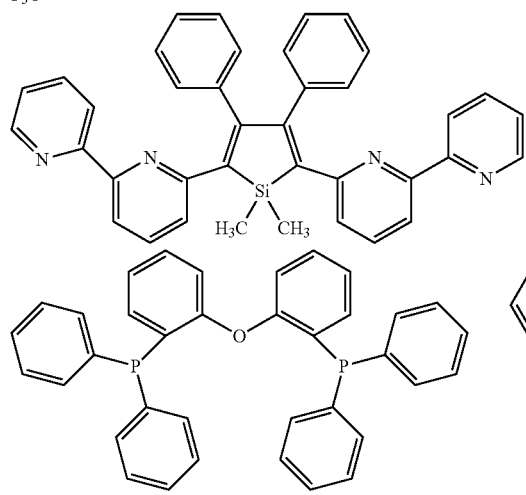
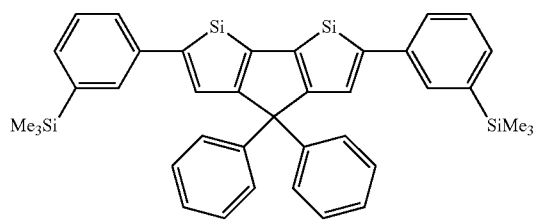
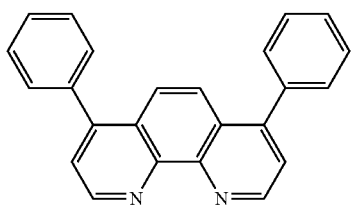
Preferred examples of a compound that may be used as the electron injection material are shown below.
Preferred examples of a compound as a material that may be added are shown below. For example, the compound may be added as a stabilizing material.
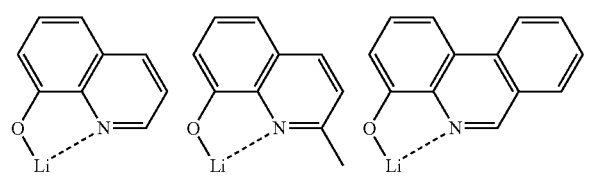
LiF
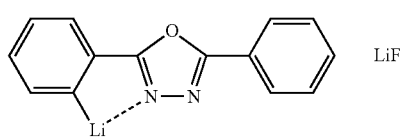
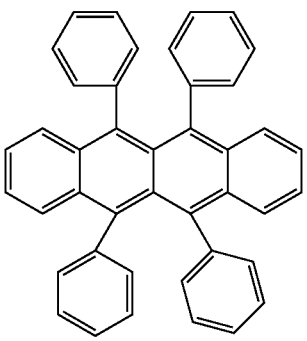

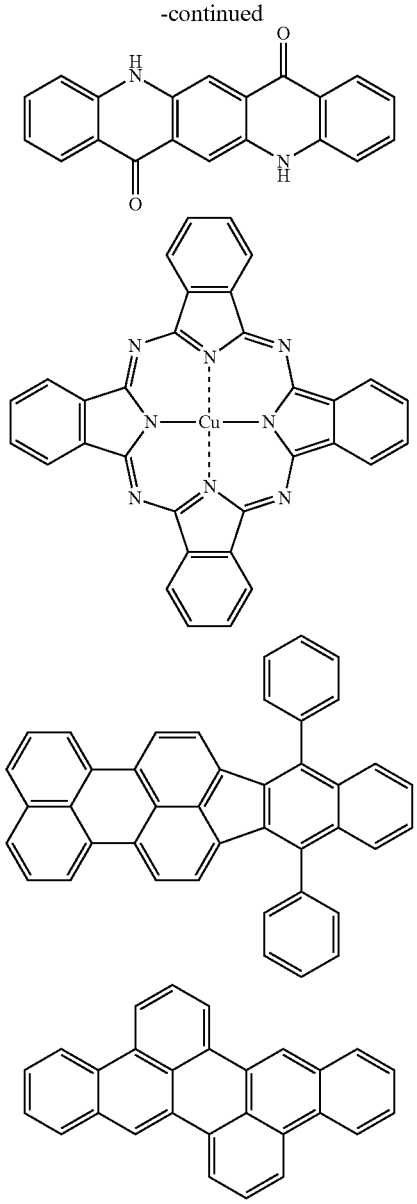

The organic electroluminescent device thus produced by the aforementioned method emits light on application of an electric field between the anode and the cathode of the device. In this case, when the light emission is caused by the excited singlet energy, light having a wavelength that corresponds to the energy level thereof may be confirmed as fluorescent light and delayed fluorescent light. When the light emission is caused by the excited triplet energy, light having a wavelength that corresponds to the energy level thereof may be confirmed as phosphorescent light. The normal fluorescent light has a shorter light emission lifetime than the delayed fluorescent light, and thus the light emission lifetimes may be distinguished between the fluorescent light and the delayed fluorescent light.

The phosphorescent light may substantially not observed with a normal organic compound, such as the compound of the invention, at room temperature since the excited triplet energy is unstable, and is immediately deactivated due to the large kinetic constant of thermal deactivation and the small kinetic constant of light emission. The excited triplet energy of the normal organic compound may be measured by observing light emission under an extremely low temperature condition.

The organic light-emitting device of the invention contains the compound represented by the general formula (1) in at least one layer of the organic layer, and thereby electrons and holes are smoothly transported to the light-emitting layer and the light-emitting material, facilitating the aforementioned light emission with good efficiency. Furthermore, the characteristic deterioration due to a high temperature and the characteristic deterioration with the lapse of time in operation can be suppressed, thereby providing high thermal stability and a long lifetime of the device.

The organic electroluminescent device of the invention may be applied to any of a single device, a structure with plural devices disposed in an array, and a structure having anodes and cathodes disposed in an X-Y matrix. According to the invention, an organic light-emitting device that is largely improved in light emission efficiency may be obtained by adding the compound represented by the general formula (1) in the light-emitting layer. The organic light-emitting device, such as the organic electroluminescent device, of the invention may be applied to a further wide range of purposes. For example, an organic electroluminescent display apparatus may be produced with the organic electroluminescent device of the invention, and for the details thereof, reference may be made to S. Tokito, C. Adachi and H. Murata, "Yuki EL Display" (Organic EL Display) (Ohmsha, Ltd.). In particular, the organic electroluminescent device of the invention may be applied to organic electroluminescent illumination and backlight which are highly demanded.

EXAMPLES

The features of the invention will be described more specifically with reference to synthesis examples and working examples below. The materials, processes, procedures, and the like shown below may be appropriately modified unless they deviate from the substance of the invention. Accordingly, the scope of the invention is not construed as being limited to the specific examples shown below. The ultraviolet ray absorption spectrum was measured with UV-2550 (produced by Shimadzu Corporation) or LAMBDA 950-PKA (produced by Perkin-Elmer Corporation), the light emission spectrum was measured with Fluoromax-4 (produced by Horiba Jobin Yvon SAS), and the transient decay curve was measured with Quantaurus-tau (produced by Hamamatsu Photonics K.K.). In the working examples, fluorescent light that had a light emission lifetime of 0.05 μs or more was determined as delayed fluorescent light.

Synthesis Example 1

Synthesis of Compound 1

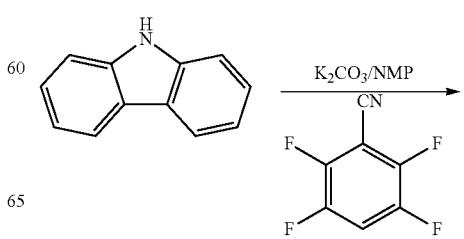

-continued

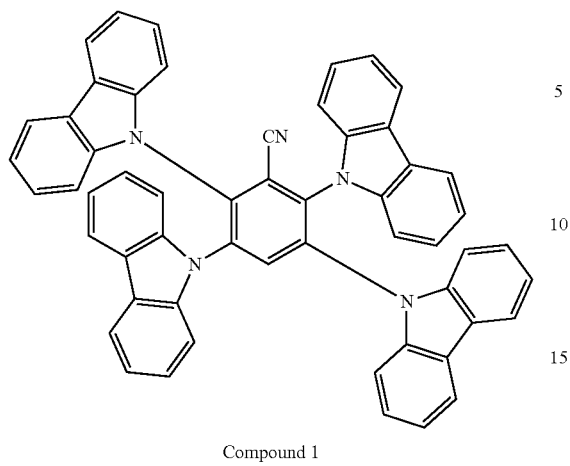

Compound 1

Potassium carbonate (8.14 g, 58.9 mmol) and 9H-carbazole (6.57 g, 39.3 mmol) were added to a 100 mL three-neck flask having been substituted with nitrogen, and 45 mL of dehydrated N-methyl-2-pyrrolidone was further added thereto, followed by stirring at room temperature for 1 hour. To the mixture, 2,3,5,6-tetrafluorobenzonitrile (1.37 g, 7.85 mmol) was added under a nitrogen stream, and the mixture was stirred at 80° C. for 12 hours. The solid matter deposited through reaction was recovered by suction filtration, and rinsed with water and methanol. Methanol was added to the rinsed solid matter, which was then stirred under heating, and the solid matter was recovered by suction filtration. Recrystallization from ethyl acetate provided the target material as a yellow solid matter in a yield amount of 3.28 g and a yield of 54.7%.

$^1$H-NMR (500 MHz, CDCl$_3$, δ): 8.45 (s, 1H), 7.80-7.77 (m, 8H), 7.36 (d, J=8.0 Hz, 4H), 7.32-7.31 (m, 4H), 7.19 (td, J=7.5 Hz, 1.0 Hz, 4H), 7.15-7.10 (m, 12H)

ASAP Mass Spectrum Analysis:
   Theoretical value: 763.9
   Observed value: 763.9

Synthesis Example 2

Synthesis of Compound 2

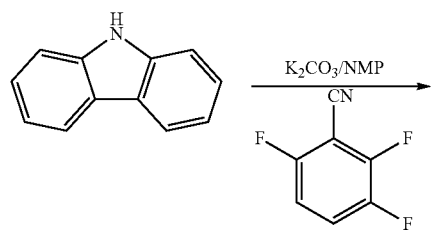

-continued

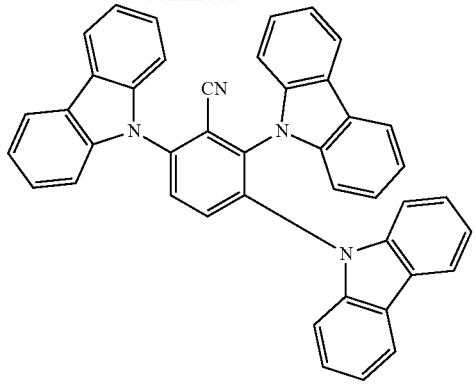

Compound 2

Potassium carbonate (25.7 g, 187 mmol) and 9H-carbazole (20.8 g, 124 mmol) were added to a 300 mL three-neck flask having been substituted with nitrogen, and 180 mL of dehydrated N-methyl-2-pyrrolidone was further added thereto, followed by stirring at room temperature for 1 hour. To the mixture, 2,3,6-trifluorobenzonitrile (3.00 g, 19.1 mmol) was added under a nitrogen stream, and the mixture was stirred at 100° C. for 12 hours. After completing the stirring, water was added to the mixture to deposit a solid matter, and the solid matter deposited was recovered by suction filtration, and rinsed with water and methanol. Methanol was added to the rinsed solid matter, which was then stirred under heating, and the solid matter was recovered by suction filtration. The resulting solid matter was dissolved in heated chloroform, and purified by silica gel column chromatography with chloroform as a developing solvent, and the fraction was concentrated to provide a solid matter. Methanol was added to the resulting solid matter, which was then stirred under heating, and the solid matter was recovered by suction filtration. The solid matter was rinsed with heated methanol to provide the target material as a pale yellow solid matter in a yield amount of 8.11 g and a yield of 71.1%.

$^1$H-NMR (500 MHz, CDCl$_3$, δ): 8.23 (d, J=9.0 Hz, 1H), 8.20 (d, J=7.5 Hz, 2H), 7.99 (d, J=8.5 Hz, 1H), 7.78 (dd, J=8.0 Hz, 2.0 Hz, 2H), 7.75 (dd, J=8.0 Hz, 2.0 Hz, 2H), 7.60-7.54 (m, 4H), 7.41 (td, J=8.5 Hz, 1.0 Hz, 2H), 7.20-7.15 (m, 4H), 7.14-7.04 (m, 8H)

ASAP Mass Spectrum Analysis:
   Theoretical value: 598.7
   Observed value: 598.6

Synthesis Example 3

Synthesis of Compound 3

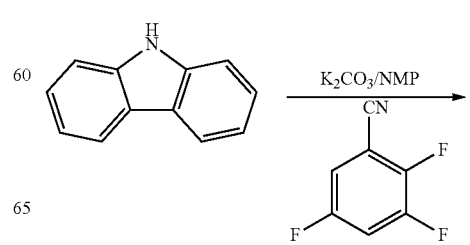

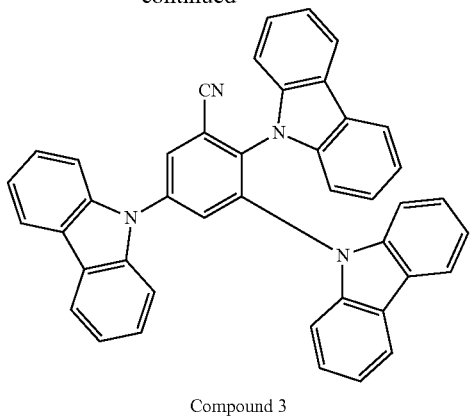

Compound 3

Potassium carbonate (42.9 g, 310 mmol) and 9H-carbazole (34.6 g, 207 mmol) were added to a 300 mL three-neck flask having been substituted with nitrogen, and 180 mL of dehydrated N-methyl-2-pyrrolidone was further added thereto, followed by stirring at room temperature for 1 hour. To the mixture, 2,3,5-trifluorobenzonitrile (5.00 g, 31.8 mmol) was added under a nitrogen stream, and the mixture was stirred at 100° C. for 12 hours. After completing the stirring, water was added to the mixture to deposit a solid matter, and the solid matter deposited was recovered by suction filtration, and rinsed with water and methanol. Methanol was added to the rinsed solid matter, which was then stirred under heating, and the solid matter was recovered by suction filtration. The resulting solid matter was dissolved in heated chloroform, and purified by silica gel column chromatography with chloroform as a developing solvent, and the fraction was concentrated to provide a solid matter. Methanol was added to the resulting solid matter, which was then stirred under heating, and the solid matter was recovered by suction filtration. The solid matter was rinsed with heated methanol to provide the target material as a pale yellow solid matter in a yield amount of 14.2 g and a yield of 74.7%.

$^1$H-NMR (500 MHz, CDCl$_3$, δ): 8.30 (dd, J=7.5 Hz, 2.5 Hz, 2H), 8.18 (d, J=7.5 Hz, 2H), 7.78-7.72 (m, 4H), 7.68 (d, J=8.0 Hz, 2H), 7.52 (td, J=7.5 Hz, 1.0 Hz, 2H), 7.40 (td, J=7.5 Hz, 1.0 Hz, 2H), 7.19-7.16 (m, 2H), 7.14-7.09 (m, 6H), 7.09-7.01 (m, 4H)

ASAP Mass Spectrum Analysis:

Theoretical value: 598.7

Observed value: 598.6

Synthesis Example 4

Synthesis of Compound 814

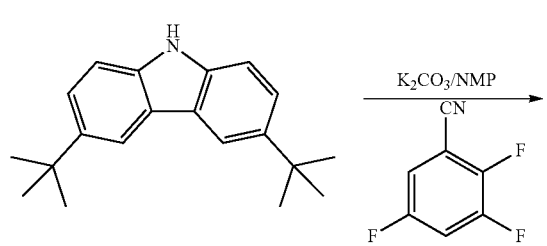

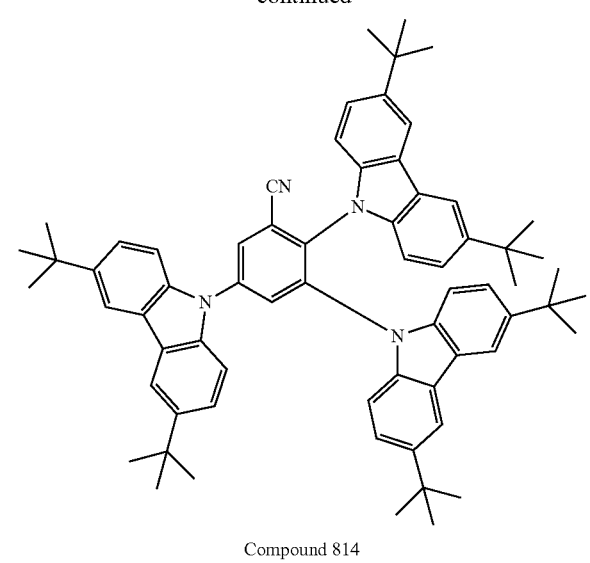

Compound 814

Potassium carbonate (2.33 g, 16.9 mmol) and 3,6-di-tert-butyl-9H-carbazole (3.14 g, 11.3 mmol) were added to a 300 mL three-neck flask having been substituted with nitrogen, and 30 mL of dehydrated N-methyl-2-pyrrolidone was further added thereto, followed by stirring at room temperature for 1 hour. To the mixture, 2,3,5-trifluorobenzonitrile (0.392 g, 2.50 mmol) was added under a nitrogen stream, and the mixture was stirred at 100° C. for 36 hours. After completing the stirring, water was added to the mixture to deposit a solid matter, and the solid matter deposited was recovered by suction filtration, and rinsed with water and hexane. Hexane was added to the rinsed solid matter, which was then stirred under heating, and the solid matter was recovered by suction filtration to provide the target material as a white solid matter in a yield amount of 1.55 g and a yield of 66.2%.

$^1$H-NMR (500 MHz, CDCl$_3$, δ): 8.28 (dd, J=14 Hz, 2.5 Hz, 2H), 8.18 (d, J=1.7 Hz, 2H), 7.65 (d, J=8.6 Hz, 2H), 7.59-7.56 (m, 6H), 6.93 (dd, J=8.5 Hz, 2.0 Hz, 2H), 6.88 (dd, J=8.5 Hz, 2.0 Hz, 2H), 6.86 (dd, J=8.5 Hz, 2.0 Hz, 2H), 6.76 (dd, J=8.5 Hz, 2.0 Hz, 2H), 1.49 (s, 18H), 1.34 (d, 36H)

ASAP Mass Spectrum Analysis:

Theoretical value: 935.4

Observed value: 935.2

Synthesis Example 5

Synthesis of Compound 816

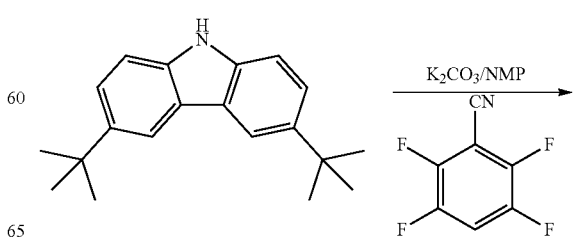

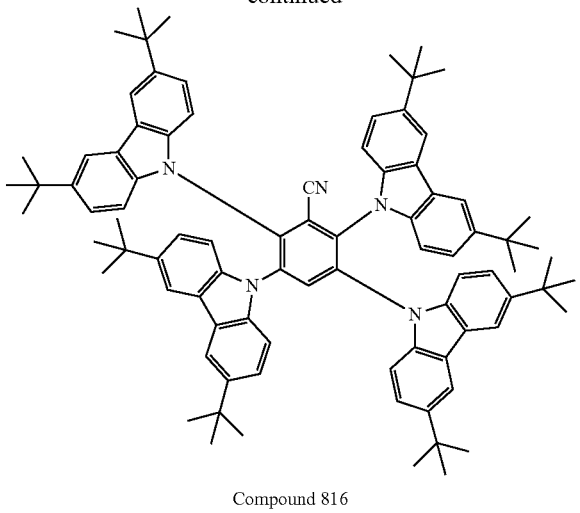

Compound 816

Potassium carbonate (3.46 g, 25.0 mmol) and 3,6-di-tert-butyl-9H-carbazole (4.67 g, 16.7 mmol) were added to a 100 mL three-neck flask having been substituted with nitrogen, and 30 mL of dehydrated N-methyl-2-pyrrolidone was further added thereto, followed by stirring at room temperature for 1 hour. To the mixture, 2,3,5,6-tetrafluorobenzonitrile (0.450 g, 2.57 mmol) was added under a nitrogen stream, and the mixture was stirred at 95° C. for 12 hours. After completing the stirring, the solid matter deposited was recovered by suction filtration, and rinsed with water and hexane. Hexane was added to the rinsed solid matter, which was then stirred under heating, and the solid matter was recovered by suction filtration to provide the target material as a yellow solid matter in a yield amount of 2.65 g and a yield of 85.2%.

$^1$H NMR (500 MHz, CDCl$_3$, δ): 8.43 (s, 1H), 7.61 (d, J=7.0 Hz, 8H), 7.09-6.99 (m, 16H), 1.37 (s, 72H)

ASAP Mass Spectrum Analysis:
  Theoretical value: 1212
  Observed value: 1212

Example 1

Preparation and Evaluation of Organic Photoluminescent Device Using Compound 1

A toluene solution of the compound 1 (concentration: $1\times10^{-5}$ mol/L) was prepared in a glove box under an Ar atmosphere.

Figure 2:
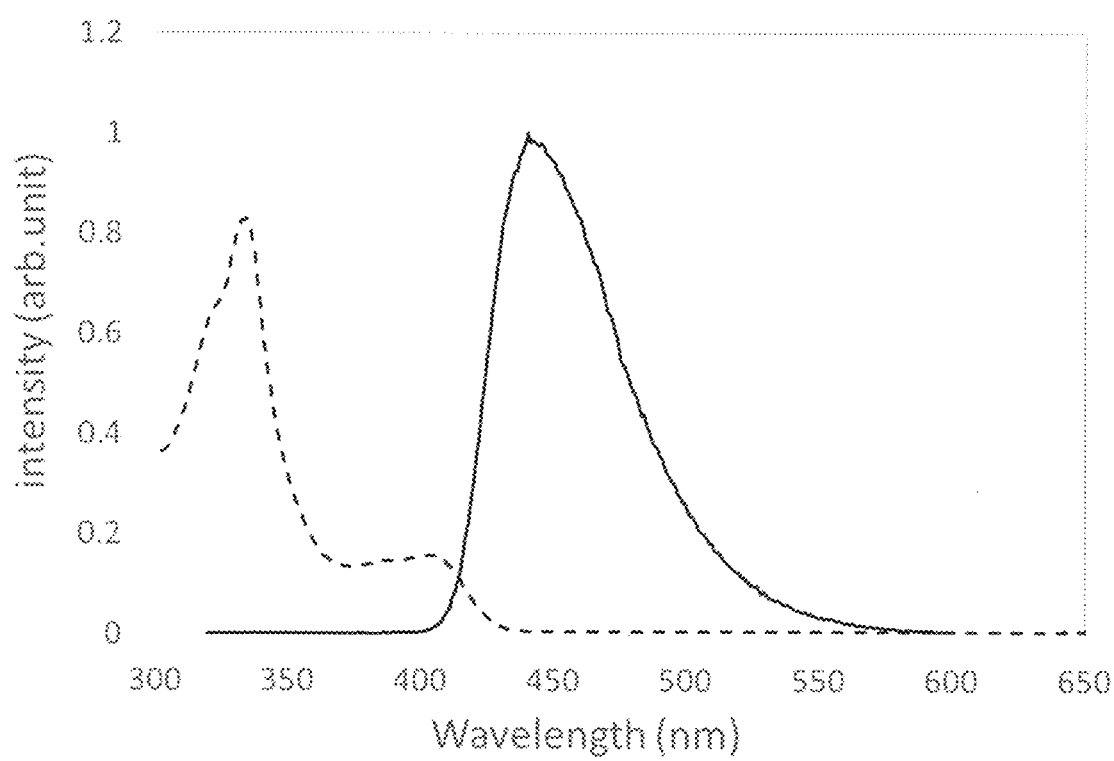
FIG. 2 is the light emission spectrum and the light absorption spectrum of the toluene solution of the compound 1 in Example 1.
Figure 3:
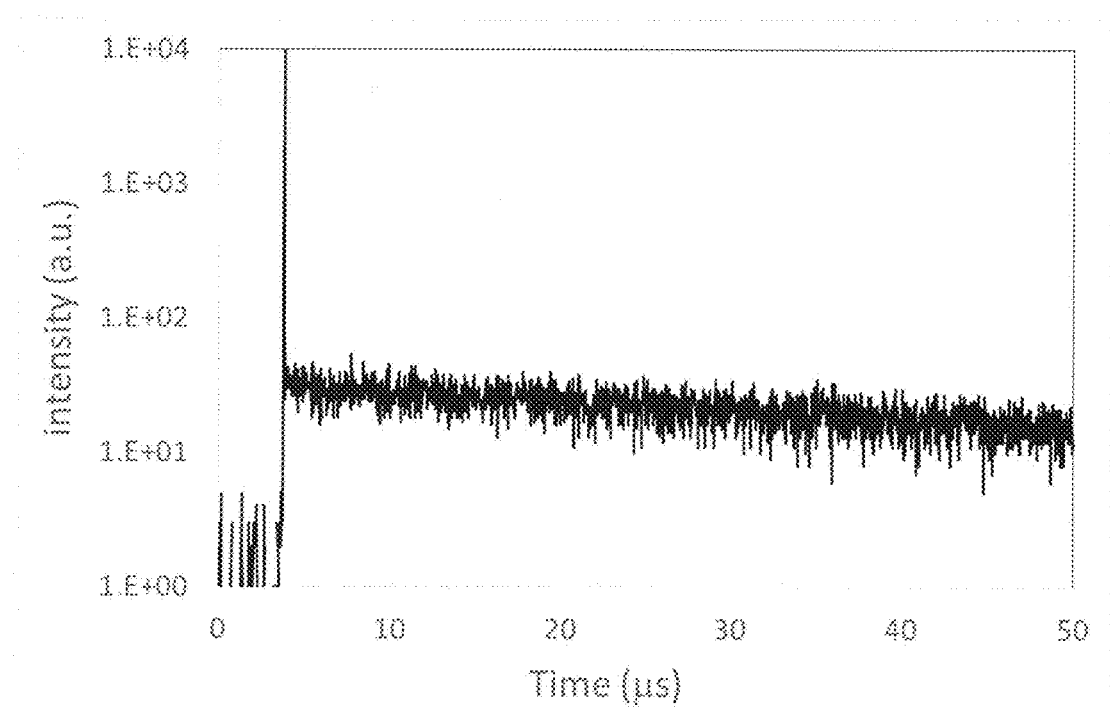
FIG. 3 is the transient decay curves of the toluene solution of the compound 1 in Example 1.

For the toluene solution of the compound 1, the light emission spectrum and the light absorption spectrum measured with excitation light of 300 nm are shown in FIG. 2, and the transient decay curve measured with excitation light of 340 nm after bubbling with argon is shown in FIG. 3. In FIG. 2, the solid line shows the light emission spectrum, and the broken line shows the light absorption spectrum. The photoluminescence quantum efficiency was 12.0% for the toluene solution before bubbling, and 45.4% for the toluene solution after bubbling with argon. A fluorescent light component rapidly attenuated and a delayed fluorescent light component slowly attenuated were confirmed from FIG. 3, in which the light emission lifetime of the fluorescent light component rapidly attenuated was 1.65 ns (nanosecond), and the light emission lifetime of the delayed fluorescent light component was 70 µs.

It was confirmed from the results that the compound 1 was a compound capable of emitting delayed fluorescent light and had a high light emission efficiency.

Example 2

Preparation and Evaluation of Organic Photoluminescent Device Using Compound 2

A toluene solution (concentration: $1\times10^{-5}$ mol/L) was prepared under the same condition as in Example 1 except that the compound 2 was used instead of the compound 1.

Figure 4:
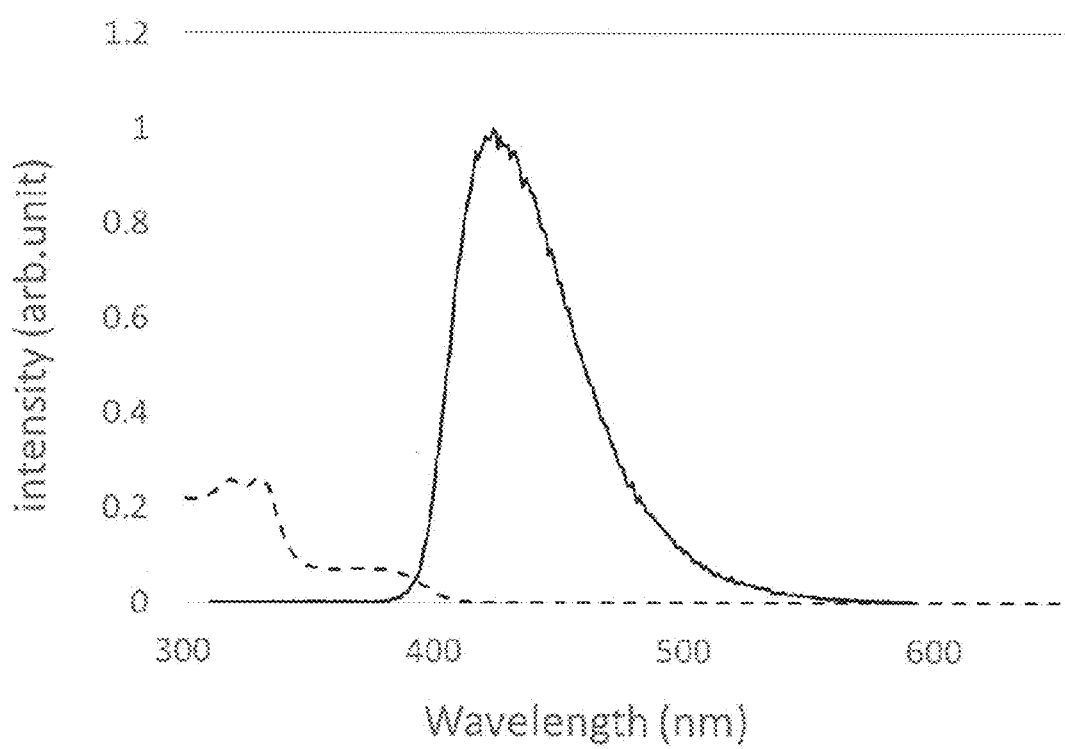
FIG. 4 is the light emission spectrum and the light absorption spectrum of the toluene solution of the compound 2 in Example 2.
Figure 5:
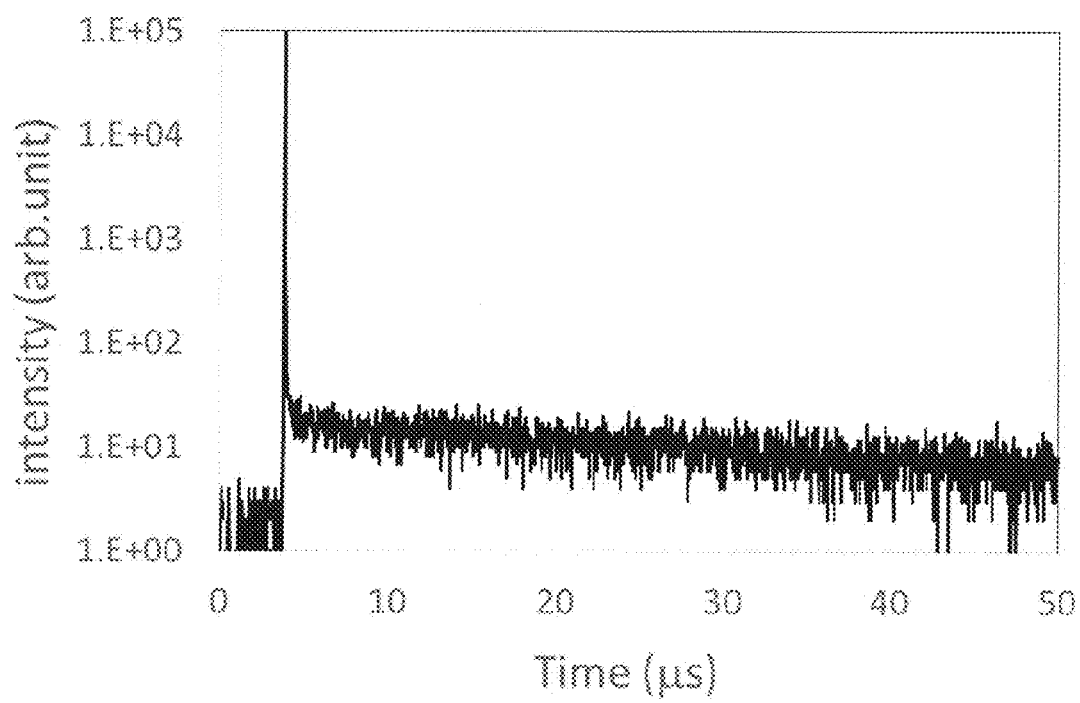
FIG. 5 is the transient decay curves of the toluene solution of the compound 2 in Example 2.

For the toluene solution of the compound 2, the light emission spectrum and the light absorption spectrum measured with excitation light of 337 nm are shown in FIG. 4, and the transient decay curve measured with excitation light of 340 nm after bubbling with argon is shown in FIG. 5. In FIG. 4, the solid line shows the light emission spectrum, and the broken line shows the light absorption spectrum. The photoluminescence quantum efficiency was 10.0% for the toluene solution before bubbling, and 13.7% for the toluene solution after bubbling with argon. A fluorescent light component rapidly attenuated and a delayed fluorescent light component slowly attenuated were confirmed from FIG. 5, in which the light emission lifetime of the fluorescent light component rapidly attenuated was 2.8 ns, and the light emission lifetime of the delayed fluorescent light component was 17 µs.

It was confirmed from the results that the compound 2 was a compound capable of emitting delayed fluorescent light and had a high light emission efficiency.

Example 3

Preparation and Evaluation of Organic Photoluminescent Device Using Compound 3

A toluene solution (concentration: $1\times10^{-5}$ mol/L) was prepared under the same condition as in Example 1 except that the compound 3 was used instead of the compound 1.

Figure 6:
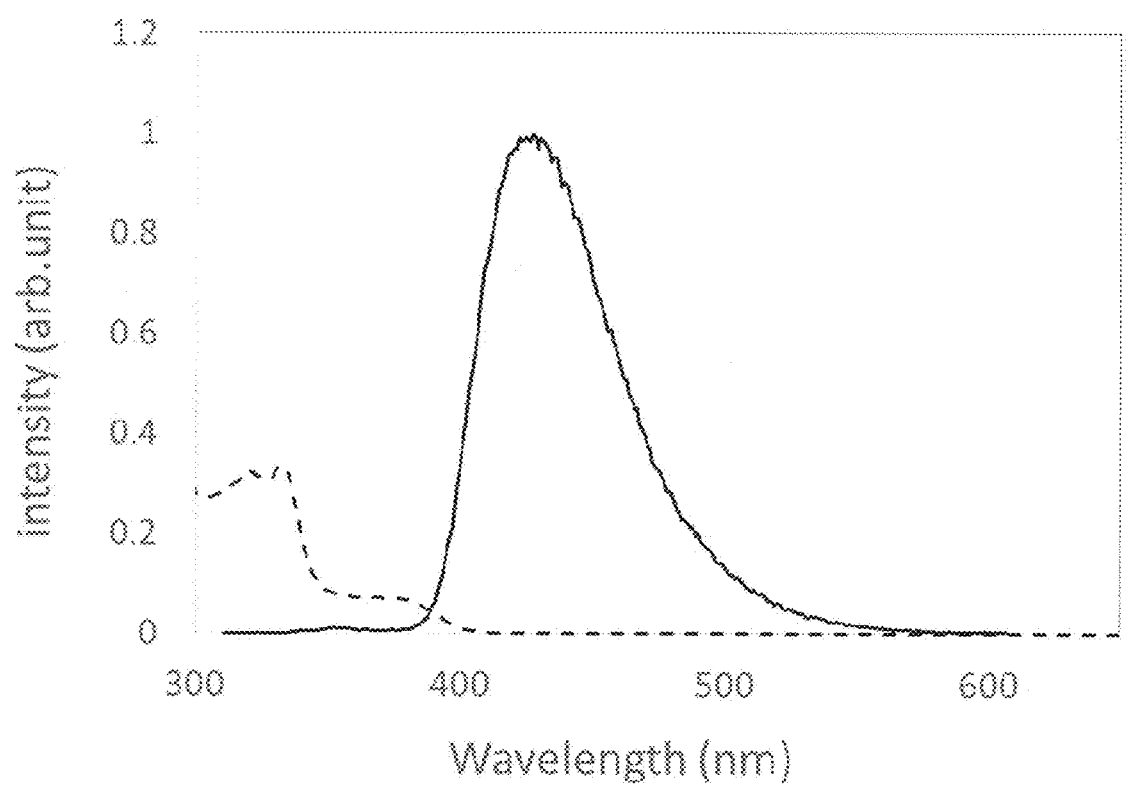
FIG. 6 is the light emission spectrum and the light absorption spectrum of the toluene solution of the compound 3 in Example 3.
Figure 7:
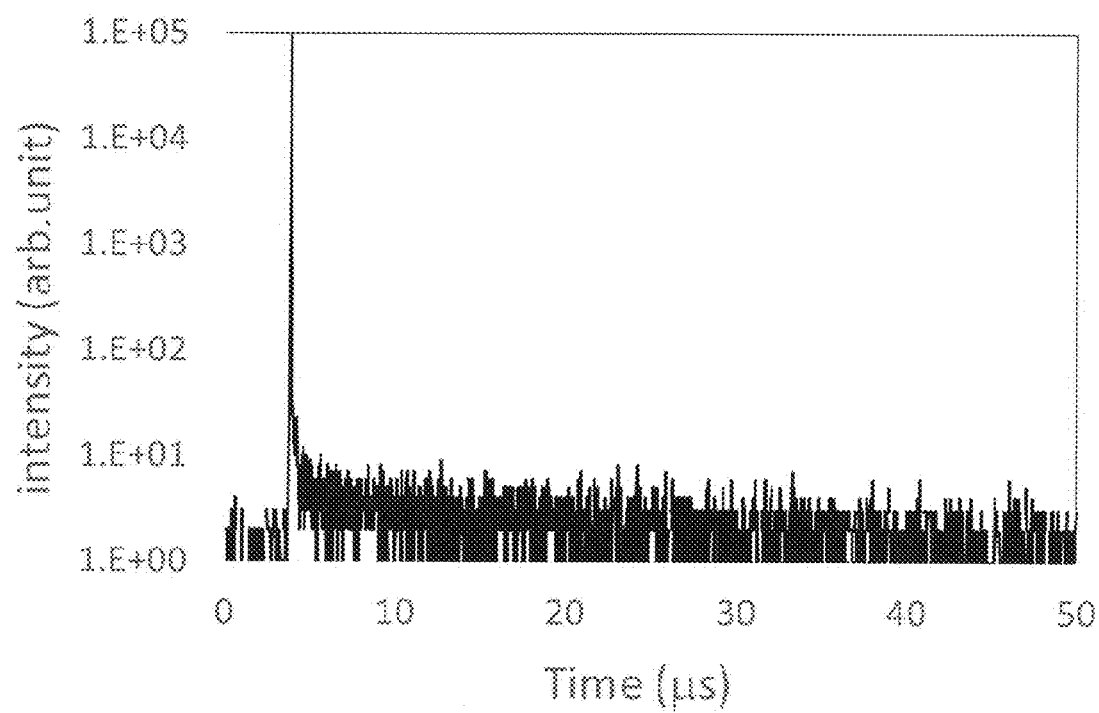
FIG. 7 is the transient decay curves of the toluene solution of the compound 3 in Example 3.

For the toluene solution of the compound 3, the light emission spectrum and the light absorption spectrum measured with excitation light of 337 nm are shown in FIG. 6, and the transient decay curve measured with excitation light of 340 nm after bubbling with argon is shown in FIG. 7. In FIG. 6, the solid line shows the light emission spectrum, and the broken line shows the light absorption spectrum. The photoluminescence quantum efficiency was 17.8% for the toluene solution before bubbling, and 21.0% for the toluene solution after bubbling with argon. A fluorescent light component rapidly attenuated and a delayed fluorescent light component slowly attenuated were confirmed from FIG. 7, in which the light emission lifetime of the fluorescent light component rapidly attenuated was 6.6 ns, and the light emission lifetime of the delayed fluorescent light component was 96 µs.

It was confirmed from the results that the compound 3 was a compound capable of emitting delayed fluorescent light and had a high light emission efficiency.

Example 4

Preparation and Evaluation of Organic Photoluminescent Device Using Compound 814

A toluene solution (concentration: $1\times10^{-5}$ mol/L) was prepared under the same condition as in Example 1 except that the compound 814 was used instead of the compound 1.

Figure 8:
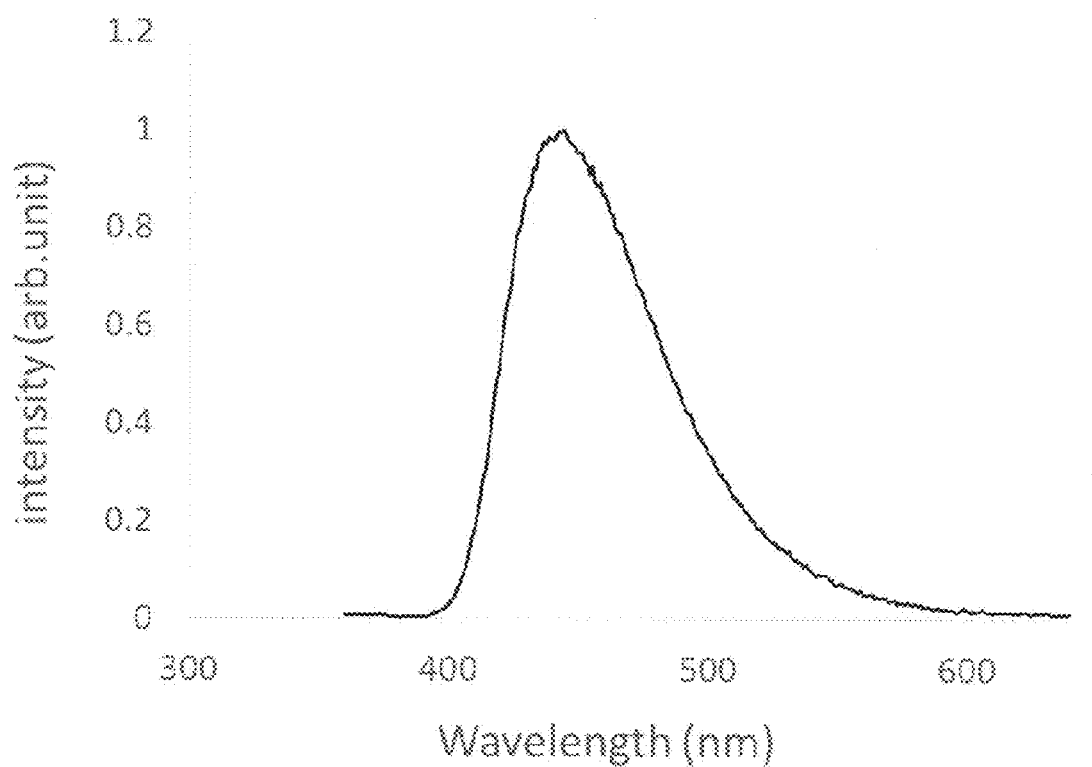
FIG. 8 is the light absorption spectrum of the toluene solution of the compound 814 in Example 4.
Figure 9:
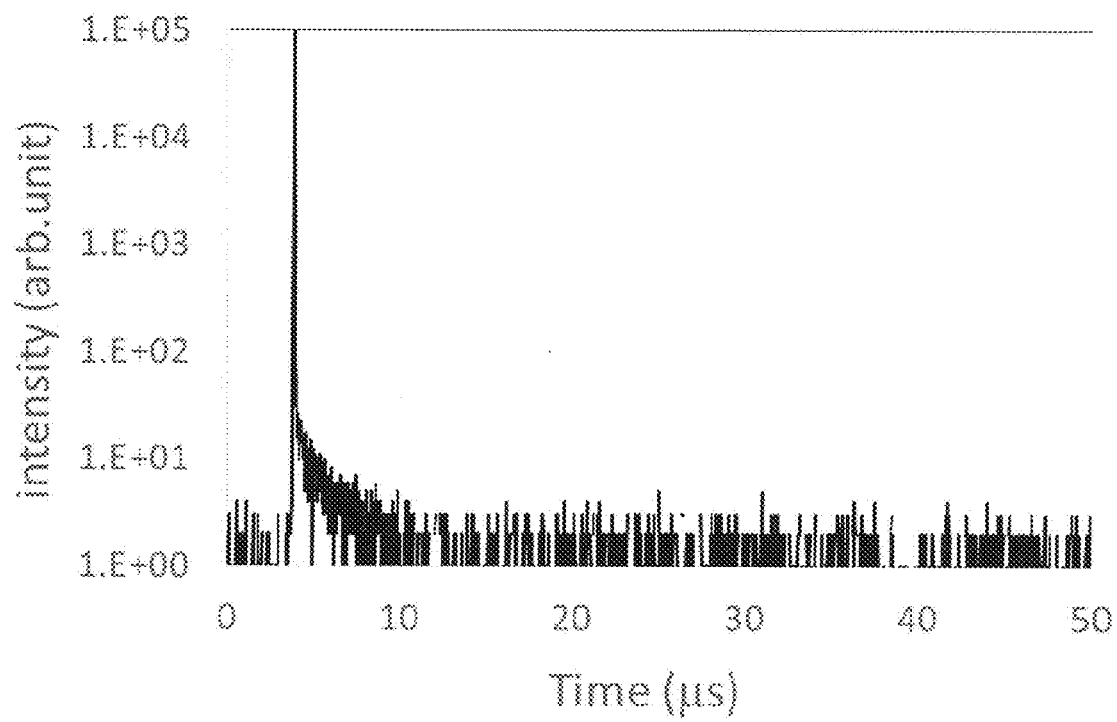
FIG. 9 is the transient decay curves of the toluene solution of the compound 814 in Example 4.

For the toluene solution of the compound 814, the light emission spectrum measured with excitation light of 337 nm is shown in FIG. 8, and the transient decay curve measured with excitation light of 340 nm after bubbling with argon is shown in FIG. 9. The photoluminescence quantum efficiency was 27.4% for the toluene solution before bubbling, and 37.4% for the toluene solution after bubbling with argon. A fluorescent light component rapidly attenuated and a delayed fluorescent light component slowly attenuated were confirmed from FIG. 9, in which the light emission lifetime of the fluorescent light component rapidly attenuated was 6.7 ns, and the light emission lifetime of the delayed fluorescent light component was 2.5 µs.

It was confirmed from the results that the compound 814 was a compound capable of emitting delayed fluorescent light and had a high light emission efficiency.

Example 5

Preparation and Evaluation of Organic Photoluminescent Device Using Compound 816

A toluene solution (concentration: $1\times10^{-5}$ mol/L) was prepared under the same condition as in Example 1 except that the compound 816 was used instead of the compound 1.

Figure 10:
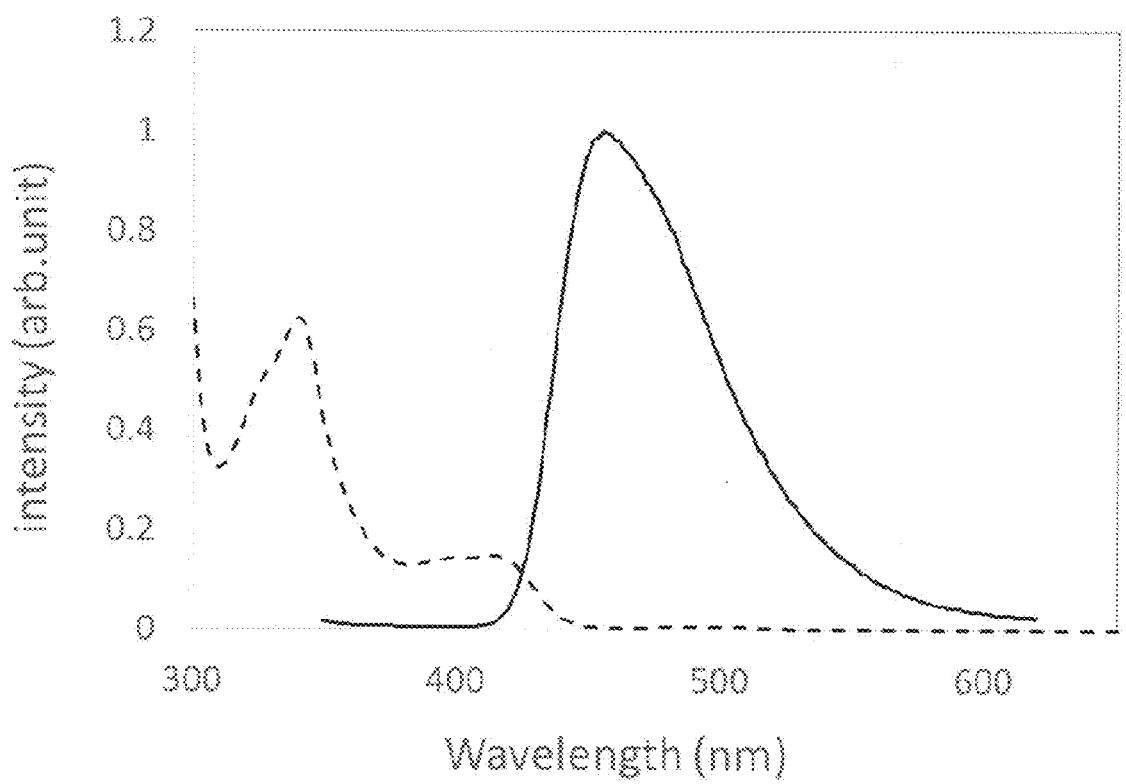
FIG. 10 is the light emission spectrum and the light absorption spectrum of the toluene solution of the compound 816 in Example 5.
Figure 11:
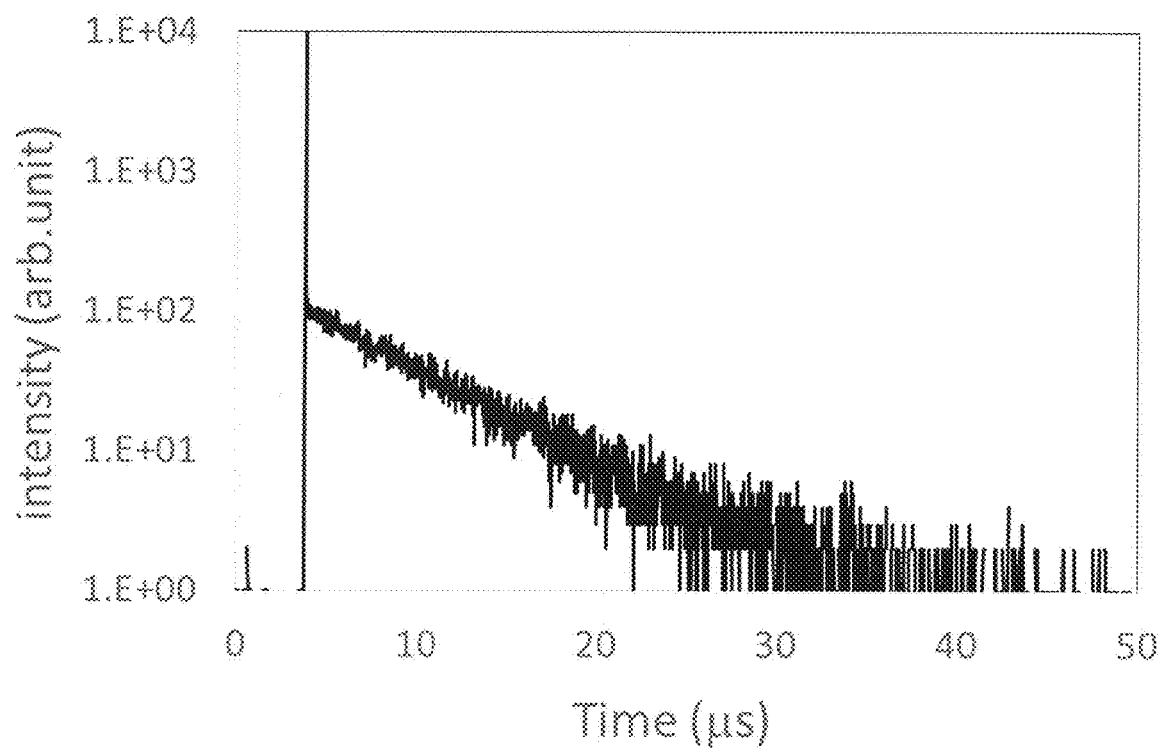
FIG. 11 is the transient decay curves of the toluene solution of the compound 816 in Example 5.

For the toluene solution of the compound 816, the light emission spectrum and the light absorption spectrum measured with excitation light of 337 nm are shown in FIG. 10, and the transient decay curve measured with excitation light of 340 nm after bubbling with argon is shown in FIG. 11. In FIG. 10, the solid line shows the light emission spectrum, and the broken line shows the light absorption spectrum. The photoluminescence quantum efficiency was 13.1% for the toluene solution before bubbling, and 39.4% for the toluene solution after bubbling with argon. A fluorescent light component rapidly attenuated and a delayed fluorescent light component slowly attenuated were confirmed from FIG. 11, in which the light emission lifetime of the fluorescent light component rapidly attenuated was 2.2 ns, and the light emission lifetime of the delayed fluorescent light component was 6.3 µs.

It was confirmed from the results that the compound 816 was a compound capable of emitting delayed fluorescent light and had a high light emission efficiency.

Comparative Example 1

Preparation and Evaluation of Organic Photoluminescent Device Using Comparative Compound 1

A toluene solution (concentration: $1\times10^{-5}$ mol/L) was prepared under the same condition as in Example 1 except that the comparative compound 1 shown by the following formula was used instead of the compound 1.

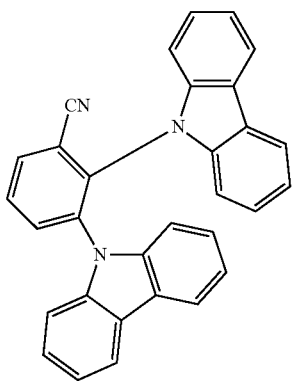

Comparative Compound 1

Figure 12:
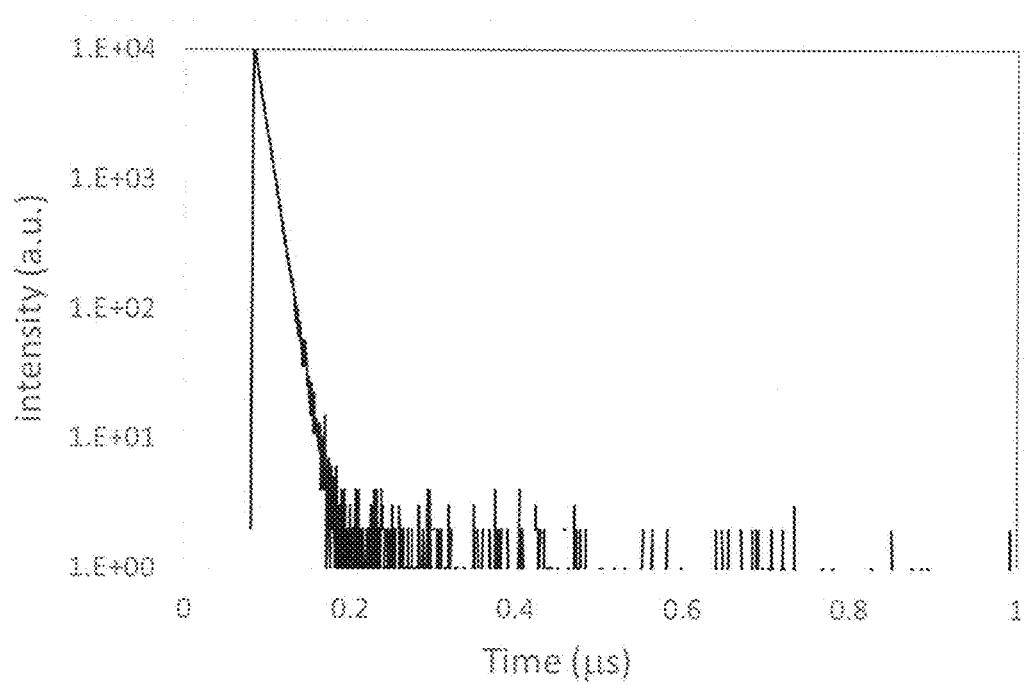
FIG. 12 is the transient decay curves of the toluene solution of the comparative compound 1.

For the toluene solution of the comparative compound 1, the transient decay curve measured with excitation light of 280 nm after bubbling with argon is shown in FIG. 12. The photoluminescence quantum efficiency was 17.0% for the toluene solution before bubbling, and 35.1% for the toluene solution after bubbling with argon. A delayed fluorescent light component was not confirmed from FIG. 12, and only the fluorescent light component rapidly attenuated (light emission lifetime: 10.9 ns) was observed.

Comparative Example 2

Preparation and Evaluation of Organic Photoluminescent Device Using Comparative Compound 2

A toluene solution (concentration: $1\times10^{-5}$ mol/L) was prepared under the same condition as in Example 1 except that the comparative compound 2 shown by the following formula was used instead of the compound 1.

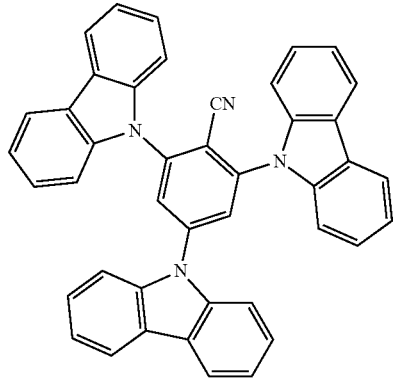

Comparative Compound 2

Figure 13:
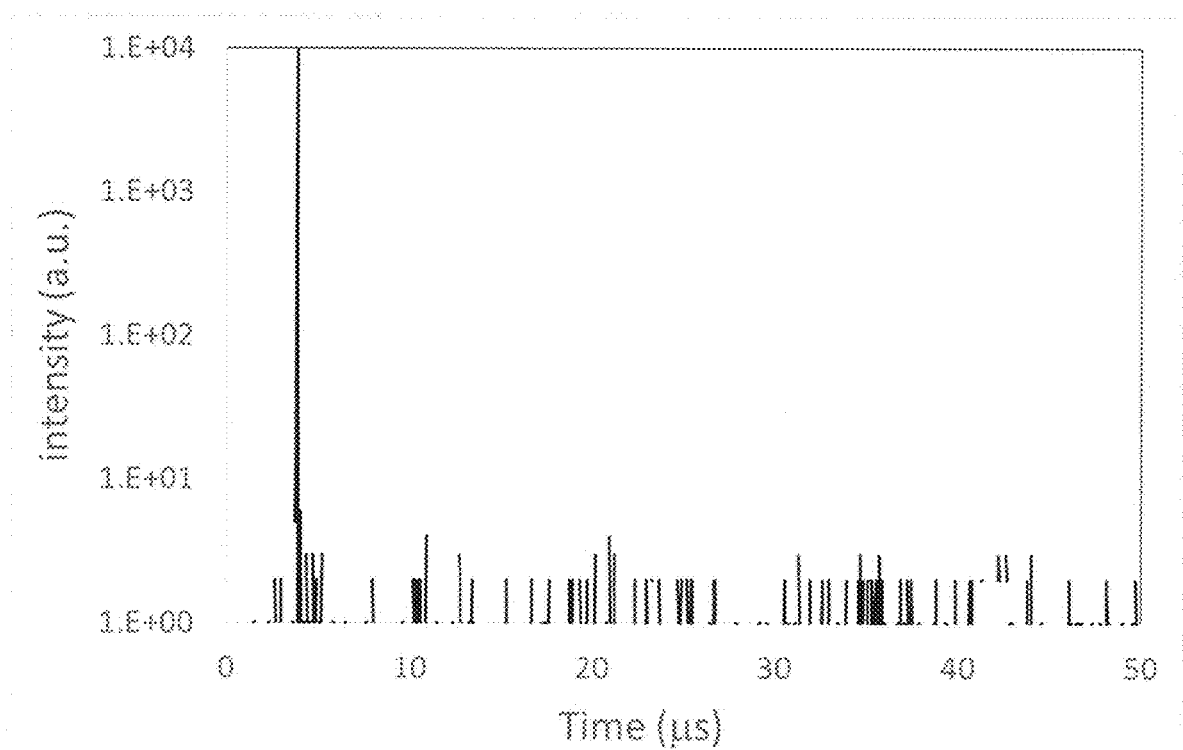
FIG. 13 is the transient decay curves of the toluene solution of the comparative compound 2.

For the toluene solution of the comparative compound 2, the transient decay curve measured with excitation light of 280 nm after bubbling with argon is shown in FIG. 13. The photoluminescence quantum efficiency was 14.4% for the toluene solution before bubbling, and 18.9% for the toluene solution after bubbling with argon. A delayed fluorescent light component was not confirmed from FIG. 13, and only the fluorescent light component rapidly attenuated (light emission lifetime: 3.75 ns) was observed.

Comparative Example 3

Preparation and Evaluation of Organic Photoluminescent Device Using Comparative Compound 3

A toluene solution (concentration: $1\times10^{-5}$ mol/L) was prepared under the same condition as in Example 1 except that the comparative compound 3 shown by the following formula was used instead of the compound 1.

Comparative Compound 3

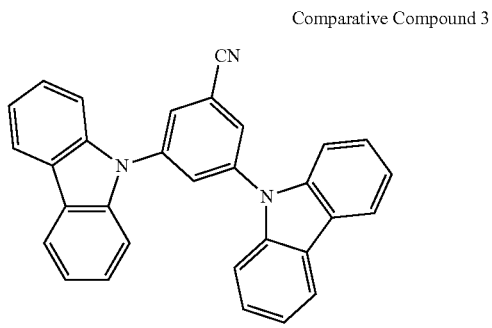 [SMILES: N#Cc1cc(-n2c3ccccc3c3ccccc32)cc(-n2c3ccccc3c3ccccc32)c1]

Figure 14:
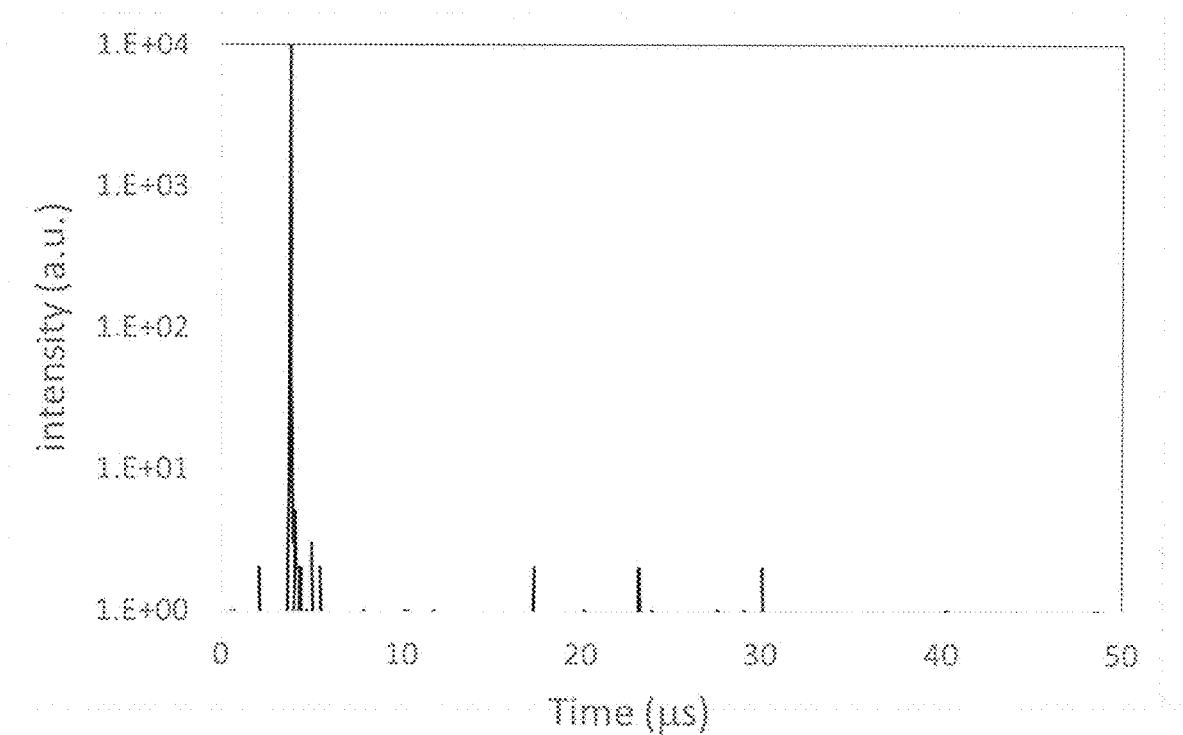
FIG. 14 is the transient decay curves of the toluene solution of the comparative compound 3.

For the toluene solution of the comparative compound 3, the transient decay curve measured with excitation light of 280 nm after bubbling with argon is shown in FIG. 14. The photoluminescence quantum efficiency was 8.60% for the toluene solution before bubbling, and 10.7% for the toluene solution after bubbling with argon. A delayed fluorescent light component was not confirmed from FIG. 14, and only the fluorescent light component rapidly attenuated (light emission lifetime: 3.94 ns) was observed.

Example 6

Preparation and Evaluation of Organic Electroluminescent Device Using Compound 1

Thin films were laminated on a glass substrate having formed thereon an anode formed of indium tin oxide (ITO) having a thickness of 100 nm, by a vacuum vapor deposition method at a vacuum degree of $5 \times 10^{-4}$ Pa. Firstly, HAT-CN was formed to a thickness of 10 nm on ITO, TAPC was formed to a thickness of 30 nm thereon, and mCP was formed to a thickness of 10 nm thereon. Subsequently, the compound 1 and PPT were co-deposited thereon from separate vapor deposition sources to form a layer having a thickness of 30 nm, which was designated as a light-emitting layer. At this time, the concentration of the compound 1 was 15% by weight. PPT was then formed to a thickness of 40 nm, further lithium fluoride (LiF) was vacuum vapor-deposited to a thickness of 0.8 nm, and then aluminum (Al) was vapor-deposited to a thickness of 100 nm to form a cathode, thereby completing an organic electroluminescent device.

Figure 15:
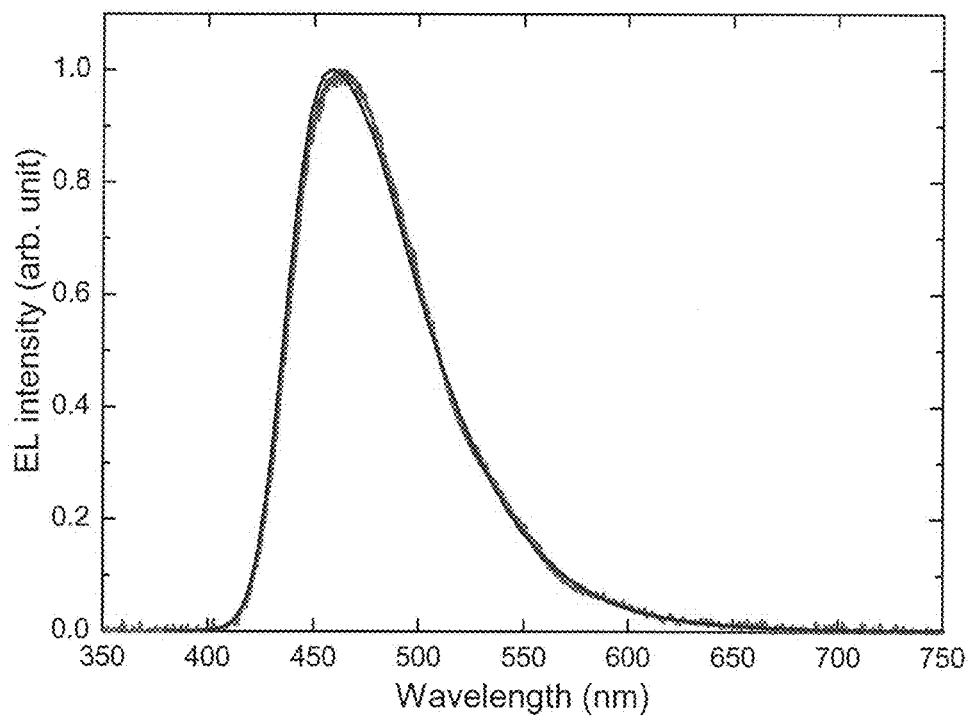
FIG. 15 is the light emission spectrum of the organic electroluminescent device using the compound 1.
Figure 16:
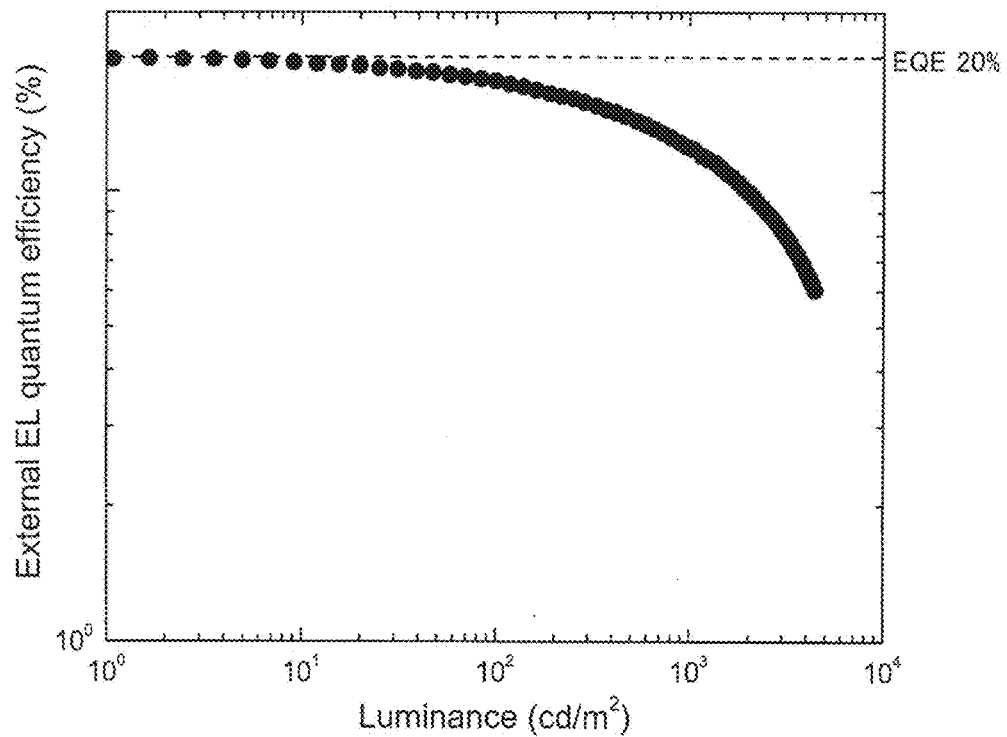
FIG. 16 is a graph showing the luminance-external quantum efficiency characteristics of the organic electroluminescent devices using the compound 1.

FIG. 15 shows the light emission spectra of the organic electroluminescent device thus produced. The CIE values were (0.16, 0.19). FIG. 16 shows the luminance-external quantum efficiency characteristics. It was confirmed that an external quantum efficiency of 20% was achieved.

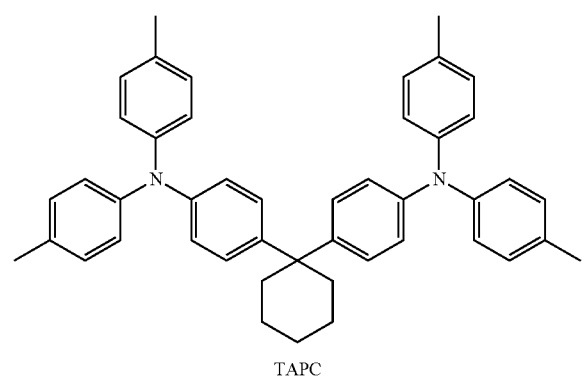

TAPC

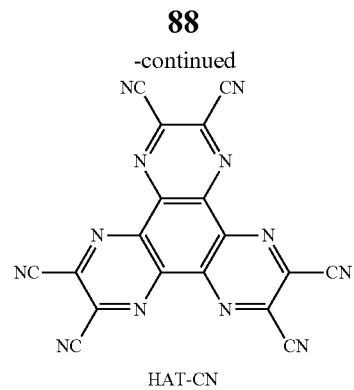

HAT-CN

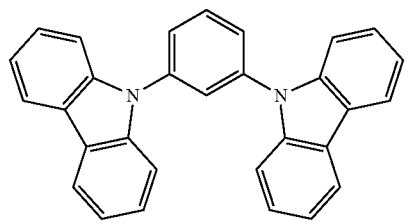

mCP

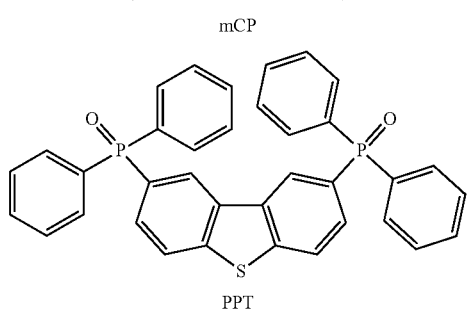

PPT

INDUSTRIAL APPLICABILITY

The compound of the invention is useful as a light-emitting material. Accordingly, the compound of the invention may be effectively used as a light-emitting material of an organic light-emitting device, such as an organic electroluminescent device. The compound of the invention includes a compound that emits delayed fluorescent light, and thus is capable of providing an organic light-emitting device having a high light emission efficiency. Accordingly, the invention has high industrial applicability.

REFERENCE SIGNS LIST

1 substrate
2 anode
3 hole injection layer
4 hole transporting layer
5 light-emitting layer
6 electron transporting layer
7 cathode

The invention claimed is:

1. A compound having a structure represented by the following general formula (1):

General Formula (1)

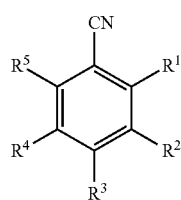

wherein in the general formula (1), three or more of $R^1$, $R^2$, $R^4$, and $R^5$ each independently represent a substituted or unsubstituted 9-carbazolyl group, a substituted or unsubstituted 10-phenoxazyl group, or a substituted or unsubstituted 10-phenothiazyl group, and the balance thereof represents a hydrogen atom or a substituent, provided that the substituent excludes a substituted or unsubstituted 9-carbazolyl group, a substituted or unsubstituted 10-phenoxazyl group, a substituted or unsubstituted 10-phenothiazyl group, or a cyano group, and one or more of carbon atom constituting ring skeletons of the substituted or unsubstituted 9-carbazolyl group, the substituted or unsubstituted 10-phenoxazyl group, and the substituted or unsubstituted 10-phenothiazyl group may be replaced by a nitrogen atom; and $R^3$ represents a hydrogen atom or a substituent, provided that the substituent excludes a substituted or unsubstituted 9-carbazolyl group, a substituted or unsubstituted 10-phenoxazyl group, a substituted or unsubstituted 10-phenothiazyl group, a cyano group, a substituted or unsubstituted aryl group, a substituted or unsubstituted heteroaryl group, and a substituted or unsubstituted alkynyl group, provided that when $R^3$ is a hydrogen atom and $R^1$, $R^2$, $R^4$, and $R^5$ have the same structure, then $R^1$, $R^2$, $R^4$, and $R^5$ have one of the following structures:

D2

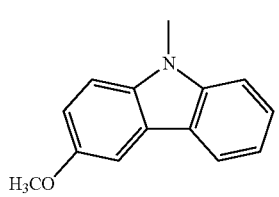

D3

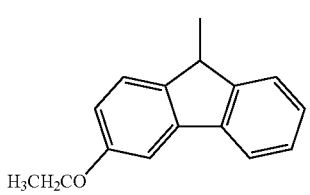

D4

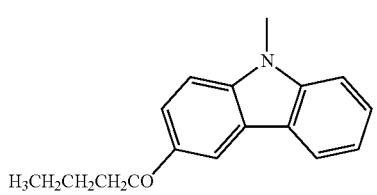

D5

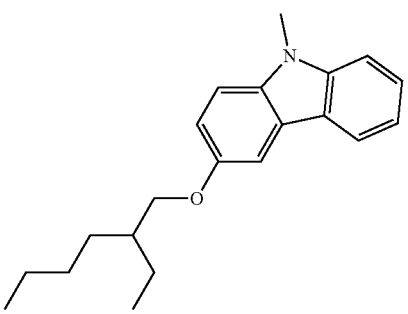

D7

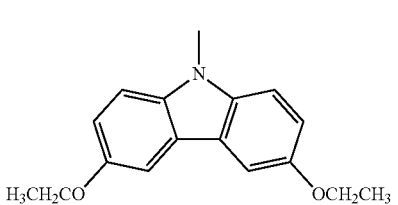

D8

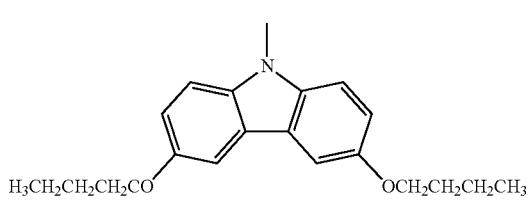

D9

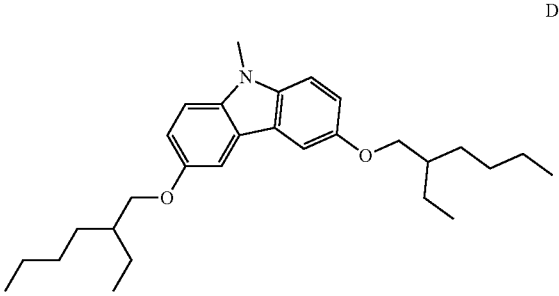

D10

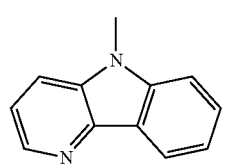

D11

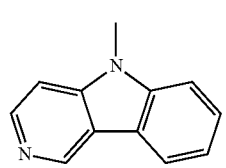

D12

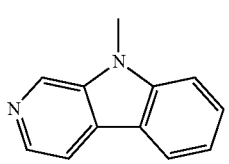

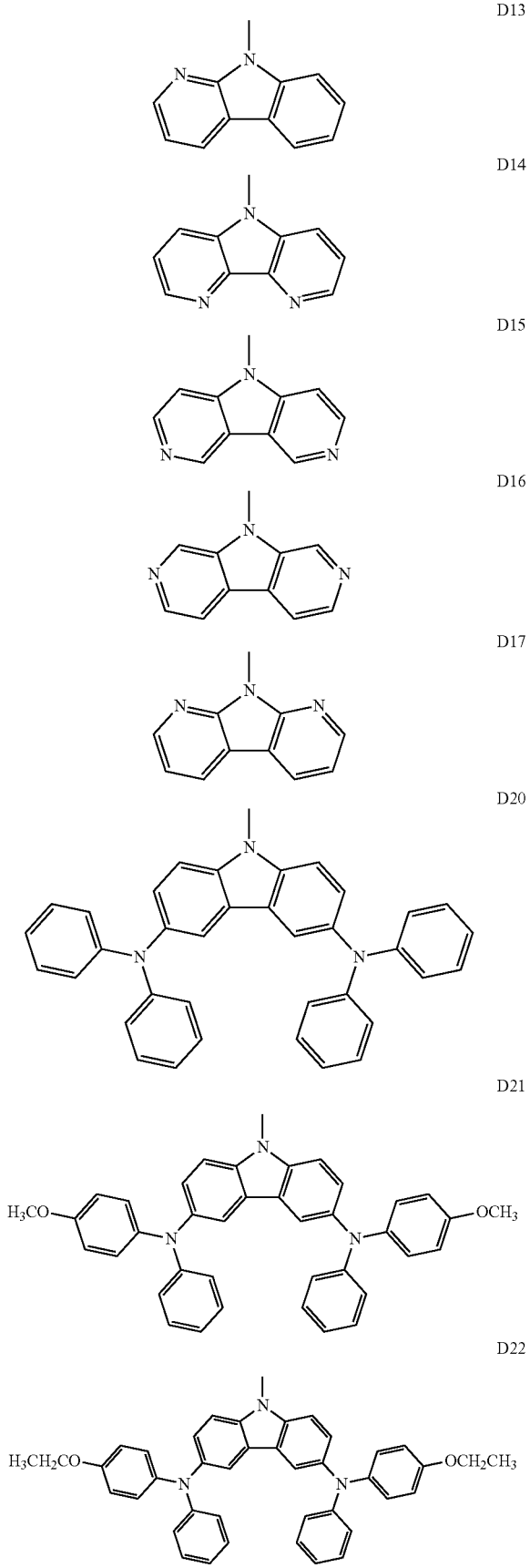

-continued
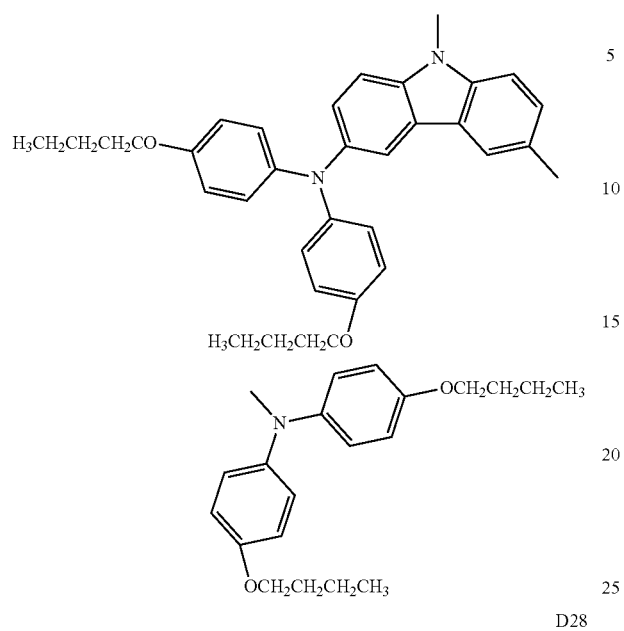
D27
D28
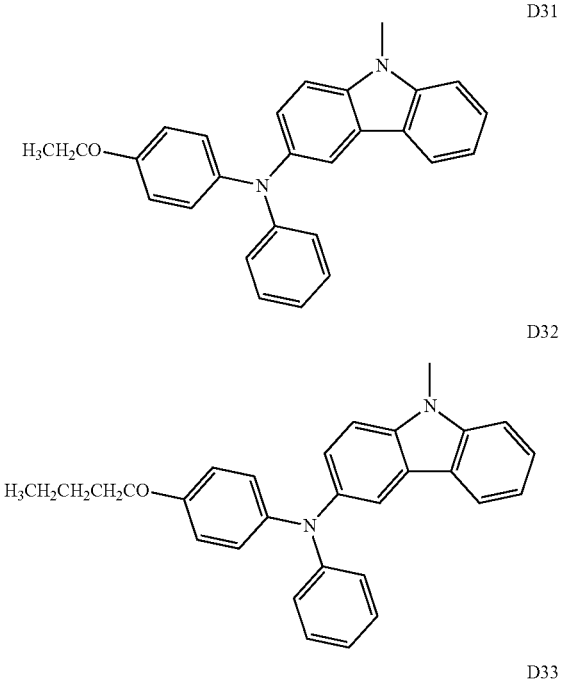
D31
D32
D33
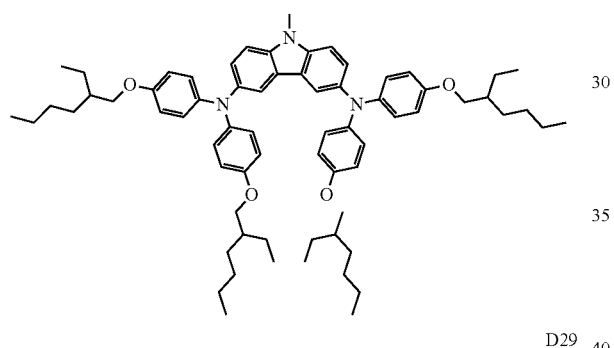
D29
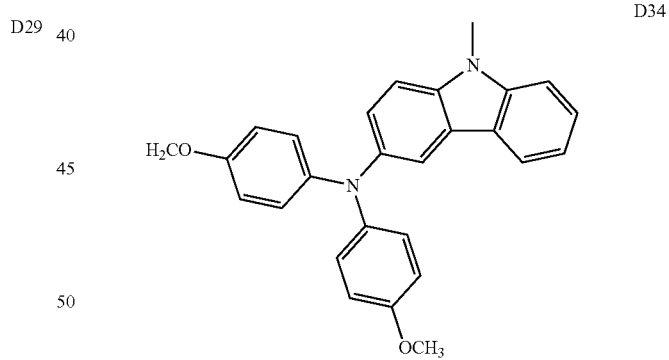
D34
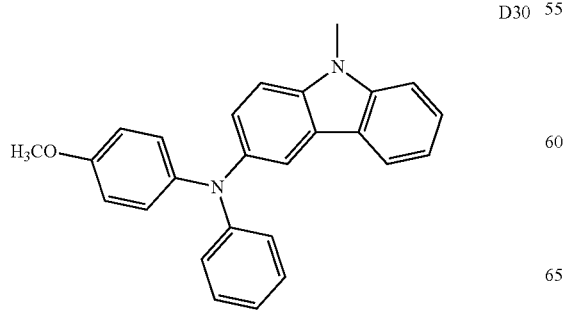
D30
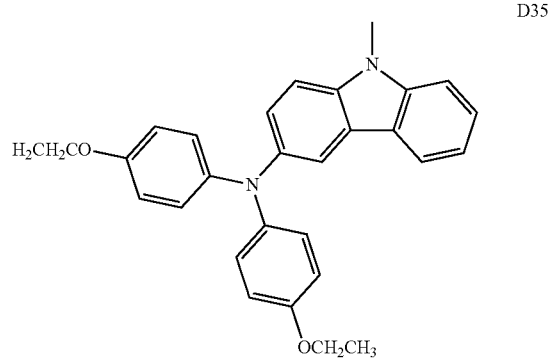
D35

-continued

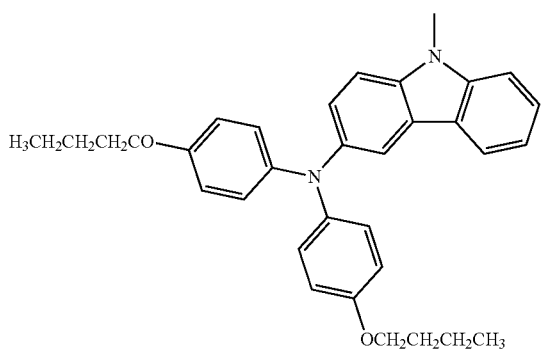
D26

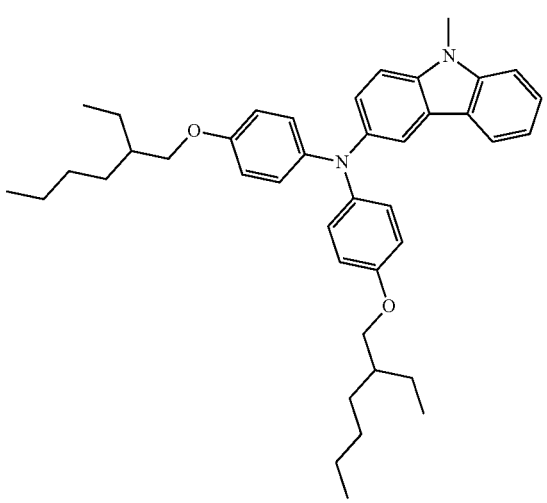
D37

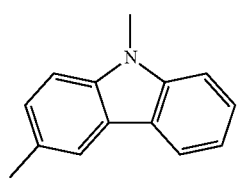
D40

-continued

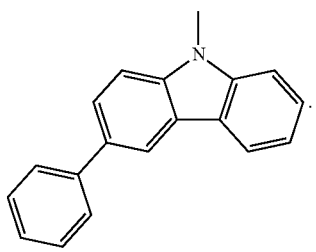
D42

2. The compound according to claim 1, wherein three or more of $R^1$, $R^2$, $R^4$, and $R^5$ each represent a 9-carbazolyl group substituted with one or more substituent selected from a substituted or unsubstituted branched alkyl group, a substituted or unsubstituted alkoxy group, and a substituted or unsubstituted diarylamino group, or an unsubstituted 9-carbazolyl group.

3. The compound according to claim 1, wherein three or more of $R^1$, $R^2$, $R^4$, and $R^5$ each represent a 9-carbazolyl group substituted with one or more substituted or unsubstituted branched alkyl group.

4. The compound according to claim 1, wherein all $R^1$, $R^2$, $R^4$, and $R^5$ each represent a substituted or unsubstituted 9-carbazolyl group.

5. The compound according to claim 1, wherein three of $R^1$, $R^2$, $R^4$, and $R^5$ each represent a substituted or unsubstituted 9-carbazolyl group.

6. The compound according to claim 1, wherein three or more of $R^1$, $R^2$, $R^4$, and $R^5$ represent unsubstituted 9-carbazolyl groups.

7. The compound according to claim 1, wherein three or more of $R^1$, $R^2$, $R^4$, and $R^5$ each represent a 9-carbazolyl group substituted with substituents at the 3-position and the 6-position.

8. The compound according to claim 1, wherein $R^3$ represents a hydrogen atom.

9. An organic light-emitting device comprising a substrate having thereon a light-emitting layer containing the compound according to claim 1.

10. The organic light-emitting device according to claim 9, wherein the organic light-emitting device is an organic electroluminescent device.

11. The organic light-emitting device according to claim 9, wherein the light-emitting layer contains the compound and a host material.

* * * * *